US011851503B2

(12) United States Patent
Chakrabarti et al.

(10) Patent No.: US 11,851,503 B2
(45) Date of Patent: Dec. 26, 2023

(54) ANTIPLASMODIAL COMPOUNDS

(71) Applicants: UNIVERSITY OF CENTRAL FLORIDA RESEARCH FOUNDATION, INC., Orlando, FL (US); THE BOARD OF REGENTS OF THE UNIVERSITY OF OKLAHOMA, Norman, OK (US)

(72) Inventors: Debopam Chakrabarti, Winter Springs, FL (US); Robert H. Cichewicz, Norman, OK (US); Shengxin Cai, Norman, OK (US); Jin Woo Lee, Norman, OK (US); Jennifer E. Collins, Osteen, FL (US)

(73) Assignees: UNIVERSITY OF CENTRAL FLORIDA RESEARCH FOUNDATION, INC., Orlando, FL (US); THE BOARD OF REGENTS OF THE UNIVERSITY OF OKLAHOMA, Norman, OK (US)

( * ) Notice: Subject to any disclaimer, the term of this patent is extended or adjusted under 35 U.S.C. 154(b) by 0 days.

(21) Appl. No.: 17/582,787

(22) Filed: Jan. 24, 2022

(65) Prior Publication Data
US 2022/0144894 A1    May 12, 2022

Related U.S. Application Data

(63) Continuation of application No. 16/655,147, filed on Oct. 16, 2019, now Pat. No. 11,230,569.

(60) Provisional application No. 62/746,160, filed on Oct. 16, 2018.

(51) Int. Cl.
| | |
|---|---|
| C07K 7/08 | (2006.01) |
| A61P 33/06 | (2006.01) |
| A61K 45/06 | (2006.01) |
| A61K 38/00 | (2006.01) |

(52) U.S. Cl.
CPC .............. C07K 7/08 (2013.01); A61P 33/06 (2018.01); *A61K 38/00* (2013.01); *A61K 45/06* (2013.01)

(58) Field of Classification Search
CPC .......... C07K 7/08; C07K 14/37; A61P 33/06; A61K 45/06; A61K 38/00; A61K 36/062; Y02A 50/30
See application file for complete search history.

(56) References Cited

U.S. PATENT DOCUMENTS

| | | | | |
|---|---|---|---|---|
| 6,110,697 A | * | 8/2000 | Dulski ................ | A61K 38/005 424/94.1 |
| 11,230,569 B2 | | 1/2022 | Chakrabarti et al. | |

OTHER PUBLICATIONS

Ochi et al (Canadian Journal of Plant Pathology, 2011, 33:3, 347-354) (Year: 2011).*
Miller et al (Journal of Medicinal Chemistry, 2003, vol. 46, No. 24, 5097-5116) (Year: 2003).*
Augeven-Bour, Isavelle et all, "Harzianin HB I, an 11-residue peptaibol from Trichoderma harzianum: isolation, sequence, solution synthesis and membrane activity", J. Chem. Soc., Perkin Trans. 1, 1997 pp. 1587-1594.
Auvin-Guette, Catherine et al., "Trichogin A IV, an 11-Residue Lipopeptaibol from Trichoderma longibrachiatum", J. Am. Chem. Soc., 1992, vol. 114, pp. 2170-2174.
Auvin-Guette, Catherin et all, "Structural Elucidation of Trikoningins KA and KB, Peptaibols from Trichoderma koningii", J. Chem. Soc. Perkin Trans 1, 1993, pp. 249-255.
Blasco, Benjamin et al., "Antimalarial drug resistance: linking Plasmodium falciparum parasite biology to the clinic", Nat Med, 2017, vol. 23, issue 8, pp. 917-928.
Boman, H.G. et al., "Antibacterial and antimalarial properties of peptides that are cecropin-melittin hybrids", FEBS Letters, Dec. 1989, vol. 259, No. 1, pp. 103-106.
Carballar-Lejarazu, R. et al., "Recombinant scorpine: a multifunctional antimicrobial peptide with activity against different pathogens", Cell. Mol. Life Sci., 2008, vol. 65, pp. 3081-3092.
China, Nicolas et al., "Structure and membran properties of trichogin GB Ix from Trichoderma longibrachiatum, the longest sequence among lipopeptaibols", Peptides 2000, Sep. 2000, 26th European Peptide Symposium, Montpellier, France, 5 pages.
Degenkolb, Thomas et al., "Peptaibiomics: Screening for Polypeptide Antibiotics (Peptaibiotics) from Plant-Protective *Trichoderma* Species", Chemistry & Biodiversity, 2006, vol. 3, pp. 593-610.
DeZotti, Marta et al., "Total Synthesis, Characterization, and Conformational Analysis of the Naturally Occurring Hexadecapeptide Integramide A and a Diastereomer", Chem. Eur. J., 2010, vol. 16, pp. 316-327.
Fujii, Kiyonaga et al., "A Nonempirical Method Using LC/MS for Determination of the Absolute Configuration of Constituent Amino Acids in a Peptide: Elucidation of Limitations of Marfey's Method and of Its Separation Mechanism", Anal. Chem., 1997, vol. 69, pp. 3346-3352.
Fujii, Kiyonaga et al., "A Nonempirical Method Using LC/MS for Determination of the Absolute Configuration of Constituent Amino Acids in a Peptide: Combination of Marfey's Method with Mass Spectrometry and Its Practical Application", Anal. Chem., 1997, vol. 69, pp. 5146-5151.
Fujita, Tetsuro et al., "Structural Elucidation of Trichosporin-B-Ka, IIIa, IIId and V from Trichoderma Polysporum", The Journal of Antibiotics, Jun. 1988, vol. XLI, No. 6., pp. 814-818.
Gao, Bin et al., "Characterization of two linear cationic antimalarial peptides in the scorpion *Mesobuthus eupeus*", Biochimie, 2010, vol. 92, pp. 350-359.
Goulard, Christophe et al., "Trichorzins HA and MA, Antibiotic Peptides from Trichoderma harzianum", The Journal of Antibiotics, Nov. 1995, vol. 48, No. 11, pp. 1248-1253.
Grauer, Andreas A. et al, "Stable Right- and Left-Handed Peptide Helices containing Ca-Tetrasubstituted a-Amino Acids", J. Org. Chem., 2009, vol. 74, pp. 3718-3726.

(Continued)

*Primary Examiner* — Sudhakar Katakam
(74) *Attorney, Agent, or Firm* — Timothy H. Van Dyke; WOLTER, VAN DYKE, DAVIS, PLLC

(57) ABSTRACT

Novel compositions and methods for the treatment and prevention of malaria are disclosed herein.

2 Claims, 20 Drawing Sheets

(56) References Cited

OTHER PUBLICATIONS

Gwadz, Robert W., "Effects of Magainins and Cecropins on the Sporogonic Development of Malaria Parasites in Mosquitoes", Infection and Immunity, Sep. 1989, vol. 57, No. 9, pp. 2628-2633.
Hayashi, Yumi et al., "Kozupeptins, Antimalarial Agents Produced by *Paracamarosporium* Species: Isolation, Structural Elucidation, Total Synthesis, and Bioactivity", Org. Letters, 2019, vol. 21, pp. 2180-2184.
Hayton, K. et al, "Genetic and Biochemical Aspects of Drug Resistance in Malaria Parasites", Current Drug Targets—Infectious Disorders, 2004, vol. 4, No. 1, 10 pages.
Hess, Sonja et al, "Chirality determination of unusual amino acids using precolumn derivatization and liquid chromatography-electrospray ionization mass spectrometry", Journal of Chromatography A, 2004, vol. 1035, pp. 211-219.
Hlimi, Sanae et al., "Trichorzins HA and MA, Antibiotic Peptides from Trichoderma harzianum", The Journal of Antibiotics, Nov. 1995, vol. 48, No. 11, pp. 1254-1261.
Huang, Qing et al., "Studies on Metabolites of Mycroparasitic Fungi. II. Metabolites of Trichoderma koningii", Chem. Pharm. Bull, Feb. 1995, vol. 43, No. 2, pp. 223-229.
Iida, Akira et al., "Fungal Metabolites. XVIII. New Membrane-Modifying Peptides, Trichorozins I-IV, from the Fungus *Trichoderma harzianum*", Chem. Pharm. Bull, 1995, vol. 43, No. 3, pp. 392-397.
Iwatsuki, Masato et al., "Antitrypanosomal peptaibiotics, trichosporins B-VIIa and B-VIIb, produced by Trichoderma polysporum FKI-4452", The Journal of Antibiotics, 2010, vol. 63, pp. 331-333.
Jaworski, Andreas et al., "Structures of Trichovirins II, Peptaibol Antibiotics from the Mold *Trichoderma viride* NRRL 6243", Journal of Peptide Science, 1999, vol. 5, pp. 341-351.
Jawroski, Andreas et al., "Detection of new sequences of peptaibol antibiotics trichotoxins A-40 by on-line liquid chromatography-electrospray ionization mass spectrometry", Journal of Chromatography A. vol. 863, 1999, pp. 179-189.
Jiao, Wei-Hua et al., "Trichodermides A-E: New Peptaibols Isolated from the Australian Termite Nest-Derived Fungus *Trichoderma virens* CMB-TN16", J. Nat. Prod. 2018, 81, 976-984.
Lacerda, Ariane F. et al., "Anti-parasitic Peptides from Arthropods and their Application in Drug Therapy", Frontiers in Microbiology, Feb. 2016, vol. 7, article 91, 11 pages.
Linington, Roger G. et al., "Antimalarial Peptides from Marine Cyanobacteria: Isolation and Structural Elucidation of Gallinamide A", J Nat Prod., 2009, vol. 72, No. 1, 11 pages.
Liu, Dong et al., "Microbacterins A and B, New Peptaibols from the Deep Sea Actinomycete *Microbacterium sediminis* sp. nov. YLB-01(T)", Organic Letters, 2015, vol. 17, pp. 1220-1223.
Nagaru, G. et al., "Antimalarial Activities of Peptide Antibiotics Isolated from Fungi", Antibicrobial Agents and Chemotherapy, Jan. 2001, vol. 45, No. 1, pp. 145-149.
Oh, Seung-Uk et al, "Atroviridins A-C and Neoatroviridins A-3, Novel Peptaibol Antibiotics Produced by Trichoderma artoviride F80317", The Journal of Antibiotics, Jun. 2002, vol. 55, No. 6, pp. 557-564.
Przybylski, M. et al., "Elucidatoin of Structure and Microheterogeneity of the Polypeptide Antibiotics Paracelsin and Trichotoxin A-50 by Fast Atom Bombardment Mass Spectrometry in Combination with Selective in situ Hydrolysis", Biomedical Mass Spectrometry, 1984, vol. 11, No. 11, pp. 569-582.
Rebuffat, Sylvie et al., "Antibiotic peptides from Trichoderma harzianum: harzianins HC, proline-rich 14-residue peptaibols", J. Chem. Soc. Perking Trans. 1, 1995, pp. 1849-1855.
Rohrich, Christian Rene et al., "Screening the Biosphere: The Fungicolous Fungus *Trichoderma phellinicola*, a Prolific Source of Hypophellins, New 17-, 18-, 19-, and 20-Residue Peptaibiotics", Chemistry & Biodiversity, 2013, vol. 10, pp. 787-812.
Singh, Sheo B. et al., "Structure, Histone Deacetylase, and Antiprotozoal Activities of Apicidins B and C, Congeners of Apicidin with Proline and Valine Substitutions", Organic Letters, 2001, vol. 3, No. 18, pp. 2815-2818.
Singh, Varun Pratap et al., "Lipovelutibols A-D: Cytotoxic Lipopeptaibols from the Himalayan Cold Habitat Fungus *Trichoderma velutinum*", Journal Natural Products., 2018, vol. 81, pp. 219-226.
Sinha, Shweta et al., "Challenges of drug-resistant malaria", Parasite, 2014, vol. 21, No. 61, 15 pages.
Smilkstein, Martin et al., "Simple and Inexpensive Fluorescence-Based Technique for High-Throughput Antimalarial Drug Screening", Antimicrobial Agents and Chemotherapy, May 2004, vol. 48, No. 5, pp. 1803-1806.
Trager, William et al., "Human Malaria Parasites in Continuous Culture", Science, Aug. 1976, vol. 193, pp. 673-675.
Tsantrizos, Youla S. et al., "Peptaibol metabolites of Tolypocladium geodes", Can. J. Chem., 1996, vol. 74, pp. 165-172.
Vizioli, Jacopo, et al., "Gambicin: A novel immune responsive antimicrobial peptide from the malaria vector Anopheles gambiae", PNAS, Oct. 2001, vol. 98, No. 22, pp. 12630-12635.
World Health Organization, "World Malaria Report 2018", 210 pages.
Zhao, Lei et al., "Rhabdopeptide/Xenortide-like Peptides from Xenorhabdus innexi with Terminal Amines Showing Potent Antiprotozoal Activity", Organic Letters, 2018, vol. 20, pp. 5116-5120.
Collins, Jennifer, "Novel Antiplasmodial Compounds from Fungi", Presentation at Keystone Symposia on Molecular and Cellular Biology, Oct. 20, 2018, 16 pages.

* cited by examiner

Table 1. Inhibitory Effects of 18-AA Peptaibols (1-5 and 15-19)

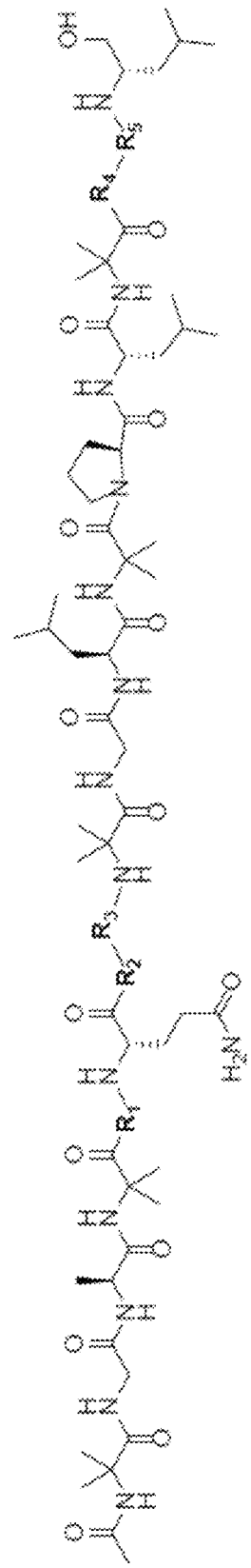

| Compounds | M.W. | $R_1$ | $R_2$ | $R_3$ | $R_4$ | $R_5$ | P. falciparum $EC_{50}$ (μM)[a] | Hep G2 $EC_{50}$ (μM)[a] | Selectivity Index (SI) |
|---|---|---|---|---|---|---|---|---|---|
| Trichorzin NP A (1) | 1703 | L-Ala | Aib | L-Val | D-Iva | L-Gln | 1.18 | 16.4 | 14 |
| Trichorzin NP B (2) | 1704 | Aib | Aib | L-Val | Aib | L-Glu | 1.77 | >25 | >14 |
| Trichorzin NP C (3) | 1731 | Aib | D-Iva | L-Val | D-Iva | L-Gln | 0.86 | 12.1 | 14 |
| Trichorzin NP D (4) | 1745 | D-Iva | Aib | L-Ile | D-Iva | L-Gln | 0.58 | 9.6 | 17 |
| Trichorzin NP E (5) | 1759 | D-Iva | D-Iva | L-Ile | D-Iva | L-Gln | 0.85 | 5.9 | 7 |
| Trichorzin HA I (15) | 1703 | Aib | Aib | L-Val | Aib | L-Gln | 1.22 | 19.9 | 16 |
| Trichorzin HA II (16) | 1717 | Aib | Aib | L-Val | D-Iva | L-Gln | 0.44 | 12.3 | 28 |
| Trichorzin HA V (17) | 1731 | D-Iva | Aib | L-Val | D-Iva | L-Gln | 0.74 | 14.7 | 20 |
| Trichorzin HA VI (18) | 1745 | D-Iva | D-Iva | L-Val | D-Iva | L-Gln | 0.90 | 18.0 | 20 |
| Trichorzin HA VII (19) | 1745 | D-Iva | L-Val | L-Val | D-Iva | L-Gln | 0.56 | 11.1 | 19 |

[a] Results are expressed as means from triplicate experiments.

FIG. 1

Table 2. Inhibitory Effects of 14-AA Peptaibols (6-13 and 20-26)

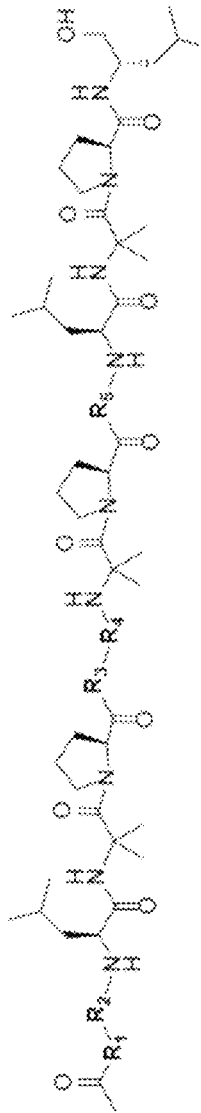

| Compounds | M.W. | R1 | R2 | R3 | R4 | R5 | P. falciparum EC50 (μM)[a] | Hep G2 EC50 (μM)[a] | SI |
|---|---|---|---|---|---|---|---|---|---|
| Harzianin NP A (6) | 1415 | D-Iva | L-Asn | L-Ser | L-Val | Aib | 0.63 | >25 | >40 |
| Harzianin NP B (7) | 1429 | Aib | L-Gln | L-Ser | L-Ile | Aib | 1.74 | >25 | >14 |
| Harzianin NP C (8) | 1429 | D-Iva | L-Asn | L-Ser | L-Ile | Aib | 0.57 | >25 | >44 |
| Harzianin NP D (9) | 1443 | D-Iva | L-Asn | L-Ser | L-Ile | D-Iva | 0.51 | >25 | >29 |
| Harzianin NP E (10) | 1413 | Aib | L-Gln | L-Ala | L-Ile | Aib | 0.29 | >25 | >85 |
| Harzianin NP F (11) | 1427 | D-Iva | L-Gln | L-Ala | L-Ile | Aib | 0.31 | >25 | >85 |
| Harzianin NP G (12) | 1427 | D-Iva | L-Asn | L-Ala | L-Ile | D-Iva | 0.62 | >25 | >40 |
| Harzianin NP H (13) | 1441 | D-Iva | L-Gln | L-Ala | L-Ile | D-Iva | 0.29 | >25 | >85 |
| Harzianin HC I (20) | 1401 | Aib | L-Asn | L-Ser | L-Ile | Aib | 0.67 | >25 | >37 |
| Harzianin HC III (21) | 1415 | Aib | L-Asn | L-Ser | L-Val | D-Iva | 0.61 | >25 | >41 |
| Harzianin HC XI (22) | 1415 | Aib | L-Asn | L-Ser | L-Val | D-Iva | 0.61 | >25 | >41 |
| Harzianin HC XII (23) | 1429 | Aib | L-Asn | L-Ser | L-Ile | D-Iva | 0.51 | >25 | >48 |
| Harzianin HC XIV (24) | 1399 | Aib | L-Asn | L-Ala | L-Ile | Aib | 0.42 | >25 | >60 |
| Harzianin HC X (25) | 1413 | Aib | L-Gln | L-Ala | L-Val | D-Iva | 1.31 | >25 | >19 |
| Harzianin HC XV (26) | 1427 | Aib | L-Gln | L-Ala | L-Ile | D-Iva | 0.62 | >25 | >40 |

[a] Results are expressed as means from triplicate experiments.

FIG. 2

Table 3. Inhibitory Effects of 11-AA Peptaibols (14 and 27)

| Compounds | M.W. | R₁ | R₂ | P. falciparum EC₅₀ (μM)[a] | Hep G2 EC₅₀ (μM)[a] | SI |
|---|---|---|---|---|---|---|
| Harzianin NP I (14) | 1188 | D-Iva | L-Gln | 0.36 | >25 | >68 |
| Harzianin HB I (27) | 1160 | Aib | L-Asn | 0.77 | >25 | >32 |

[a] Results are expressed as means from triplicate experiments.

Table 4. Inhibitory Effects of 7-AA Lipopeptaibols (28-30)

| Compounds | M.W. | R₁ | R₂ | P. falciparum EC₅₀ (μM)ᵃ | Hep G2 EC₅₀ (μM)ᵃ | SI |
|---|---|---|---|---|---|---|
| Hypocrin NP A (28) | 739 | L-Val | L-Ile | 1.08 | >25 | >23 |
| Hypocrin NP B (29) | 739 | L-Leu | L-Val | 2.94 | >25 | >8 |
| Hypocrin NP C (30) | 753 | L-Leu | L-Ile | 3.15 | >25 | >8 |

ᵃResults are expressed as means from triplicate experiments.

Table 5. Inhibitory Effects of 11-AA Lipopeptaibols (31-36 and 44-45)

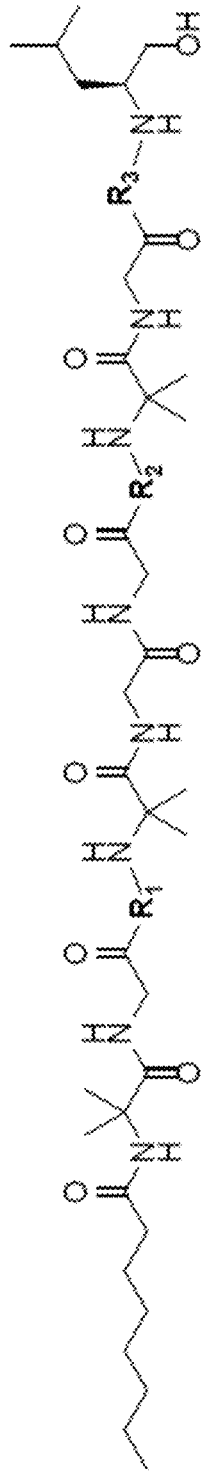

| Compounds | M.W. | $R_1$ | $R_2$ | $R_3$ | P. falciparum EC$_{50}$ (μM)$^a$ | Hep G2 EC$_{50}$ (μM)$^a$ | SI |
|---|---|---|---|---|---|---|---|
| Hypocrin ND A (31) | 1023 | L-Val | L-Val | L-Val | 3.66 | >25 | >7 |
| Hypocrin ND B (32) | 1037 | L-Leu | L-Val | L-Val | 2.52 | >25 | >10 |
| Hypocrin ND C (33) | 1051 | L-Leu | L-Val | L-Leu | 0.88 | >25 | >28 |
| Hypocrin ND D (34) | 1051 | L-Leu | L-Val | L-Ile | 3.23 | >25 | >8 |
| Hypocrin ND E (35) | 1051 | L-Val | L-Leu | L-Ile | 1.93 | >25 | >13 |
| Hypocrin ND F (36) | 1065 | L-Leu | L-Leu | L-Leu | 2.15 | >25 | >12 |
| Trikoningin KB I (44) | 1037 | L-Val | L-Val | L-Ile | 0.88 | 12.6 | 15 |
| Trichogin A IV (45) | 1065 | L-Leu | L-Leu | L-Ile | 0.92 | 8.0 | 9 |

$^a$ Results are expressed as means from triplicate experiments.

FIG. 5

Table 6. Inhibitory Effects of 15-AA Lipopeptaibols (37-43 and 46)

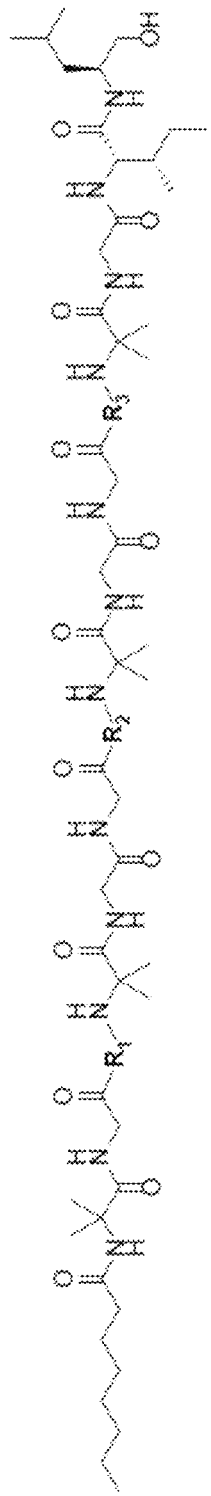

| Compounds | M.W. | R₁ | R₂ | R₃ | P. falciparum EC₅₀ (μM)ᵃ | Hep G2 EC₅₀ (μM)ᵃ | SI |
|---|---|---|---|---|---|---|---|
| Hypocrin NG A (37) | 1335 | L-Leu | L-Val | L-Val | 0.42 | >25 | >59 |
| Hypocrin NG B (38) | 1349 | L-Val | L-Val | L-Val | 2.27 | >25 | >11 |
| Hypocrin NG C (39) | 1349 | L-Val | L-Leu | L-Val | 1.40 | >25 | >18 |
| Hypocrin NG D (40) | 1349 | L-Val | L-Val | L-Leu | 2.52 | >25 | >10 |
| Hypocrin NG E (41) | 1363 | L-Val | L-Leu | L-Leu | 2.41 | >25 | >10 |
| Hypocrin NG F (42) | 1363 | L-Leu | L-Val | L-Leu | 0.78 | 23.4 | 30 |
| Hypocrin NG G (43) | 1363 | L-Leu | L-Leu | L-Val | 0.87 | >25 | >29 |
| Trichogin A IV (46) | 1377 | L-Leu | L-Leu | L-Leu | 0.54 | 15.8 | 29 |

ᵃ Results are expressed as means from triplicate experiments.

FIG. 6

Table 7. Inhibitory Effects of 20-AA Peptaibols (47-52)

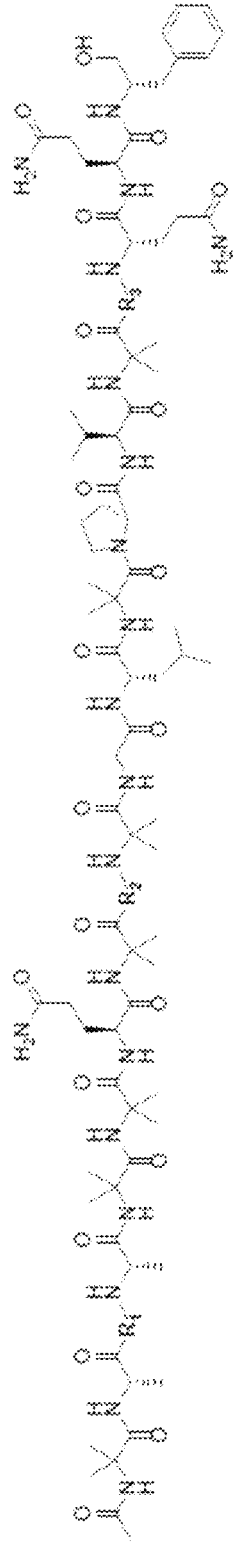

| Compounds | M.W. | R₁ | R₂ | R₃ | P. falciparum EC₅₀ (µM)ᵃ | Hep G2 EC₅₀ (µM)ᵃ | SI |
|---|---|---|---|---|---|---|---|
| Trichosporin B IIId (47) | 1936 | L-Ala | L-Val | Aib | 0.30 | 9.08 | 11 |
| Trichosporin B IIIa (48) | 1950 | L-Ala | L-Leu | Aib | 0.31 | 5.82 | 18 |
| Trichosporin B IVc (49) | 1950 | Aib | L-Val | Aib | 0.58 | 6.83 | 12 |
| Trichosporin B VIb (50) | 1964 | L-Ala | L-Ile | D-Iva | 0.49 | 3.50 | 7 |
| Trichosporin B VIa (51) | 1964 | Aib | L-Ile | Aib | 0.72 | 2.62 | 3 |
| Trichosporin B VIIa (52) | 1978 | Aib | L-Ile | D-Iva | 0.81 | 3.54 | 5 |

ᵃ Results are expressed as means from triplicate experiments.

FIG. 7

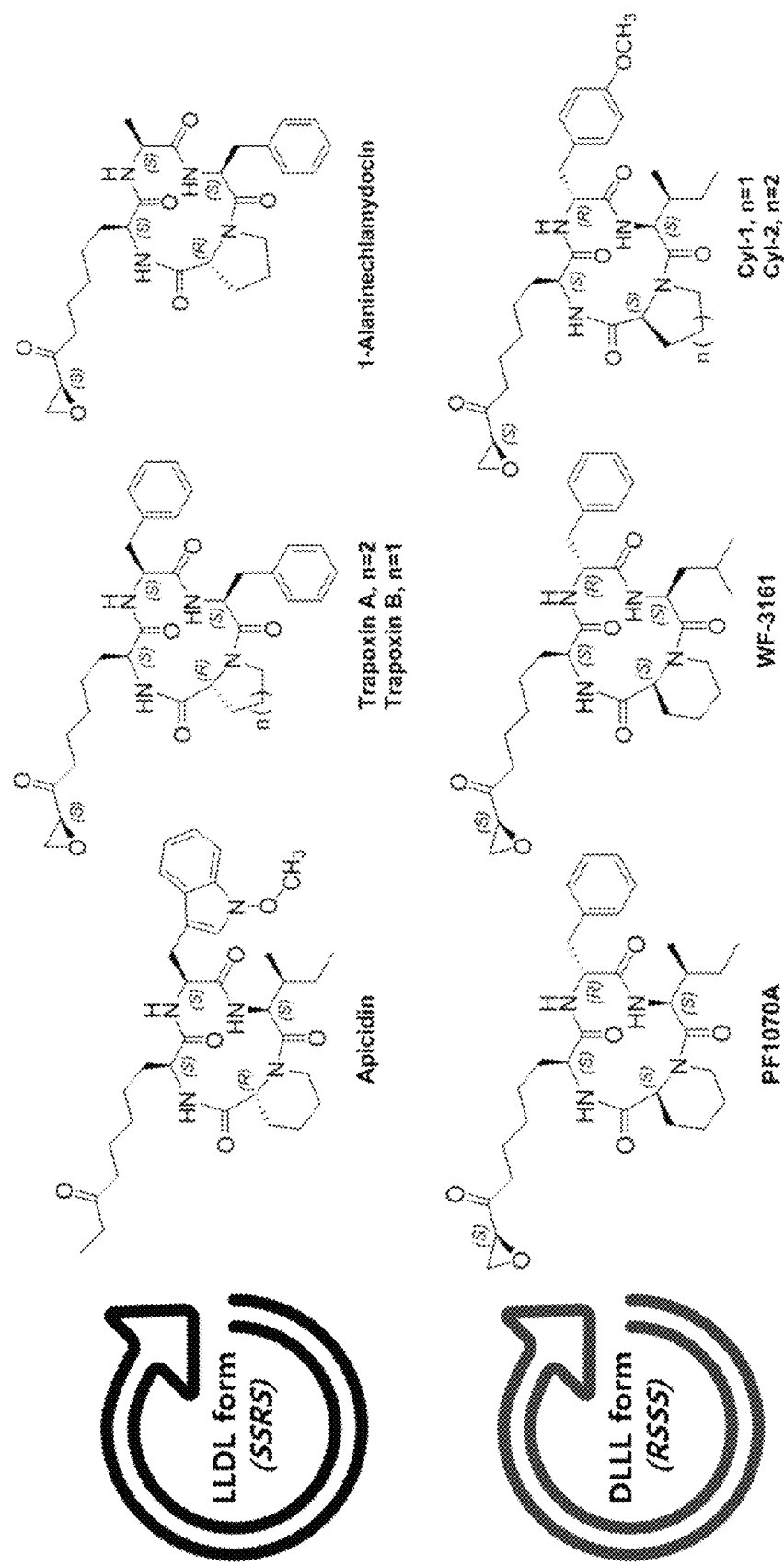
Figure 16. Two Types of Macrocyclic Ring Conformations, LLDL (SSRS) and DLLL (RSSS) form.

Figure 17

Table 9. Antimalarial Effects of Natural RSSS Form Cyclic Tetrapeptides (1-13)

| No. | R₁ | R₂ | Pf. EC$_{50}$ (nM)$^a$ | Hep G2 EC$_{50}$ (nM)$^a$ | Selectivity Index (SI) | PfHDAC1 EC50 (nM) |
|---|---|---|---|---|---|---|
| 137LJ57K1 PF 1070A (1) | sec-butyl | epoxyketone | 88 ± 9 | 13,103 ± 1,946 | 149 | 3 |
| 137LJ57I1 NA 1309 (2) | sec-butyl | HO-CH₂CH₂-C(O)- | >5,000 | >25,000 | - | >10,000 |
| 137LJ57E1 (3) | sec-butyl | (OH)(OH)-diol | >5,000 | >25,000 | - | >10,000 |
| 137LJ57A1 (4) | sec-butyl | HO-CH₂-CH(OH)-C(O)- | 2,498 ± 89 | >25,000 | >10 | 4,810 |
| 137LJ118F (5) | sec-butyl | HOOC- | >5,000 | >25,000 | - | >10,000 |
| 137LJ57K2 WF-3161 (6) | isobutyl | epoxyketone | 117 ± 12 | 20,601 ± 3,314 | 176 | 0.008 |
| 137LJ57I2 (7) | isobutyl | HO-CH₂CH₂-C(O)- | >5,000 | >25,000 | - | >10,000 |
| 137LJ57E2 (8) | isobutyl | (OH)(OH)-diol | >5,000 | >25,000 | - | >10,000 |
| 137LJ57A2 (9) | isobutyl | HO-CH₂-CH(OH)-C(O)- | | | | |
| 137LJ118G (10) | isobutyl | HOOC- | 1,475 ± 52 | >25,000 | >17 | 993 |
| 137LJ57C1 (11) | isopropyl | epoxyketone | 1,465 ± 210 | >25,000 | 17 | 12 |
| 137LJ57C2 (12) | isopropyl | HO-CH₂-CH(OH)-C(O)- | 2,760 ± 106 | >25,000 | >9 | 1,655 |
| 137LJ118C (13) | isopropyl | HOOC- | >5,000 | >25,000 | - | 587 |

$^a$ Results are expressed as means from triplicate experiments.

Figure 18

Table 10. Antimalarial Effects of Synthetic *RSSS* Form Cyclic Tetrapeptides (14-24)

| No. | R₁ | R₂ | *Pf.* EC$_{50}$ (nM)$^a$ | Hep G2 EC$_{50}$ (nM)$^a$ | Selectivity Index (SI) | *Pf*HDAC1 EC50 (nM) |
|---|---|---|---|---|---|---|
| 137LJ121A (14) (=137LJ121A2) | sec-butyl | epoxide-CH(OH)CH₃ | >5,000 | >25,000 | - | >10,000 |
| 137LJ121B (15) (=137LJ121B2) | sec-butyl | epoxide-CH(OH)CH₃ | >5,000 | >25,000 | - | >10,000 |
| 137LJ123A (16) | isobutyl | epoxide-CH(OH)CH₃ | | | | |
| 137LJ123B (17) (=137LJ121C) | isobutyl | epoxide-CH(OH)CH₃ | >5,000 | >25,000 | - | >10,000 |
| 137LJ123C (18) (=137LJ121A1) | sec-butyl | HOCH₂-CH(OH)-CH(OH)- | >5,000 | >25,000 | - | >10,000 |
| 137LJ123D (19) (=137LJ121B1) | sec-butyl | HOCH₂-CH(OH)-CH(OH)- | >5,000 | >25,000 | - | 2,199 |
| 137LJ124A (20) | sec-butyl | HOCH₂-CH(OAc)-C(O)- | | | | |
| 137LJ124B (21) | sec-butyl | AcOCH₂-CH(OH)-C(O)- | | | | |
| 137LJ124C (22) | sec-butyl | AcOCH₂-CH(OAc)-C(O)- | | | | |
| 137LJ124E (23) | sec-butyl | H₃COCH₂-CH(OH)-C(O)- | | | | |
| 137LJ123G (24) | isobutyl | H₃COCH₂-CH(OH)-C(O)- | | | | |

$^a$ Results are expressed as means from triplicate experiments.

Figure 19

Table 11. Antimalarial Effects of SSRS Form Cyclic Tetrapeptides (25-26)

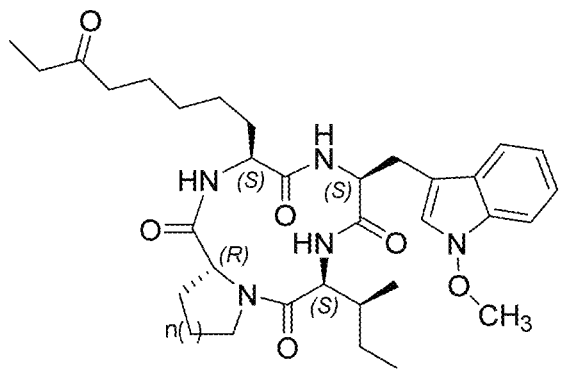

| No. | n | Pf. EC$_{50}$ (nM)$^a$ | Hep G2 EC$_{50}$ (nM)$^a$ | Selectivity Index (SI) | PfHDAC1 EC50 (nM) |
|---|---|---|---|---|---|
| Apicidin B (25) | 1 | 345 ± 27 | 4,517 ± 320 | 13 | 268.5 |
| Apicidin C (26) | 2 | 230 ± 7 | 6,205 ± 87 | 27 | 487 |

$^a$ Results are expressed as means from triplicate experiments.

Figure 20

Table 12. Antimalarial Effects of SSRS Form Cyclic Tetrapeptides (27-28)

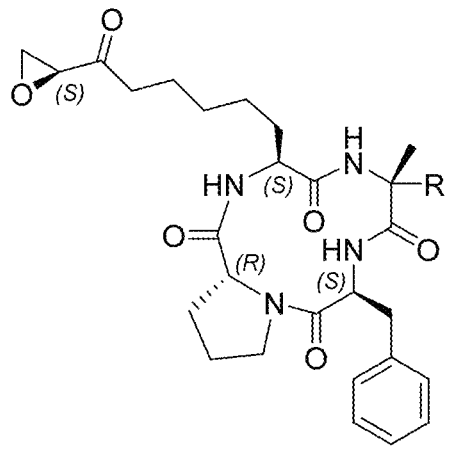

| No. | R | Pf. EC$_{50}$ (nM)$^a$ | Hep G2 EC$_{50}$ (nM)$^a$ | Selectivity Index (SI) | PfHDAC1 EC50 (nM) |
|---|---|---|---|---|---|
| Chlamydocin (27) | CH$_3$ | 32 ± 10 | 523 ± 7 | 16 | - |
| 1-Alaninechlamydocin (28) | H | 8 ± 1 | 26 ± 6 | 3 | 303.5 |

$^a$ Results are expressed as means from triplicate experiments

ANTIPLASMODIAL COMPOUNDS

STATEMENT REGARDING FEDERALLY SPONSORED RESEARCH OR DEVELOPMENT

This invention was made with government support under AI143052 awarded by the National Institutes of Health. The government has certain rights in this invention.

BACKGROUND

Malaria is an infectious disease caused by a microorganism of the genus *Plasmodium*. Upon infection, the parasites (sporozoites) travel to the liver where they mature and release another form of parasites called merozoites. The parasites enter the bloodstream and multiply inside red blood cells, which then break open and infect more red blood cells. Malaria may be treated with oral medications such as chloroquine, quinine sulfate, hydroxychloroquine, mefloquine, atovaquone, and/or proguanil amongst other agents. It is known that these malarial parasites may evolve and become resistant to the administered medications. In many cases, the parasite is able to survive and continue to multiply despite being targeted with anti-malarial compounds.

Malaria, which is caused by *Plasmodium* parasites, is one of the most devastating infectious disease transmitted by the bite of *Anopheles* mosquitoes in the tropical regions. According to the world malaria report 2018 of the World Health Organization (WHO), there were an estimated 219 million cases of malaria occurred worldwide and 435,000 related deaths in 2017.[i] There is a structural classification of drugs being used clinically for the treatment of malaria: (1) sesquiterpene peroxides (e.g. artemisinin derivatives and analogues), (2) aryl amino alcohols (e.g. quinine, quinidine, mefloquine), (3) 4-aminoquinolines (e.g. chloroquine, amodiaquine), (4) 8-aminoquinolines (e.g. primaquine, tafenoquine), (5) antifolates (e.g. sulfadoxine, pyrimethamine), (6) antimicrobials (e.g. doxycycline, tetracycline, clindamycin), and (7) naphthoquinone (e.g. atovaquone, buparvaquone) (FIG. 1). Antimalarial drugs have been steadily developed, however, as they have been used extensively, *Plasmodium* parasites also have been getting drug-resistance and evolve quickly.[ii] Therefore, it is necessary to discover new classes of drugs with novelty, effectiveness, and safety.

These days, several peptides have been reported as potential antimalarial agents. Specifically, insect-derived peptides showed their inhibitory activity against *Plasmodium* parasites.[iii] Cecropins isolated from giant silk moths inhibited the growth of *P. falciparum* cells,[iv] and, scorpine and meucine-25, which were obtained from scorpion's venoms, also showed antimalarial activity against *P. falciparum* and *P. berghei*.[v] In particular, gambicin, which was isolated from *Plasmodium*'s insect host (*Anopheles* species mosquitoes) also displayed an inhibitory effect against *P. berghei* ookinetes.[vi] A microorganism is another important source to get novel compounds. For instance, gallinamide A, bacteria-derived peptides, isolated from marine cyanobacteria, and rhabdopeptide/xenortide-like peptides (RXPs) from *Xenorhabdus innexi* showed potent antiprotozoal activity on *P. falciparum* with an $IC_{50}$ value of 8.4 μM and 0.091-3.16 μM, respectively.[vii] For fungal-derived peptides, cyclic tetrapeptide apicidins obtained from *Fusarium pallidoroseum*, which are famous for reversibly inhibiting histone deacetylase (HDAC) inhibitor, also exhibited MIC values of 189 nM against *P. falciparum*.[viii] Recently, kozupeptins A and B isolated from *Paracamarosporium* sp. were reported about potent antimalarial activity against chloroquine-sensitive and -resistant *P. falciparum* strains in vitro with an $IC_{50}$ value of 0.15-1.46 μM.[ix] Since lots of literature have been finding antimalarial peptides from various source, non-ribosomal peptides such as peptaibols and lipopeptaibols can be potential as antimalarial agents. Antiamoebin, efrapeptins, and zervamicins derived from fungal species killed *P. falciparum* in culture with an $IC_{50}$ value in the range of 0.45-6.16 μM.[x]

BRIEF SUMMARY

These and other features, aspects, and advantages of various embodiments will become better understood with reference to the following description, figures, and claims.

BRIEF DESCRIPTION OF THE FIGURES

Many aspects of this disclosure can be better understood with reference to the following figures, in which:

FIG. 1: is an example according to various embodiments illustrating a peptaibol structure and a table indicating inhibitory effects for variations on the structure;

FIG. 2: is an example according to various embodiments illustrating a peptaibol structure and a table indicating inhibitory effects for variations on the structure;

FIG. 5: is an example according to various embodiments illustrating a lipopeptaibol structure and a table indicating inhibitory effects for variations on the structure;

FIG. 6: is an example according to various embodiments illustrating a lipopeptaibol structure and a table indicating inhibitory effects for variations on the structure;

FIG. 7: is an example according to various embodiments illustrating a peptaibol structure and a table indicating inhibitory effects for variations on the structure;

FIG. 10: Hyperacetylation after compound addition.

FIG. 11(A) Formation of HDAC8-TSA complex from SI of Porter (2017) ACS Chem Biol. FIG. 11(B) Proposed mechanism of activity of the catalytic domain of the HDACi with Zn and subgroups through formation of a geminal-diolate. FIG. 11(C) Hierarchy of a enzymatic activity of R2 groups. FIG. 11(D) Loss of activity upon elimination of ketone group.

FIG. 16: Provides a diagram of two different macrocyclic ring conformations, LLDL (SSRS) and DLLL (RSSS) form of HDAC inhibitor type agents.

FIG. 17: Provides a Table (Table 9) pertaining to antimalarial Effects of Natural RSSS form of cyclic tetrapeptides as well as their EC$_{50}$ for the noted assays as well as selectivity index (SI).

FIG. 18: Provides a Table (Table 10) pertaining to antimalarial Effects of Natural RSSS form of cyclic tetrapeptides as well as their EC$_{50}$ for the noted assays as well as selectivity index (SI).

FIG. 19: Provides a Table (Table 11) pertaining to antimalarial Effects of Natural SSRS form of cyclic tetrapeptides as well as their EC$_{50}$ for the noted assays as well as selectivity index (SI).

FIG. 20: Provides a Table (Table 12) pertaining to antimalarial Effects of Natural SSRS form of cyclic tetrapeptides as well as their EC$_{50}$ for the noted assays as well as selectivity index (SI).

Figure 3:
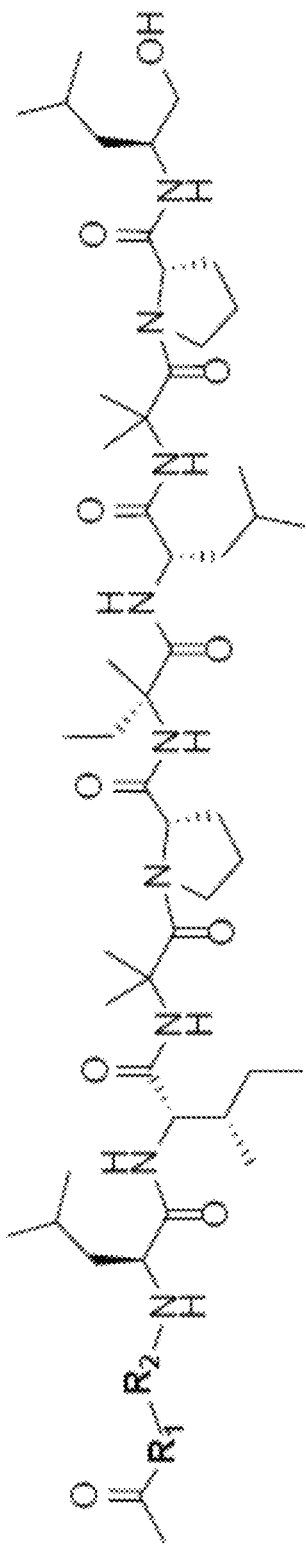
FIG. 3: is an example according to various embodiments illustrating a peptaibol structure and a table indicating inhibitory effects for variations on the structure.

It should be understood that the various embodiments are not limited to the examples illustrated in the figures.

DETAILED DESCRIPTION

Introduction and Definitions

Various embodiments may be understood more readily by reference to the following detailed description. Unless defined otherwise, all technical and scientific terms used herein have the same meaning as commonly understood by one of ordinary skill in the art to which this disclosure belongs.

As used herein, the term "standard temperature and pressure" generally refers to 25° C. and 1 atmosphere. Standard temperature and pressure may also be referred to as "ambient conditions." Unless indicated otherwise, parts are by weight, temperature is in ° C., and pressure is at or near atmospheric. The terms "elevated temperatures" or "high-temperatures" generally refer to temperatures of at least 100° C.

The term "mol percent" or "mole percent" generally refers to the percentage that the moles of a particular component are of the total moles that are in a mixture. The sum of the mole fractions for each component in a solution is equal to 1.

It is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

All numeric values are herein assumed to be modified by the term "about," whether or not explicitly indicated. The term "about" generally refers to a range of numbers that one of skill in the art would consider equivalent to the recited value (i.e., having the same function or result). In many instances, the term "about" may include numbers that are rounded to the nearest significant figure.

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by prior disclosure. Further, the dates of publication provided could be different from the actual publication dates that may need to be independently confirmed.

Unless otherwise indicated, the present disclosure is not limited to particular materials, reagents, reaction materials, manufacturing processes, or the like, as such can vary. It is also to be understood that the terminology used herein is for purposes of describing particular embodiments only and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

The following abbreviations are used herein: NMR, nuclear magnetic resonance; ECD, electronic circular dichroism; HRESIMS, high-resolution electrospray ionization mass spectrometry; GITC, 2,3,4,6-tetra-O-acetyl-β-D-glucopyranosyl isothiocyanate; SI, selectivity index; VLC, vacuum liquid chromatography; ITS, internal transcribed spacer; FDAA, 1-fluoro-2-4-dinitrophenyl-5-$_L$-alanine amide; HDAC, histone deacetylase; MIC, minimum inhibitory concentration; SAR, structureactivity relationship; HSQC, heteronuclear single quantum coherence spectroscopy; HMBC, heteronuclear multiple bond correlation spectroscopy; COSY, homonuclear correlation spectroscopy; ROESY, rotating frame nuclear overhauser effect spectroscopy; amu, atomic mass unit; TFA, trifluoroacetic acid; AA, amino acid; Aib, 2-Aminoisobutyric acid; Gly, glycine; Ala, alanine; Gln, glutamine; Val, valine; Leu, leucine; Pro, proline; Iva, isovaline; Leuol, leucinol; Ac, acetyl; Asn, aspartame; Asp, aspartic acid; Glu, glutamic acid; Ser, serine; Ile, isoleucine; Pheol, phenylalaninol.

All the features disclosed in this specification (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

The examples and embodiments described herein are for illustrative purposes only and that various modifications or changes in light thereof will be suggested to persons skilled in the art and are to be included within the spirit and purview of this application. Many variations and modifications may be made to the above-described embodiment(s) of the disclosure without departing substantially from the spirit and principles of the disclosure. All such modifications and variations are intended to be included herein within the scope of this disclosure.

The present disclosure is directed to new antiplasmodial compounds isolated from fungi and use as antiplasmodial (e.g. as anti-malarial) therapy. According to certain embodiments, the disclosure provides methods of treating or preventing malarial infection involving the administration of the enumerated compounds taught herein to a subject in need.

Overview

In the pursuit to discover next generation of antimalarials from novel areas of chemical space, a large library of diverse fungi was screened to discover secondary metabolites active against malaria parasite. Filamentous fungi are rich source of secondary metabolites possessing a wide range of novel pharmacophores. The Cichewicz fungal collection contains tens of thousands of fungal isolates that were secured from diverse habitats and ecological niches across the United States. It is believed that fungal secondary metabolites, which are underexplored for antimalarial drug discovery, provide a unique opportunity to explore medicinally relevant, but untapped chemical space for the discovery of essential malaria therapeutics. Libraries of 750 pure compounds, and of 460 extracts obtained from diverse fungal sources have been screened for their ability to inhibit intraerythrocytic growth of chloroquine-resistant $P.$ $falciparum$ Dd2 using a SYBR Green 1-based fluorescence assay. As a counter screen, the cytotoxicity of the top ten extracts in HepG2 cells was evaluated using the MTS ((3-(4,5 dimethylthiazol-2-yl)-5-(3-carboxymethoxyphenyl)-2-(4-sulfophenyl)-2H-tetrazolium, inner salt) cell proliferation assay. This screening has identified potent and selective novel antiplasmodial compounds. These unique pharmacophores from wide areas of chemical space would provide chemical starting points to develop lead compounds for drugs against malaria.

Of the hits found, several have known targets in other model systems, allowing us to expedite target analysis. One such compound is Chlamydocin, a known Class I HDAC inhibitor. Western blot analysis of $Plasmodium$ extracts confirms that analogs of this compound causes hyperacetylation of histone 4 and is suspected to target $Plasmodium$ HDAC1. The analog compound (PF1070A) is highly potent with an $EC_{50}$ at 37 nM against multidrug resistant malaria and is selective.

Definitions

It is important to an understanding of the present invention to note that all technical and scientific terms used herein, unless defined herein, are intended to have the same meaning as commonly understood by one of ordinary skill in the art. The techniques employed herein are also those that are known to one of ordinary skill in the art, unless stated otherwise. Prior to setting forth the invention in detail and for purposes of more clearly facilitating an understanding the invention as disclosed and claimed herein, the following definitions are provided.

As used herein, the terms "about" and "approximately" as used herein refers to—values that are ±10% of the stated value.

As used herein, the terms "administering" or "administration" of a composition as described herein to a subject includes any route of introducing or delivering to a subject a compound to perform its intended function. The administering or administration can be carried out by any suitable route, including orally, intranasally, parenterally (intravenously, intramuscularly, intraperitoneally, or subcutaneously), rectally, or topically. Administering or administration includes self-administration and the administration by another.

As used herein, the term "analog" refers to a compound having a structure similar to that of another one but differing from it with respect to a certain component. The compound may differ in one or more atoms, functional groups, or substructures, which may be replaced with other atoms, groups, or substructures. In one aspect, such structures possess at least the same or a similar therapeutic efficacy.

As used herein, "anti-malarial" or "anti-malarial activity" includes any activity that decreases the infectivity, the reproduction, or inhibits the progress of the lifecycle of a malaria parasite. "Anti-malarial activity" includes inhibition of the growth of malaria infection by all of the means of observed with current anti-malarial drugs.

As used herein, the term "enumerated agent(s)" refers to any compound that inhibits intraerythrocytic growth of $P.$ $falciparum$ described herein. In particular, enumerated agents include agents 1-52 provided in the figures and those provided in Table 8 below and Tables 9-12 in FIGS. 17-20. In specific embodiments, the enumerated agent is an HDAC inhibitor or peptaibol.

As used herein, the term "HDAC" inhibitor pertains to an agent that inhibits histone deacetylase.

As used herein, the term "peptaibol" pertains to a biologically active peptide containing between seven and twenty amino acid residues, some of which are non-proteinogenic amino acids.

One group of enumerated agents include thirty new peptaibols (1-14 and 28-43), along with 22 known compounds (15-27 and 44-52), were isolated from the bioactivity-guided fractionation of the ethyl acetate extract of $Trichoderma$ $harzianum$ and $Hypocrea$ $pachybasioides$. Their absolute configurations were elucidated by a combination of spectroscopic data (1 D and 2D NMR, ECD, HRESIMS, and MS/MS analysis), and chemical methods (Marfey's and GITC methods). All isolates (1-52) were found to have antimalarial activity, with their $EC_{50}$ in the range of 0.29-3.66 μM and good selectivity index (SI) values.

FIGS. 1-3 and 7 are examples according to various embodiments illustrating peptaibol structures and a table indicating inhibitory effects for variations on the respective structure. All isolated peptaibols (1-52) could be generally divided into two groups, acetyl-peptaibols (1-27 and 47-52) with the acetyl group at the N-terminal and lipopeptaibols (28-46) with the n-octanoyl moiety at the N-terminus.

Acetyl-peptaibols were further divided into four small groups depending on the length of sequence, 18-AA peptaibols (1-5 and 15-19, Table 1 in FIG. 1), 14-AA peptaibols (6-13 and 20-26, Table 2 in FIG. 2), 11-AA peptaibols (14 and 27, Table 3 in FIG. 3), and 20-AA peptaibols (47-52, Table 7 in FIG. 7).

Figure 4:
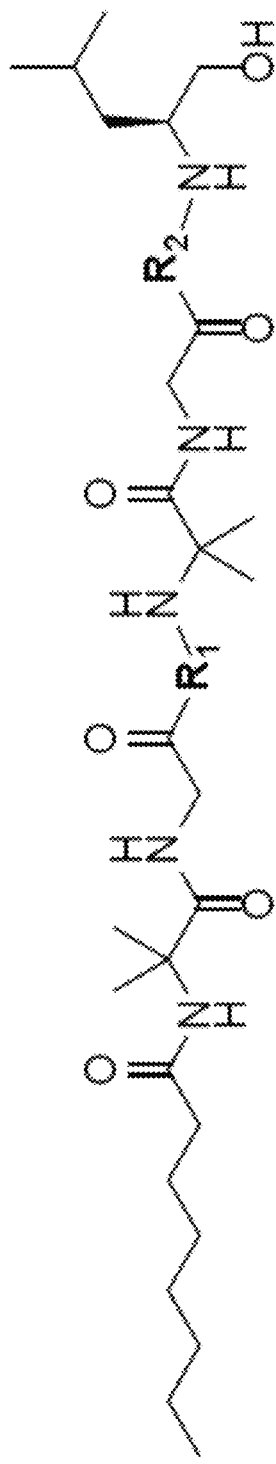
FIG. 4: is an example according to various embodiments illustrating a lipopeptaibol structure and a table indicating inhibitory effects for variations on the structure.
Figure 8:
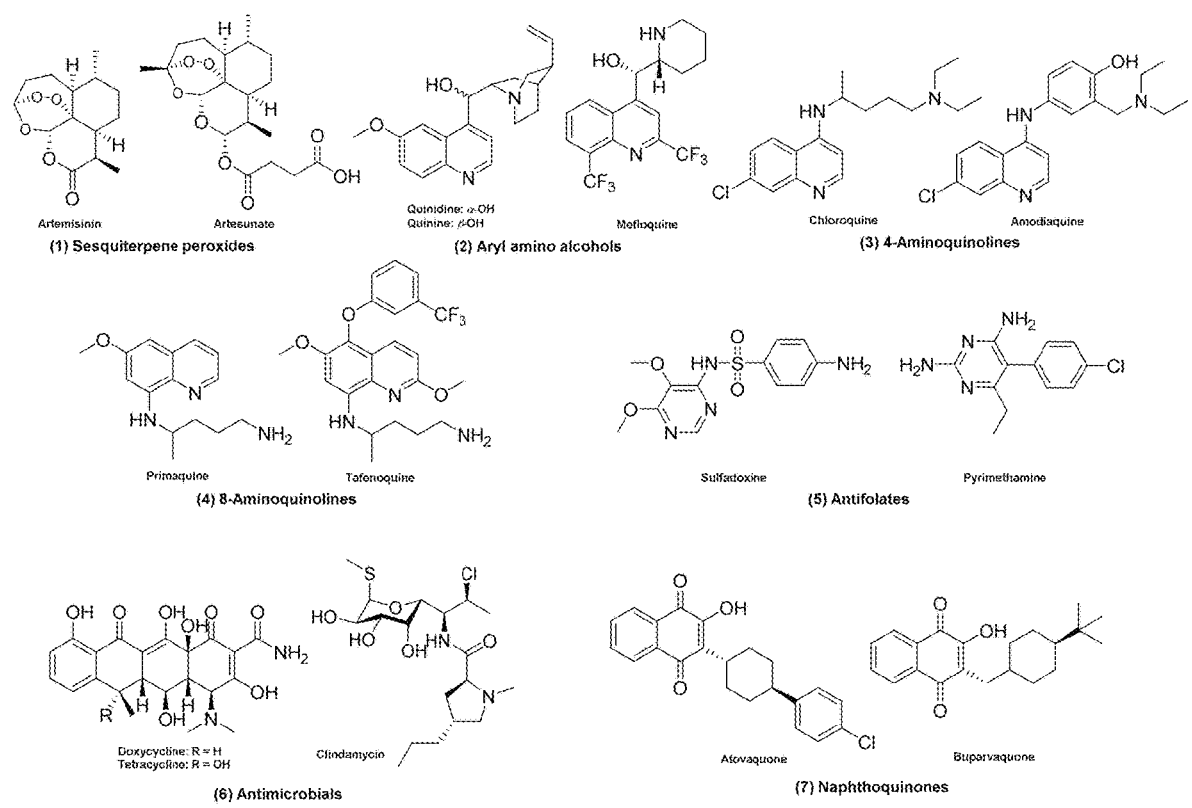
FIG. 8: illustrates a structural classification of prior art drugs being used clinically for the treatment of malaria.
Figure 9:
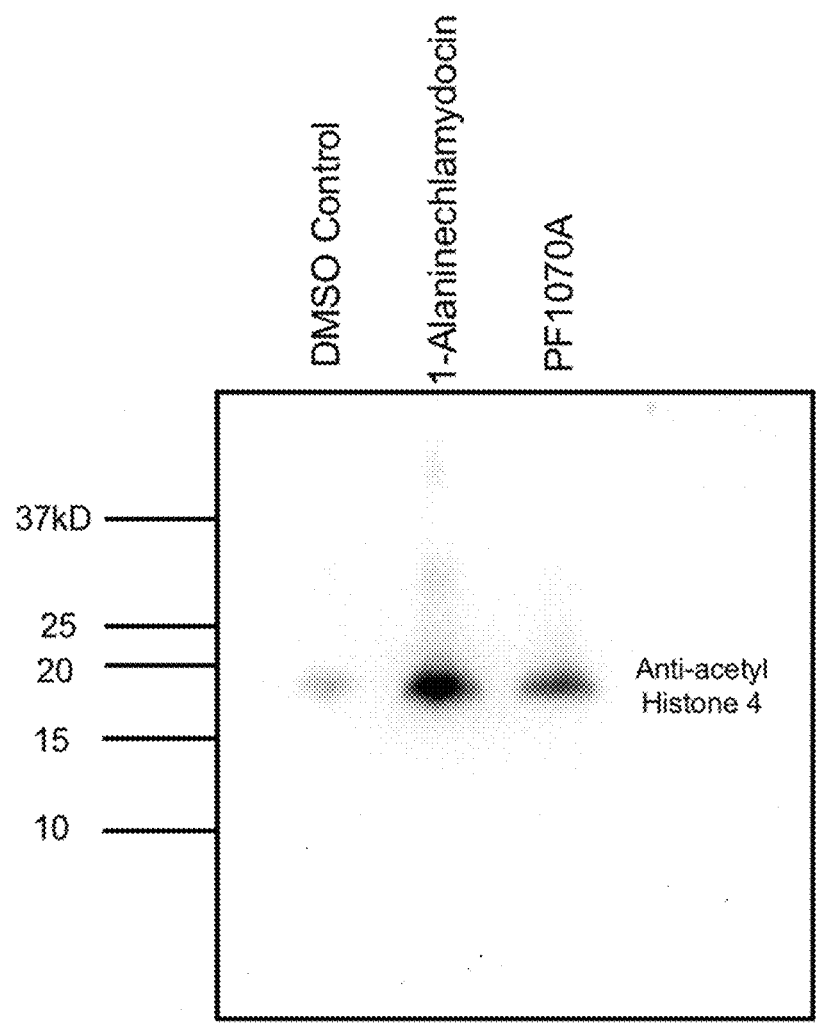
FIG. 9: is an example according to various embodiments, illustrating Chlamydocin Analogs 1-Alaninechlamydocin and PF107A causes hyperacetylation of Histone H4. Mixed stage culture was incubated with EC90 concentrations of 130134 Analog 2 and PF1070A for 4 hrs and cell free parasite extracts were subjected to western blot analysis using anti-acetyl histone 4 antibody.

FIG. 4-6 are examples according to various embodiments illustrating lipopeptaibol structures and a table indicating inhibitory effects for variations on the respective structure. Lipopeptaibols were also divided into three small groups depending on the number of amino acid residues, 7-AA lipopeptaibols (28-30, Table 4 in FIG. 4), 11-AA lipopeptaibols (31-36 and 44-45, Table 5 in FIG. 5), and 15-AA lipopeptaibols (37-43 and 46, Table 6 in FIG. 6).

Additional enumerated agents are provided in Table 8:

TABLE 8

Top Hits Identified from Pure Compound Library

| Structure | Library Code | Name | $EC_{50}$ (nM) | Selectivity Index |
|---|---|---|---|---|
| 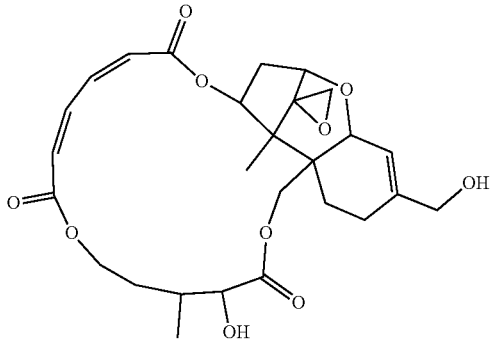 | 120090 | N/A | 4.02 | Pending, possibly 16.3 but need to repeat at a lower concentration |
| 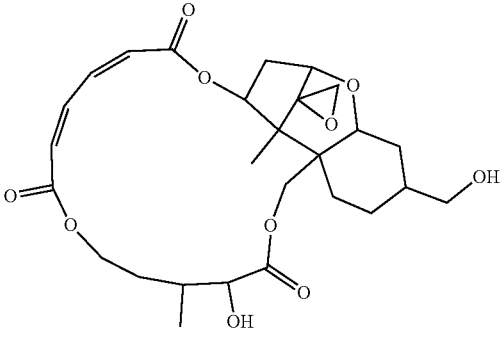 | 120091 | N/A | 55 | 66.17 |
| 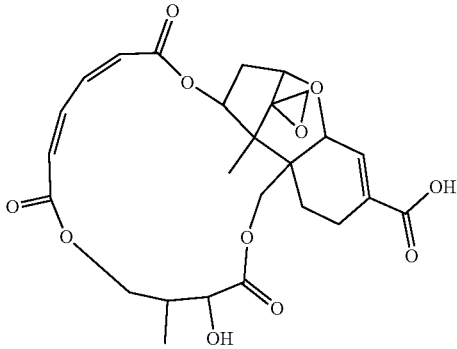 | 120089 | N/A | 59 | 85.22 |

TABLE 8-continued

Top Hits Identified from Pure Compound Library

| Structure | Library Code | Name | EC$_{50}$ (nM) | Selectivity Index |
|---|---|---|---|---|
| 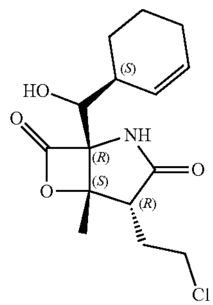 | 120066 | N/A | 47 | 290.28 |
| 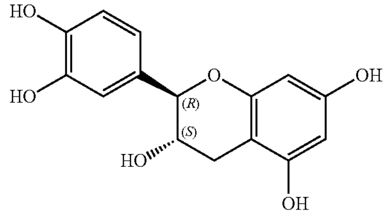 | 120051 | N/A | 47 | 11.44 |
| 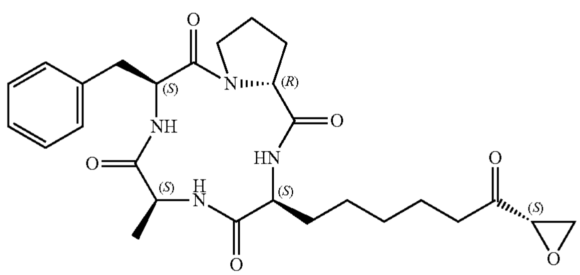 | 130134 | Chlamydocin | 24.7 | 7 |
| 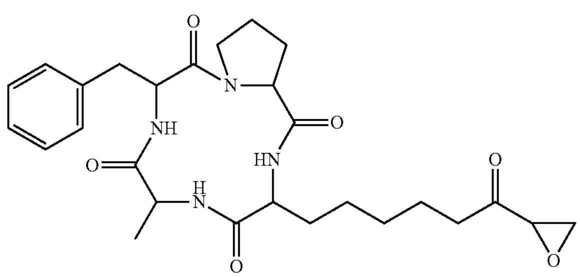 [SMILES: CC1NC(=O)C(CCCCCC(=O)C2CO2)NC(=O)C2CCCN2C(=O)C(Cc2ccccc2)NC1=O] | 130134 Analog 1 | 1-Alanine-chlamydocin | 9 | 3 |
| 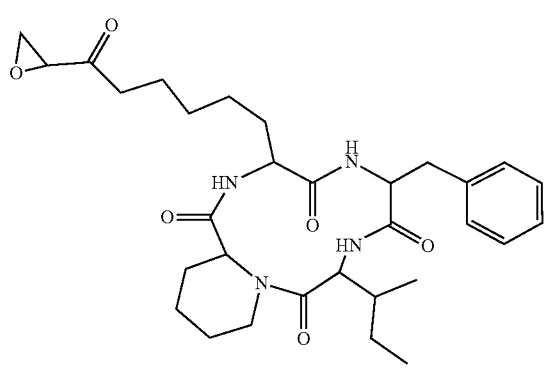 [SMILES: CCC(C)C1NC(=O)C(Cc2ccccc2)NC(=O)C(CCCCCC(=O)C2CO2)NC(=O)C2CCCCN2C1=O] | 130134 Analog 2 | PF1070A | 37 | >23 |

TABLE 8-continued

Top Hits Identified from Pure Compound Library

| Structure | Library Code | Name | EC$_{50}$ (nM) | Selectivity Index |
|---|---|---|---|---|
| 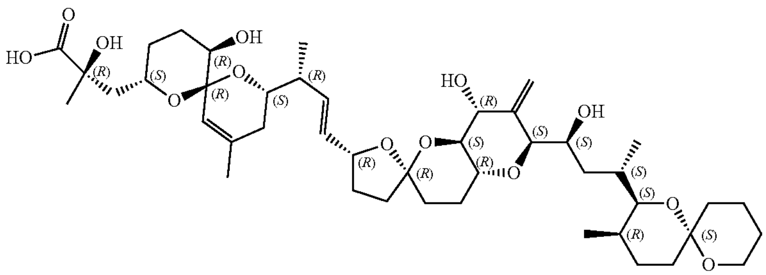 | 120033 | N/A | 55 | >77 |
| 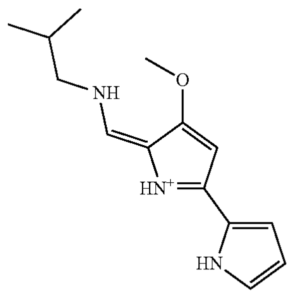 [SMILES: COC1=CC(c2ccc[nH]2)=[NH+]/C1=C/NCC(C)C] | 120036 | N/A | 180.33 | 57.31 |
| 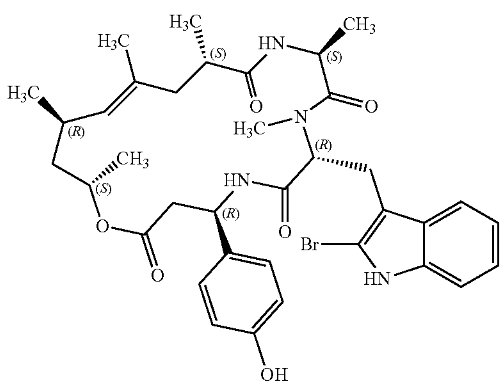 | 120030 | N/A | 271 | >92.25 |
| 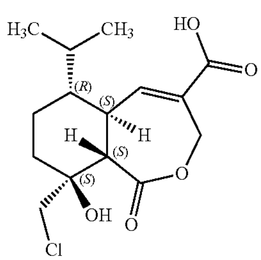 | 130129 | N/A | 361 | 3 |
| 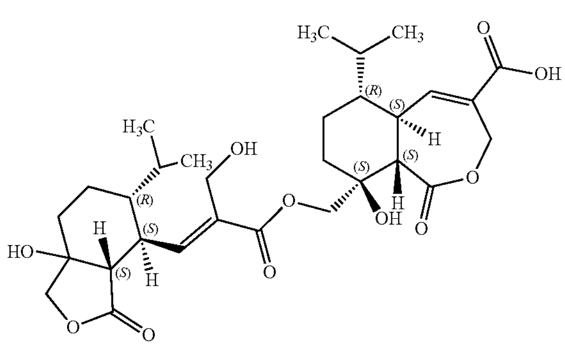 | 130131 | N/A | 367 | >54 |

TABLE 8-continued

Top Hits Identified from Pure Compound Library

| Structure | Library Code | Name | EC$_{50}$ (nM) | Selectivity Index |
|---|---|---|---|---|
| (structure) | 130115 | N/A | 491 | >32 |
| (structure) | 130130 | N/A | 469 | 3 |
| (structure) | 120086 | N/A | 361 | 14.62 |

Enumerated agents may also include those according to the following formula:

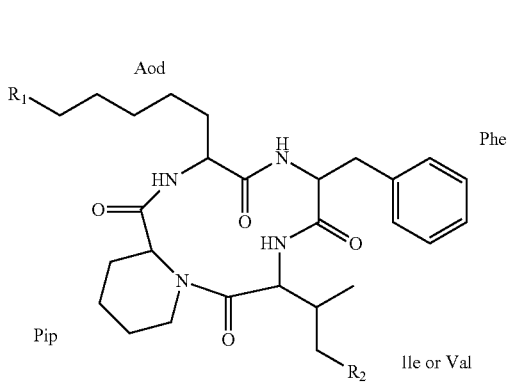

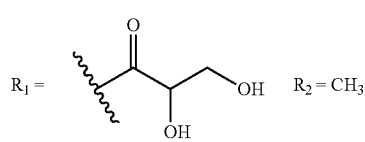

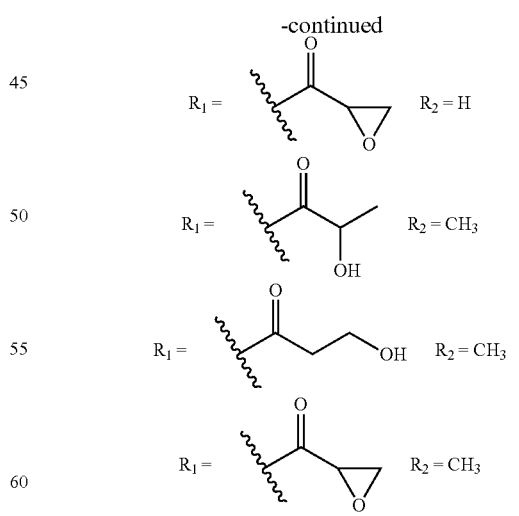

Other enumerated agents include a peptide containing α-aminoisobutyric acid and ending in an alcohol.

As used herein, "derivative" refers to a compound derived or obtained from another and containing essential elements of the parent compound. In one aspect, such a derivative possesses at least the same or similar therapeutic efficacy as the parent compound.

As used herein, by the term "effective amount" "amount effective," or the like, it is meant an amount effective at dosages and for periods of time necessary to achieve the desired result.

As used herein, the term "malaria" refers to an infectious disease spread by mosquitoes and caused by parasites of the genus *Plasmodium*.

As used herein, the term "parasite" refers to microorganisms that generally exploit the resources of its host body. Parasites may show a high degree of specialization and reproduce faster than their host. Parasites may also kill or reduce the biological mechanisms of the hosts.

As used herein, the term "pharmaceutically acceptable salt" is intended to include nontoxic base addition salts. Suitable salts include those derived from organic and inorganic acids such as, without limitation, hydrochloric acid, hydrobromic acid, phosphoric acid, sulfuric acid, methanesulfonic acid, acetic acid, tartaric acid, lactic acid, sulfinic acid, citric acid, maleic acid, fumaric acid, sorbic acid, aconitic acid, salicylic acid, phthalic acid, and the like. The term "pharmaceutically acceptable salt" as used herein is also intended to include salts of acidic groups, such as a carboxylate, with such counterions as ammonium, alkali metal salts, particularly sodium or potassium, alkaline earth metal salts, particularly calcium or magnesium, and salts with suitable organic bases such as lower alkylamines (methylamine, ethylamine, cyclohexylamine, and the like) or with substituted lower alkylamines (e.g. hydroxyl-substituted alkylamines such as diethanolamine, triethanolamine or tris(hydroxymethyl)-aminomethane), or with bases such as piperidine or morpholine.

As used herein, the term "preventing" means causing the clinical symptoms of the disease state not to worsen or develop, e.g., inhibiting the onset of disease, in a subject that may be exposed to or predisposed to the disease state, but does not yet experience or display symptoms of the full disease state, e.g., malaria.

As used herein, the term "prodrug" refers to a compound that is converted to a therapeutically active compound after administration, and the term should be interpreted as broadly herein as is generally understood in the art. Generally, but not necessarily, a prodrug is inactive or less active than the therapeutically active compound to which it is converted.

As used herein, the term "stereoisomer" refers to a compound which has the identical chemical constitution but differs with regard to the arrangement of the atoms or groups in space.

As used herein, the term "subject" refers to any animal (e.g., a mammal), including, but not limited to, humans, which may be the recipient of a particular treatment.

As used herein, the terms "treating" or "treatment" or "alleviation" refers to both therapeutic treatment and prophylactic or preventative measures, wherein the objective is to prevent or slow down (lessen) the targeted pathologic condition or disorder.

Derivatives

According to certain embodiments, as used herein, derivatives of enumerated agents include salts, esters, enol ethers, enol esters, acetals, ketals, orthoesters, hemiacetals, hemiketals, solvates, hydrates, metabolites or prodrugs thereof. Such derivatives may be readily prepared by those of skill in this art using known methods for such derivatization. The compounds produced may be administered to animals or humans without substantial toxic effects and either are pharmaceutically active or are prodrugs. Pharmaceutically acceptable salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethyl-benzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates. Pharmaceutically acceptable esters include, but are not limited to, alkyl, alkenyl, alkynyl, alk(en)(yn)yl, aryl, aralkyl, and cycloalkyl esters of acidic groups, including, but not limited to, carboxylic acids, phosphoric acids, phosphinic acids, sulfonic acids, sulfinic acids and boronic acids. Pharmaceutically acceptable enol ethers include, but are not limited to, derivatives of formula C=C(OR) where R is hydrogen, alkyl, alkenyl, alkynyl, alk(en)(yn)yl, aryl, aralkyl, or cycloalkyl. Pharmaceutically acceptable enol esters include, but are not limited to, derivatives of formula C=C(OC(O)R) where R is hydrogen, alkyl, alkenyl, alkynyl, aryl, aralkyl, or cycloalkyl. Pharmaceutically acceptable solvates and hydrates are complexes of a compound with one or more solvent or water molecules, or 1 to about 100, or 1 to about 10, or one to about 2, 3 or 4, solvent or water molecules.

According to further embodiments, derivatives may include, but are not limited to, specific substitutions of reactive constituents on or emanating from an enumerated agent, and may include, but are not limited to, one or more of the following: a hydrogen, hydroxy, halo, haloalkyl, thiocarbonyl, alkoxy, alkenoxy, alkylaryloxy, aryloxy, arylalkyloxy, cyano, nitro, imino, alkylamino, aminoalkyl, thio, sulfhydryl, thioalkyl, alkylthio, sulfonyl, C1-C6 straight or branched chain alkyl, C2-C6 straight or branched chain alkenyl or alkynyl, aryl, aralkyl, heteroaryl, carbocycle, or heterocycle group or moiety, or CO2 R7 where R7 is hydrogen or C1-C9 straight or branched chain alkyl or C2-C9 straight or branched chain alkenyl group or moiety. In a particular embodiment, a derivative of an enumerated agent is modified to include

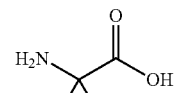

α-aminoisobutyric acid (AIB)

It is to be understood that the compounds provided herein may contain chiral centers. Such chiral centers may be of either the (R) or (S) configuration, or may be a mixture thereof. Thus, the compounds provided herein may be enantiomerically pure, or be stereoisomeric or diastereomeric mixtures. It is to be understood that the chiral centers of the compounds provided herein may undergo epimerization in vivo. As such, one of skill in the art will recognize that administration of a compound in its (R) form is equivalent, for compounds that undergo epimerization in vivo, to administration of the compound in its (S) form.

As used herein, alkyl refers to an unbranched or branched hydrocarbon chain. An alkyl group may be unsubstituted or substituted with one or more heteroatoms.

As used herein, alkenyl refers to an unbranched or branched hydrocarbon chain comprising one or more double bonds. The double bond of an alkenyl group may be unconjugated or conjugated to another unsaturated group. An alkenyl group may be unsubstituted or substituted with one or more heteroatoms.

As used herein, alkynyl refers to an unbranched or branched hydrocarbon chain comprising one of more triple bonds therein. The triple bond of an alkynyl group may be unconjugated or conjugated to another unsaturated group. An alkynyl group may be unsubstituted or substituted with one or more heteroatoms.

As used herein, alk(en)(yn)yl refers to an unbranched or branched hydrocarbon group comprising at least one double bond and at least one triple bond. The double bond or triple bond of an alk(en)(yn)yl group may be unconjugated or conjugated to another unsaturated group. An alk(en)(yn)yl group may be unsubstituted or substituted with one or more heteroatoms.

Exemplary alkyl, alkenyl, alkynyl, and alk(en)(yn)yl groups herein include, but are not limited to, methyl, ethyl, propyl, isopropyl, isobutyl, n-butyl, sec-butyl, tert-butyl, isopentyl, neopentyl, tert-pentyl, isohexyl, allyl (propenyl) and propargyl (propynyl).

As used herein, "aryl" refers to aromatic monocyclic or multicyclic groups containing from 6 to 19 carbon atoms. Aryl groups include, but are not limited to groups such as unsubstituted or substituted fluorenyl, unsubstituted or substituted phenyl, and unsubstituted or substituted naphthyl.

As used herein, "heteroaryl" refers to a monocyclic or multicyclic aromatic ring system, in certain embodiments, of about 5 to about 15 members where one or more, in one embodiment 1 to 3, of the atoms in the ring system is a heteroatom, that is, an element other than carbon, including but not limited to, nitrogen, oxygen or sulfur. The heteroaryl group may be optionally fused to a benzene ring. Heteroaryl groups include, but are not limited to, furyl, imidazolyl, pyrimidinyl, tetrazolyl, thienyl, pyridyl, pyrrolyl, thiazolyl, isothiazolyl, oxazolyl, isoxazolyl, triazolyl, quinolinyl or isoquinolinyl.

As used herein, "halo," "halogen," or "halide" refers to F, Cl, Br or I.

As used herein, base refers to any compound that accepts protons in water or solvent. Thus, exemplary bases include, but are not limited to, alkali metal hydroxides and alkali metal alkoxides (i.e., MOR, wherein M is an alkali metal such as but not limited to potassium, lithium, or sodium and R is hydrogen, alkyl, alkenyl, alkynyl, or alk(en)(yn)yl) such as but not limited to potassium hydroxide, potassium tert-butoxide, potassium tert-pentoxide, sodium hydroxide, sodium tert-butoxide, lithium hydroxide, etc.); other hydroxides such as but not limited to magnesium hydroxide (Mg(OH)2), calcium hydroxide (Ca(OH)2), or barium hydroxide (Ba(OH)2); alkali metal hydrides (i.e., MH, wherein M is as defined above) such as but not limited to sodium hydride, potassium hydride, or lithium hydride; carbonates such as but not limited to potassium carbonate (K2CO3), sodium carbonate (Na2CO3), potassium bicarbonate (KHCO3), or sodium bicarbonate (NaHCO3); alkyl ammonium hydroxides, alkenyl ammonium hydroxides, alkynyl ammonium hydroxides, or alk(en)(yn)yl ammonium hydroxides such as but not limited to n-tetrabutyl ammonium hydroxide (TBAH); amines such as ammonia, diethylamine, 2,2,6,6-tetramethyl piperidine (HTMP), tertiary amines (such as but not limited to dimethylethyl amine, diisopropylethylamine, trimethylamine, triethylamine, tributylamine, N-methylmorpholine, N-methylpyrrolidine, 1,8-diazabicyclo[5.4.0]-7-undecene (DBU), 1,5-diazabicyclo[4.3.0]-5-nonene (DBN), or tetramethylenediamine (TMEDA)), aromatic amines (such as but not limited to pyridine, collidine, lutidine, picoline, quinoline, or N,N-dimethylaniline); alkali metal amides such as but not limited to lithium amide, lithium dimethylamide, lithium diisopropylamide (LDA), lithium tetramethylpiperidide (LiTMP), or alkali metal hexamethyldisilazanes (such as but not limited to potassium hexamethyldisilazane, (KHMDS), sodium hexamethyldisilazane (NaHMDS), or lithium hexamethyldisilazane (LiHMDS)); alkyl lithiums, alkenyl lithiums, alkynyl lithiums, or alk(en)(yn)yl lithiums such as but not limited to n-butyl lithium sec-butyllithium, isopropyllithium; alkyl magnesium halides, alkenyl magnesium halides, alkynyl magnesium halides, or alk(en)(yn)yl magnesium halides such as but not limited to methyl magnesium bromide.

As used herein, solvent refers to any liquid that completely or partially dissolves a solid, liquid, or gaseous solute, resulting in a solution such as but not limited to hexane, benzene, toluene, diethyl ether, chloroform, ethyl acetate, dichloromethane, carbon tetrachloride, 1,4-dioxane, tetrahydrofuran, glyme, diglyme, acetone, acetonitrile, dimethylformamide, dimethyl sulfoxide, dimethylacetamide, or N-methyl-2-pyrrolidone.

As used herein, dehydrating agent refers to any compound that promotes the formation of carboxamides from carboxylic acids, such as but not limited to thionyl chloride, sulfuryl chloride, a carbodiimide, an anhydride or a mixed anhydride, a phenol (such as but not limited to nitrophenol, pentafluorophenol, or phenol), or a compound of Formula (A):

(A)

wherein each of X and Y is independently an unsubstituted or substituted heteroaryl group (such as but not limited to imidazolyl, benzimidazolyl, or benzotriazolyl). Examples of dehydrating agents further include, but are not limited to, benzotriazole-1-yl-oxy-tris-(dimethylamino)-phosphonium hexafluorophosphate (BOP), N,N'-carbonyldiimidazole (CDI), 3-(diethoxyphosphoryloxy)-1,2,3-benzotriazin-4(3H)-one (DEPBT), 1-ethyl-3-(3-dimethylaminopropyl) carbodiimide (EDC), 2-(7-aza-1H-benzotriazole-1-yl)-1,1,3,3-tetramethyluronium hexafluorophosphate (HATU), 2-(1H-benzotriazole-1-yl)-1,1,3,3-tetramethyluronium hexafluorophosphate (HBTU), 1-hydroxybenzotriazole (HOBt), benzotriazole-1-yl-oxy-tris-pyrrolidino-phosphonium hexafluorophosphate (PyBOP), 2-(1H-benzotriazole-1-yl)-1,1,3,3-tetramethyluronium tetrafluoroborate (TBTU), O-(3,4-dihydro-4-oxo-1,2,3-benzotriazine-3-yl)-N,N,N,N-tetra methyluronium tetrafluoroborate (TDBTU), 3-(diethyloxyphosphoryloxy)-1,2,3-benzotriazin-4(3H)-one (DEPBT), dicyclohexylcarbodiimide (DCC), N,N'-diisopropylcarbodiimide (DIC), or 1-hydroxy-7-azabenzotriazole (HOAt).

As used herein, acid refers to any compound that contains hydrogen and dissociates in water or solvent to produce positive hydrogen ions, as well as Lewis acids, including but not limited to hydrochloric acid, sulfuric acid, phosphoric acid, acetic acid, trihaloacetic acids (such as but not limited to trifluoroacetic acid or trichloroacetic acid), hydrogen bromide, maleic acid, sulfonic acids (such as but not limited to toluenesulfonic acids or camphorsulfonic acids), propionic acids (such as but not limited to (R)-chloropropionic acid), phthalamic acids (such as but not limited to N—[(R)-1-(1-naphthyl)ethyl]phthalamic acid), tartaric acids (such as but not limited to L-tartaric acid or dibenzyl-L-tartaric acid), lactic acids, camphoric acids, aspartic acids, or citronellic acids.

It is to be understood that reactants, compounds, solvents, acids, bases, catalysts, agents, reactive groups, or the like may be added individually, simultaneously, separately, and in any order. Furthermore, it is to be understood that reactants, compounds, acids, bases, catalysts, agents, reactive groups, or the like may be pre-dissolved in solution and added as a solution (including, but not limited to, aqueous solutions). In addition, it is to be understood that reactants, compounds, solvents, acids, bases, catalysts, agents, reactive groups, or the like may be in any molar ratio.

It is to be understood that reactants, compounds, solvents, acids, bases, catalysts, agents, reactive groups, or the like may be formed in situ.

Enantiomers/Tautomers

Enumerated agents of the disclosure also include where appropriate all enantiomers and tautomers of the agents. One skilled in the art will recognize compounds that possess optical properties (one or more chiral carbon atoms) or tautomeric characteristics. The corresponding enantiomers and/or tautomers may be isolated/prepared by methods known in the art.

Stereo and Geometric Isomers

Enumerated agents of the disclosure may exist as stereoisomers and/or geometric isomers—e.g. they may possess one or more asymmetric and/or geometric centres and so may exist in two or more stereoisomeric and/or geometric forms. Contemplated herein is the use of all the individual stereoisomers and geometric isomers of those inhibitor agents, and mixtures thereof. The terms used in the claims encompass these forms, provided said forms retain the appropriate functional activity (though not necessarily to the same degree).

Anti-malarial agents of the disclosure also include all suitable isotopic variations of the agent or pharmaceutically acceptable salts thereof. An isotopic variation of an anti-malarial agent or a pharmaceutically acceptable salt thereof is defined as one in which at least one atom is replaced by an atom having the same atomic number but an atomic mass different from the atomic mass usually found in nature. Examples of isotopes that can be incorporated into the agent and pharmaceutically acceptable salts thereof include isotopes of hydrogen, carbon, nitrogen, oxygen, phosphorus, sulphur, fluorine and chlorine such as 2H, 3H, 13C, 14C, 15N, 17O, 18O, 31P, 32P, 35S, 18F and 36Cl, respectively. Certain isotopic variations of the agent and pharmaceutically acceptable salts thereof, for example, those in which a radioactive isotope such as 3H or 14C is incorporated, are useful in drug and/or substrate tissue distribution studies. Tritiated, i.e., 3H, and carbon-14, i.e., 14C, isotopes are particularly preferred for their ease of preparation and detectability. Further, substitution with isotopes such as deuterium, i.e., 2H, may afford certain therapeutic advantages resulting from greater metabolic stability, for example, increased in vivo half-life or reduced dosage requirements and hence may be preferred in some circumstances. Isotopic variations of the anti-malarial agents and pharmaceutically acceptable salts thereof of this disclosure can generally be prepared by conventional procedures using appropriate isotopic variations of suitable reagents.

Solvates

The enumerated agents of the disclosure also include solvate forms of the agents. The terms used in the claims encompass these forms.

Polymorphs

The enumerated agents of the present disclosure also include their various crystalline forms, polymorphic forms and (an)hydrous forms. It is well established within the pharmaceutical industry that chemical compounds may be isolated in any of such forms by slightly varying the method of purification and or isolation form the solvents used in the synthetic preparation of such compounds.

Prodrugs

Embodiments of the disclosure further include enumerated agents of the disclosure in prodrug form. Such prodrugs are generally compounds wherein one or more appropriate groups have been modified such that the modification may be reversed upon administration to a human or mammalian subject. Such reversion is usually performed by an enzyme naturally present in such subject, though it is possible for a second agent to be administered together with such a prodrug in order to perform the reversion in vivo. Examples of such modifications include ester (for example, any of those described above), wherein the reversion may be carried out be an esterase etc. Other such systems will be well known to those skilled in the art.

Metabolites

Also falling within the scope of this disclosure are the in vivo metabolic products of the enumerated agents of the disclosure. A "metabolite" is a pharmacologically active product produced through metabolism in the body of a specified compound or salt thereof. Such products can result, for example, from the oxidation, reduction, hydrolysis, amidation, deamidation, esterification, deesterification, enzymatic cleavage, and the like, of the administered compound. Accordingly, the embodiments include metabolites of enumerated agents including compounds produced by a process comprising contacting an enumerated agent of this described herein with a mammal for a period of time sufficient to yield a metabolic product thereof.

Metabolites are identified, for example, by preparing a radiolabelled (e.g., $^{14}C$ or $^{3}H$) isotope of an enumerated agent described herein, administering it parenterally in a detectable dose (e.g., greater than about 0.5 mg/kg) to an animal such as rat, mouse, guinea pig, monkey, or to a human, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolites, so long as they are not otherwise found in vivo, are useful in diagnostic assays for therapeutic dosing of the enumerated agent compounds described herein.

According to certain embodiments, provided are methods of preventing or treating malaria in a subject or preventing or treating a subject exhibiting a symptom of malaria. Malaria typically produces a string of recurrent attacks, or paroxysms, each of which has three stages—chills, followed by fever, and then sweating. Along with chills, the person is likely to have headache, malaise, fatigue, muscular pains, occasional nausea, vomiting, and diarrhea. Within an hour or two, the body temperature rises, and the skin feels hot and dry. Then, as the body temperature falls, a drenching sweat begins. The person, feeling tired and weak, is likely to fall asleep. A subject exhibiting one, two or more of the foregoing symptoms is considered a subject in need.

Pharmaceutical Compositions

Aspects also provide pharmaceutical compositions comprising one or more enumerated agents as are described herein. Enumerated agents(s) can be administered to a patient to achieve a therapeutic effect, e.g., active against parasites of malaria and in turn, treating and/or preventing malaria. Pharmaceutical composition embodiments including an enumerated agent can comprise, for example, compounds in any of Tables 1-12. In certain embodiments, the active agents were identified by a screening method embodiment described herein, which were identified by their activity against *P. falciparum* Dd2 using a SYBR Green I-based fluorescence assay. The compositions can be administered alone or in combination with at least one other agent, such as a stabilizing compound, which can be administered in any sterile, biocompatible pharmaceutical carrier, including, but not limited to, saline, buffered saline, dextrose, and water. The compositions can be administered to a subject alone, or in combination with other therapeutic agents or treatments as described below.

In addition to the active ingredients, these pharmaceutical compositions can contain suitable pharmaceutically acceptable carriers comprising excipients and auxiliaries that facilitate processing of the active compounds into preparations which can be used pharmaceutically. Pharmaceutical composition embodiments can be administered by any number of routes including, but not limited to, oral, intravenous, intramuscular, intra-arterial, intramedullary, intrathecal, intraventricular, transdermal, subcutaneous, intraperitoneal, intranasal, parenteral, topical, sublingual, or rectal means. Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the subject.

Further details on techniques for formulation and administration can be found in the latest edition of REMINGTON'S PHARMACEUTICAL SCIENCES (Maack Publishing Co., Easton, Pa., which is incorporated herein by reference). After pharmaceutical compositions have been prepared, they can be placed in an appropriate container and labeled for treatment of an indicated condition. Such labeling would include amount, frequency, and method of administration.

Determination of a Therapeutically Effective Dose

The determination of a therapeutically effective dose of enumerated agents identified by a screening method herein is well within the capability of those skilled in the art. A therapeutically effective dose refers to that amount of active ingredient which shows activity against malarial parasites. One example is if activities of $IC_{50}$ of <10 µg/ml against *P. falciparum* 3D7 using malaria parasite growth inhibition assays. Therapeutic efficacy and toxicity, e.g., $ED_{50}$ (the dose therapeutically effective in 50% of the population) and LD50 (the dose lethal to 50% of the population), can be determined by standard pharmaceutical procedures in cell cultures or experimental animals. The dose ratio of toxic to therapeutic effects is the therapeutic index, and it can be expressed as the ratio, $LD_{50}/ED_{50}$.

The exact dosage will be determined by the practitioner, in light of factors related to the subject that requires treatment. Dosage and administration are adjusted to provide sufficient levels of the active ingredient or to maintain the desired effect. Factors which can be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions can be administered every 3 to 4 days, every week, or once every two weeks depending on the half-life and clearance rate of the particular formulation.

Normal dosage amounts can vary from 0.1 to 100,000 micrograms, up to a total dose of about 1 g, depending upon the route of administration. Guidance as to particular dosages and methods of delivery is provided in the literature and generally available to practitioners in the art. Preferably, a therapeutic agent gains access to the parasite or the infected red blood cell for the duration of time necessary for its normal action.

Screening

One embodiment for screening for compounds having activity against malaria includes the SYBR Green I Assay described as follows:

SYBR Green-I Fluorescence Assay

Ten millimolar compound stocks in DMSO were diluted by 1/2, 1/5, and/or 1/10 fold dilutions in ultrapure water or RPMI 1640. Varying concentrations of compound were added to culture at a 1% parasitemia and 2% hematocrit in 96-well black plates. Assay conditions maintained maximum DMSO concentrations less than 0.125% per dilution. Positive (baseline 0% growth) controls consisted of Chloroquine at 1 µM final concentration. Following 72 h incubation at 37° C. in 5% $CO_2$, dilution plates were frozen at −80° C. for a minimum of 30 minutes. Dilution plates were allowed to thaw followed by lysis treatment and SYBR Green I incorporation. DNA quantification was determined using a fluorescence reading on a Synergy H4 multimode plate reader set at 485 nm excitation and 530 nm emission as previously reported (*Roberts*, Iyamu et al. 2016). $EC_{50}$ was calculated from a dose response curve that was generated from a concentration range of 0-10 µM using GraphPad Prism v5.0.

Different dilutions of the compound/fraction in 1 µl of the culture medium were added to 99 µl of *P. falciparum* culture at a 1% parasitemia and 2% hematocrit in 96-well plates. Maximum DMSO concentration in the culture never exceeded 0.125%. Chloroquine at 1 µM was used as a positive control to determine the baseline value. Following 72 hours incubation at 37° C., the plates were frozen at −80° C. After thawing, 100 µL of lysis buffer (with SYBR Green I dye 1:10,000) was added to each well and plates were incubated at room temperature for 30 minutes prior to reading.

Symptoms

The enumerated agents and compositions as described herein may be utilized for the treatment or prevention of one or more symptoms of malaria. The signs and symptoms of malaria often begin 8-25 days following infection but may occur later in those who have taken anti-malarial medications as prevention. Symptoms may include but are not limited to fever, shivering, arthralgia (joint pain), vomiting, hemolytic anemia, jaundice, hemoglobinuria, retinal damage, e.g., retinal whitening, abnormal posture, and convulsions. The classic symptoms of malaria include the cyclical occurrence of sudden coldness, rigor, fever and sweating lasting about two hours or more, occurring every 2-4 days. In some cases, the fever may be continuous. Severe symptoms, which are more likely in the case of *P. falciparum* infection, include splenomegaly (enlarged spleen), severe headache, cerebral ischemia, hepatomegaly (enlarged liver), hypoglycemia, and hemoglobinuria with renal failure.

Conjunctive Therapeutic Agents

In any of the embodiments described above, any of the compound and/or composition embodiments can be co-administered with other appropriate therapeutic agents (conjunctive agent or conjunctive therapeutic agent) or therapies for the treatment or prevention of malaria and/or a symptom thereof. The term "co-administered" or "co-administration" or "co-administers" as used herein means administration of an active agent before, concurrently, or after the administration of another active agent such that the biological effects of either agents overlap. The combination of agents as taught herein can act synergistically to treat or prevent the various diseases, disorders or conditions described herein. Using this approach, one may be able to achieve therapeutic efficacy with lower dosages of each agent, thus reducing the potential for adverse side effects.

Selection of the appropriate conjunctive agents or therapies for use in combination therapy can be made by one of ordinary skill in the art, according to conventional pharmaceutical principles. The combination of therapeutic agents or therapies can act synergistically to effect the treatment or prevention of malaria or a symptom thereof. Using this approach, one may be able to achieve therapeutic efficacy with lower dosages of each agent, thus reducing the potential for adverse side effects.

Exemplary conjunctive agents that may be formulated and/or administered with a compound as described herein include, but are not limited to chloroquine (Aralen), quinine, tetracycline, clindamycin (Cleocin), mefloquin (Lariam), sulfadoxone/pyrimethamine (Fansidar), primaquine and halofantrine. It is appreciated that suitable conjuvant therapeutic agents may also comprise any combinations, prodrugs, pharmaceutically acceptable salts, analogs, and derivatives thereof.

The mode of administration for a conjunctive formulation in accordance with the teachings herein is not particularly limited, provided that the one or more enumerated agents as described herein and the conjunctive agent are combined upon administration. Such an administration mode may, for example, be (1) an administration of a single formulation obtained by formulating an enumerated agent and a conjunctive agent simultaneously; (2) a simultaneous administration via an identical route of the two agents obtained by formulating an enumerated agent and a conjunctive agent separately; (3) a sequential and intermittent administration via an identical route of the two agents obtained by formulating an enumerated agent and a conjunctive agent separately; (4) a simultaneous administration via different routes of two formulations obtained by formulating an enumerated agent and a conjunctive agent separately; and/or (5) a sequential and intermittent administration via different routes of two formulations obtained by formulating an enumerated agent and a conjunctive agent separately (for example, an enumerated agent followed by a conjunctive agent, or inverse order) and the like.

The dose of a conjunctive formulation may vary depending on the formulation of the novel anti-malarial agent and/or the conjunctive agent, the subject's age, body weight, condition, and the dosage form as well as administration mode and duration. One skilled in the art would readily appreciate that the dose may vary depending on various factors as described above, and a less amount may sometimes be sufficient and an excessive amount should sometimes be required.

The conjunctive agent may be employed in any amount within the range causing no problematic side effects. The daily dose of a conjunctive agent is not limited particularly and may vary depending on the severity of the disease, the subject's age, sex, body weight and susceptibility as well as time and interval of the administration and the characteristics, preparation, type and active ingredient of the pharmaceutical formulation. An exemplary daily oral dose per kg body weight in a subject, e.g., a mammal, is about 0.001 to 2000 mg, preferably about 0.01 to 500 mg, more preferably about 0.1 to about 100 mg as medicaments, which is given usually in 1 to 4 portions.

When the enumerated agent and a conjunctive agent are administered to a subject, the agents may be administered at the same time, but it is also possible that a conjunctive agent is first administered and then an enumerated agent is administered, or that an enumerated agent is first administered and then a conjunctive agent is administered. When such an intermittent administration is employed, the time interval may vary depending on the active ingredient administered, the dosage form and the administration mode, and for example, when a conjunctive agent is first administered, an enumerated agent may be administered within 1 minute to 3 days, preferably 10 minutes to 1 day, more preferably 15 minutes to 1 hour after the administration of the conjunctive agent. When an enumerated agent is first administered, for example, then a conjunctive agent may be administered within 1 minute to 1 day, preferably 10 minutes to 6 hours, more preferably 15 minutes to 1 hour after the administration of a novel anti-malarial agent.

It is understood that when referring to an enumerated agent and a conjunctive agent, it is meant an enumerated agent alone, a conjunctive agent alone, as a part of a composition, e.g., composition, which optionally includes one or more pharmaceutical carriers. It is also contemplated that more than one conjunctive agent may be administered to the subject if desired.

EXAMPLES

Introduction

The following examples are put forth to provide those of ordinary skill in the art with a complete disclosure and description of how to perform the methods, how to make, and how to use the compositions and compounds disclosed and claimed herein. Efforts have been made to ensure accuracy with respect to numbers (e.g., amounts, temperature, etc.), but some errors and deviations should be accounted for.

The purpose of the following examples is not to limit the scope of the various embodiments, but merely to provide examples illustrating specific embodiments.

We decided to look into our fungal extract library made by Natural Products Discovery Group of the University of Oklahoma. In the course of our screening of the crude extracts of collected fungi for antimalarial activity, *Trichoderma harzianum* and *Hypocrea pachybasioides*, which are well-known for their production of various non-ribosomal peptides, were selected for chemical investigation to discover potent antimalarial peptaibols.

The bioassay-guided investigation of the EtOAc crude extract afforded 30 new peptaibols (1-14 and 28-43), along with 22 known compounds (15-27 and 44-52). Some literature described the structure elucidation of the reported peptaibols using only mass spectrometry. So, they just assigned amino acid residues in the peptaibols judging by their molecular weight. In other words, isomeric (Leu vs Ile vs alto-Ile, and Iva vs Val) and absolute (L-form vs D-form) configuration of amino acid residues were not exactly assigned often. For instance, in several papers Leu, Ile, Val and Iva were assigned as 'Lxx' or 'Vxx', because they just determined those reported peptaibol sequences by LC-MS/MS fragmentation experiment. So, first, we focus on describing the structure elucidation of all new isolated peptaibols (1-14 and 28-43) from this fungus using NMR experiments and chemical reactions, and then, we confirmed the predicted sequence by the MS/MS analysis. Also, we report their antimalarial activities, cytotoxicity, structure-activity relationship (SAR) of peptaibols we isolated.

According to various embodiments, thirty new peptaibols (1-14 and 28-43), along with 22 known compounds (15-27 and 44-52), were isolated from the bioactivity-guided fractionation of the ethyl acetate extract of *Trichoderma harzianum* and *Hypocrea pachybasioides*. Their absolute configurations were elucidated by a combination of spectroscopic data (1 D and 2D NMR, ECD, HRESIMS, and MS/MS analysis), and chemical methods (Marfey's and GITC methods). All isolates (1-52) were found to have antimalarial activity, with their $EC_{50}$ in the range of 0.29-3.66 μM and good selectivity index (SI) values.

More specifically, FIGS. 1-3 and 7 are examples according to various embodiments illustrating peptaibol structures and a table indicating inhibitory effects for variations on the respective structure. All isolated peptaibols (1-52) could be generally divided into two groups, acetyl-peptaibols (1-27 and 47-52) with the acetyl group at the N-terminal and lipopeptaibols (28-46) with the n-octanoyl moiety at the N-terminus. Acetyl-peptaibols were further divided into four small groups depending on the length of sequence, 18-AA peptaibols (1-5 and 15-19, Table 1 in FIG. 1), 14-AA peptaibols (6-13 and 20-26, Table 2 in FIG. 2), 11-AA peptaibols (14 and 27, Table 3 in FIG. 3), and 20-AA peptaibols (47-52, Table 7 in FIG. 7).

FIG. 4-6 are examples according to various embodiments illustrating lipopeptaibol structures and a table indicating inhibitory effects for variations on the respective structure. Lipopeptaibols were also divided into three small groups depending on the number of amino acid residues, 7-AA lipopeptaibols (28-30, Table 4 in FIG. 4), 11-AA lipopeptaibols (31-36 and 44-45, Table 5 in FIG. 5), and 15-AA lipopeptaibols (37-43 and 46, Table 6 in FIG. 6).

Examples 1-14

Examples 1-27 provide a structure elucidation of Peptaibols Isolated from *T. harzianum*.

Example 1

Compound 1 was obtained as a colorless solid and its molecular formula of $C_{79}H_{138}N_{20}O_{21}$ was determined from the HRESIMS data (m/z 852.5261 $[M+H]^{2+}$; calcd 852.5245). The $^1H$ NMR spectrum of 1 showed signals for amide protons in the range of $\delta_H$ 7 to 10 ppm and α-proton of amino acids in the range of $\delta_H$ 4 to 5 ppm, and the $^{13}C$ and HSQC NMR spectrum of 1 displayed the presence of 79 carbons signals including 20 amide carbonyls. The HSQC, HMBC and COSY spectrum of 1 revealed the identification of 18 amino acid residues including standard amino acids [two alanines (Ala), two glycines (Gly), two leucines (Leu), two glutamines (Gln), a valine (Val) and a proline (Pro)], and unusual amino acids [six α-aminoisobutyric acids (Aib), an isovaline (Iva), a leucinol (Leuol) at the C-terminal, and an acetyl group at the N-terminal], which were typically shown in the peptaibols generated by certain fungi such as the genus *Trichoderma*.[xi] The linear sequence of peptaibol 1 was determined by the HMBC correlations between amide carbons and amide protons, and ROESY correlations of α-protons as Ac-Aib$^1$-Gly$^2$-Ala$^3$-Aib$^4$-Ala$^5$-Gln$^6$-Aib$^7$-Val$^8$-Aib$^9$-Gly$^{10}$-Leu$^{11}$-Aib$^{12}$-Pro$^{13}$-Leu$^{14}$-Aib$^{15}$-Iva$^{16}$-Gln$^{17}$-Leuol$^{18}$. This sequence of 1 was also confirmed by the fragment ions analysis by the ESI-MS/MS spectrum, and it turned out to be similar to trichorzin HA I (15),[xii] which was reported that it was isolated from the same species, *T. harzianum*. Comparing with the sequence of 15, compound 1 carried Ala$^5$ and Iva$^{16}$ instead of two Aibs, and Ala, which was placed at the fifth amino acid site, was an unusual sequence among the series of trichorzin series peptaibols. The absolute configuration of every single amino acid of 1 was identified by performing Marfey's method.[xiii] Most of them were turned out to be L-form, which is (S), but only Iva was D-form, (R). Furthermore, the ECD spectrum of 1 showed a negative Cotton effect at 208 and 225 nm, which demonstrated the right-handed helical conformation of 1.[xiv] Thus, peptaibol 1 was established as Ac-Aib$^1$-Gly$^2$-$_L$-Ala$^3$-Aib$^4$-$_L$-Ala$^5$-$_L$-Gln$^6$-Aib$^7$-$_L$-Val$^8$-Aib$^9$-Gly$^{10}$-$_L$-Leu$^{11}$-Aib$^{12}$-$_L$-Pro$^{13}$-$_L$-Leu$^{14}$-Aib$^{15}$-D-Iva$^{16}$-$_L$-Gln$^{17}$-$_L$-Leuol$^{185}$, named trichorzin NP A (1).

Example 2

Compound 2 was isolated as a colorless solid, and the HRESIMS data were consistent with the molecular formula of $C_{79}H_{138}N_{19}O_{22}$ (m/z 853.0184 $[M+H]^{2+}$; calcd 853.0166). On the basis of the analysis of 1D and 2D NMR, the sequence of 2 was almost identical to trichorzin HA I (15),[xii] except for the presence of glutamic acid (Glu), instead of one of glutamines (Gln). The fragment ions analysis of 2 verified that Glu was located at the seventeenth position (Glu$^{17}$) comparing with those of 15. The absolute configurations of amino acids of 2 were confirmed by Marfey's method as Ac-Aib$^1$-Gly$^2$-$_L$-Ala$^3$-Aib$^4$-Aib$^5$-$_L$-Gln$^6$-Aib$^7$-$_L$-Val$^8$-Aib$^9$-Gly$^{10}$-$_L$-Leu$^{11}$-Aib$^{12}$-$_L$-Pro$^{13}$-$_L$-Leu$^{14}$-Aib$^{15}$-Aib$^{16}$-$_L$-Glu$^{17}$-$_L$-Leuol$^{18}$, named trichorzin NP B (2).

Example 3

Compound 3 was obtained as a colorless solid and showed a molecular formula of $C_{81}H_{142}N_{20}O_{21}$ as determined by its HRESIMS data (m/z 866.5419 $[M+H]^{2+}$; calcd 866.5402). The $^{13}C$ NMR and HMBC spectra of 3 suggested that this peptaibol had 18 amino acids residue and its sequence was very similar to trichorzin HA II (16),[xii] except for the additional isovaline residue. The $^{13}C$ NMR spectra showed two signals for the characteristic γ-methyl group of isovaline at δc 7.44 and 7.40, and the locations of these two isovalines were determined by the HMBC and ROESY correlations as Iva$^7$ and Iva$^{16}$. In order to confirm the sequence of 3, the MS/MS fragment analysis was performed, and the absolute configurations of amino acids were determined by Marfey's method as Ac-Aib$^1$-Gly$^2$-$_L$-Ala$^3$-

Aib$^4$-Aib$^5$-$_L$-Gln$^6$-$_D$-Iva$^7$-$_L$-Val$^8$-Aib$^9$-Gly$^{10}$-$_L$-Leu$^{11}$-Aib$^{12}$-$_L$-Pro$^{13}$-$_L$-Leu$^{14}$-Aib$^{15}$-$_D$-Iva$^{16}$-$_L$-Gln$^{17}$-$_L$-Leuol$^{18}$, named trichorzin NP C (5).

Example 4

Compound 4 was isolated as a colorless solid and gave the molecular formula of $C_{82}H_{144}N_{20}O_{21}$ based on the HRES-IMS data (m/z 873.5493 [M+H]$^{2+}$; calcd 873.5480). The analysis of 1D and 2D NMR suggested that the amino acid sequence of 4 was almost identical to that of trichorzin HA V (17).$^{xii}$ The $^{13}$C NMR of 4 exhibited two characteristic signals for the methyl groups of isoleucine at $\delta_C$ 16.1 and 10.8 instead of those of valine (17: $\delta_C$ 19.4 and 19.2). With the help of the fragment studies by the MS/MS experiment, the planar structure of 4 was established as Ac-Aib$^1$-Gly$^2$-Ala$^3$-Aib$^4$-Iva$^5$-Gln$^6$-Aib$^7$-Ile$^8$-Aib$^9$-Gly$^{10}$-Leu$^{11}$-Aib$^{12}$-Pro$^{13}$-Leu$^{14}$-Aib$^{15}$-Iva$^{16}$-Gln$^{17}$-Leuol$^{18}$. In order to prove the absolute configuration of α-carbon of amino acid, Marfey's method was used. However, in the case of the isoleucine, there are two pairs of isomers, $_{DL}$-Ile and $_{DL}$-alto-Ile, because of their β-carbon. On top of that, $_L$-Ile and $_L$-allo-Ile came out at the same retention time in Marfey's method ($t_R$=21.6). So, in order to distinguish these two isomers of Ile, GITC method (2,3,4,6-tetra-O-acetyl-β-$_D$-glucopyranosyl isothiocyanate) was carried out.$^{xv}$ On the basis of this analysis, the isoleucine of 4 was determined as $_L$-Ile, not $_L$-allo-Ile. As a result, the sequence of 4 was assigned as Ac-Aib$^1$-Gly$^2$-$_L$-Ala$^3$-Aib$^4$-$_D$-Iva$^5$-$_L$-Gln$^6$-Aib$^7$-$_L$-Ile$^8$-Aib$^9$-Gly$^{10}$-$_L$-Leu$^{11}$-Aib$^{12}$-$_L$-Pro$^{13}$- $_L$-Leu$^{14}$-Aib$^{15}$-$_D$-Iva$^{16}$-$_L$-Gln$^{17}$-$_L$-Leuol$^{18}$, and given the trivial name trichorzin NP D (4).

Example 5

Compound 5 was isolated as a colorless solid, and its molecular formula of $C_{83}H_{146}N_{20}O_{21}$ was determined from the HRESIMS data (m/z 850.5585 [M+H]$^{2+}$; calcd 850.5588). The 1D and 2D NMR spectra of 5 indicated that the sequence of this peptaibol consisted of 18 amino acids and looked similar to that of trichorzin HA VI (18).$^{xii}$ The fragment ions analysis also supported that the only difference between peptaibol 5 and 18 was the presence of an isoleucine, instead of a valine. In order to confirm the absolute configuration of all amino acids in this peptaibol, Marfey's and GITC methods were performed, comparing the derivatized amino acids from peptaibol 5 with those of authentic amino acid standards. Collectively, the absolute structure of 5 was determined as Ac-Aib$^1$-Gly$^2$-$_L$-Ala$^3$-Aib$^4$-$_D$-Iva$^5$-$_L$-Gln$^6$-$_D$-Iva$^7$-$_L$-Ile$^8$-Aib$^9$-Gly$^{10}$-$_L$-Leu$^{11}$-Aib$^{12}$-$_L$-Pro$^{13}$-$_L$-Leu$^{14}$-Aib$^{15}$-$_D$-Iva$^{16}$-$_L$-Gln$^{17}$-$_L$-Leuol$^{18}$, and given the trivial name trichorzin NP E (5). In addition, the CD spectrum of 18-AA peptaibols (2-5) also showed negative Cotton effects at 208 and 225 nm, which indicated the right-handed helical conformation of 2-5.

Example 6

Compound 6 was obtained as a colorless solid, and gave a sodiated ion at m/z 1438.8705 ([M+Na]+; calcd 1438.8644) from the HRESIMS spectra, indicating the molecular formula of $C_{68}H_{117}N_{15}O_{17}$. The $^1$H and $^{13}$C NMR revealed the characteristic pattern of peptaibols and suggested that the length of amino acids residue of 6 was shorter than the above-mentioned group, trichorzin HA series (1-5), which had 18 amino acids residue. The $^{13}$C NMR of 6 showed 15 carbonyl resonances at $\delta_C$ 171-178 ppm, and HSQC, HMBC, and COSY spectra deduced that 6 was composed of 14 amino acid residues including asparagine (Asn), serine (Ser), Aib, Pro, Val, Iva, Leu and Leuol. The sequence of 6 was confirmed by the HMBC and ROESY correlations as Ac-Iva$^1$-Asn$^2$-Leu$^3$-Aib$^4$-Pro$^5$-Ser$^6$-Val$^7$-Aib$^8$-Pro$^9$-Aib$^{10}$-Leu$^{11}$-Aib$^{12}$-Pro$^{13}$-Leuol$^{14}$. Also, the MS/MS spectra of [M+H]$^{2+}$ ion displayed three pairs of intense fragment ions at m/z 454 (Ac-Aib$^4$) and 963 (Pro$^5$-Leuol$^{14}$), m/z 822 (Ac-Aib$^8$) and 595 (Pro$^9$-Leuol$^{14}$), and m/z 1117 (Ac-Aib$^{12}$) and 215 (Pro$^{13}$-Leuol$^{14}$) stemming from the cleavage of the labile bonds between Aib and Pro. These significant ions as well as minor fragment ions supported that this sequence was similar to that of harzianin HC I (20),$^{xvi}$ which was one of the harzianin HC series peptaibols (14 units) typically obtained from the *Trichoderma harzianum*, and the only difference between 6 and 20 was the presence of Iva$^2$ instead of Aib$^2$. In order to figure out the absolute configuration of every single amino acid residue, Marfey's method was performed, and the right-handed helical conformation of 6 was detected by a negative Cotton effect at 205 and 230 nm in its CD spectrum.$^{xiv}$ Thus, the absolute structure of 6 was established as Ac-D-Iva$^1$-$_L$-Asn$^2$-$_L$-Leu$^3$-Aib$^4$-$_L$-Pro$^5$-$_L$-Ser$^6$-$_L$-Val$^7$-Aib$^8$-$_L$-Pro$^9$-Aib$^{10}$-$_L$-Leu$^{11}$-Aib$^{12}$-$_L$-Pro$^{13}$-$_L$-Leuol$^{14}$, named harzianin NP A (6).

Example 7

Compound 7 was isolated as a colorless solid and its molecular formula was determined as $C_{69}H_{119}N_{15}O_{17}$ by the HRESIMS spectra (m/z 715.9541 [M+H]$^{2+}$; calcd 715.9527), indicating the presence of 18 degrees of unsaturation. On the basis of the analysis of the 1D and 2D NMR, the sequence of this peptaibol almost corresponded to that of harzianin HC XI (22).$^{xvi}$ The fragment ion at m/z 256 (Ac-Aib$^1$-Gln$^2$) and an additional carbon signal in the $^{13}$C NMR verified the difference between the sequence of 7 and 22 was the presence of glutamine instead of asparagine at the second amino acid site. Furthermore, the absolute structure of 7 was confirmed by Marfey's and GITC methods as Ac-Aib$^1$-$_L$-Gln$^2$-$_L$-Leu$^3$-Aib$^4$-$_L$-Pro$^5$-$_L$-Ser$^6$-$_L$-Ile$^7$-Aib$^8$-$_L$-Pro$^9$-Aib$^{10}$-$_L$-Leu$^{11}$-Aib$^{12}$-$_L$-Pro$^{13}$-$_L$-Leuol$^{14}$, and given the trivial name harzianin NP B (7).

Example 8

Compound 8 was obtained as a colorless solid and its molecular formula, $C_{69}H_{119}N_{15}O_{17}$, was determined from the HRESIMS spectrum (m/z 715.9541 [M+H]$^{2+}$; calcd 715.9527), corroborating the $^{13}$C NMR spectrum, which showed one more resonance than those of 6. The $^{13}$C NMR and HSQC of 8 displayed two characteristic signals for methyl groups of isoleucine at $\delta_C$ 15.8 and 11.5, instead of those of valine (6: $\delta_C$ 19.3 and 18.2), which verified that the sequence of 8 was Ac-Iva$^1$-Asn$^2$-Leu$^3$-Aib$^4$-Pro$^5$-Ser$^6$-Ile$^7$-Aib$^8$-Pro$^9$-Aib$^{10}$-Leu$^{11}$-Aib$^{12}$-Pro$^{13}$-Leuol$^{14}$. Also, the HMBC and ROESY correlations and MS/MS fragment ions studies supported this sequence. Furthermore, the absolute configurations of amino acid residues were elucidated by the above-mentioned way as Ac-$_D$-Iva$^1$-$_L$-Asn$^2$-$_L$-Leu$^3$-Aib$^4$-$_L$-Pro$^5$-$_L$-Ser$^6$-$_L$-Ile$^7$-Aib$^8$-$_L$-Pro$^9$-Aib$^{10}$-$_L$-Leu$^{11}$-Aib$^{12}$-$_L$-Pro$^{13}$-$_L$-Leuol$^{14}$, named harzianin NP C (8).

Example 9

Compound 9 was isolated as a colorless solid and the HRESIMS data of 9 were consistent with the molecular formula of $C_{70}H_{121}N_{15}O_{17}$ (m/z 722.9621 [M+H]$^{2+}$; calcd 722.9605), which deduced this peptaibol carried one more carbon unit than the sequences of peptaibol 8 and harzianin HC XII (23).[xvi] The $^1$H NMR spectrum of 9, with the help of the HMBC correlations between NH and α carbon, displayed three signals for the NH of Aib at $δ_H$ 8.44, 8.28 and 8.19, and two signals for the NH of Iva at $δ_H$ 9.80 and 7.89. On the other hand, 8 and 23 carried four Aibs and one Iva, which suggested that one of Aibs was replaced with an Iva in 9. The fragment ions at m/z 933 (Ac-Pro$^9$) and 1032 (Ac-Iva$^{10}$), and the HMBC and ROESY correlations indicated that the tenth amino acid residue site was substituted with an Iva, and Marfey's and GITC methods were used to elucidate the absolute configuration of all amino acid residues. As a result, the absolute structure of 9 was established as Ac-$_D$-Iva$^1$-$_L$-Asn$^2$-$_L$-Leu$^3$-Aib$^4$-$_L$-Pro$^5$-$_L$-Ser$^6$-$_L$-Ile$^7$-Aib$^8$-$_L$-Pro$^9$-$_D$-Iva$^{10}$-$_L$-Leu$^{11}$-Aib$^{12}$-$_L$-Pro$^{13}$-$_L$-Leuol$^{14}$, named harzianin NP D (9).

Example 10

Compound 10 was obtained as a colorless solid and the molecular formula was determined to be $C_{69}H_{119}N_{15}O_{16}$ based on the HRESIMS spectrum (m/z 707.9569 [M+H]$^{2+}$; calcd 707.9552). The molecular weight of 10 was 16 (amu) lower than that of 7, which was in accordance with the mass of oxygen. The $^{13}$C NMR and HSQC spectrum showed a doublet methyl group signal at $δ_C$ 16.8, instead of an oxygenated methylene moiety ($δ_C$ 62.1) of Ser in 7, which revealed that Ser was substituted with Ala in 10. The HMBC, ROESY and MS/MS experiment were performed to confirm the sequence, and Marfey's and GITC methods were used to establish the absolute structure of 10. Thus, peptaibol 10 was determined as Ac-Aib$^1$-$_L$-Gln$^2$-$_L$-Leu$^3$-Aib$^4$-$_L$-Pro$^5$-$_L$-Ala$^6$-$_L$-Ile$^7$-Aib$^8$-$_L$-Pro$^9$-Aib$^{10}$-$_L$-Leu$^{11}$-Aib$^{12}$-$_L$-Pro$^{13}$-$_L$-Leuol$^{14}$, and given the trivial name harzianin NP E (10).

Example 11

Compound 11 was isolated as a colorless solid and it was found to have a molecular formula of $C_{70}H_{121}N_{15}O_{16}$ from the HRESIMS analysis (m/z 714.9647 [M+H]$^{2+}$; calcd 714.9631). The $^1$H, $^{13}$C and HSQC NMR data of 11 were similar to those of 10, except for the presence of an Iva (11: $δ_C$ 59.6 and 7.7) instead of one of Aibs, which means another carbon unit was attached to a certain methyl group of Aib in 10 on the basis of the difference of molecular weight (14 amu). The HMBC correlation between NH at 5H 10.01 and carbons at $δ_C$ 177.8, 172.1 and 59.6) indicated that Iva was located at the first amino acid site of this sequence. The ROESY spectrum and MS/MS fragment ions experiment also proved the sequence, and the absolute structure of 11 was turned out to be Ac-$_D$-Iva$^1$-$_L$-Gln$^2$-$_L$-Leu$^3$-Aib$^4$-$_L$-Pro$^5$-$_L$-Ala$^6$-$_L$-Ile$^7$-Aib$^8$-$_L$-Pro$^9$-Aib$^{10}$-$_L$-Leu$^{11}$-Aib$^{12}$-$_L$-Pro$^{13}$-$_L$-Leuol$^{14}$, named harzianin NP F (11).

Example 12

Compound 12 was obtained as a colorless solid and gave a molecular ion peak at m/z 714.9644 [M+H]$^{2+}$ (calcd 714.9631) in the HRESIMS spectrum, which was consistent with the molecular formula of $C_{70}H_{121}N_{15}O_{16}$. Analysis of 1D and 2D NMR spectroscopic data revealed the sequence of 12 was almost identical to that of 9, except for the presence of Ala, instead of Ser at the sixth site where Ser was found in the peptaibols 6-9. So, the absolute structure of 12 was turned out to be Ac-$_D$-Iva$^1$-$_L$-Asn$^2$-$_L$-Leu$^3$-Aib$^4$-$_L$-Pro$^5$-$_L$-Ala$^6$-$_L$-Ile$^7$-Aib$^8$-$_L$-Pro$^9$-$_D$-Iva$^{10}$-$_L$-Leu$^{11}$-Aib$^{12}$-$_L$-Pro$^{13}$-$_L$-Leuol$^{14}$ by using the same way as previous ones, named harzianin NP G (12).

Example 13

Compound 13 was isolated as a colorless solid and the positive mode HRESIMS spectrum of 13 displayed a double-charged ion at m/z 721.9717 [M+H]$^{2+}$ (calcd 721.9709), which was assigned as the molecular formula of $C_{71}H_{123}N_{15}O_{16}$. Its NMR spectra revealed nearly identical sequence to that of 12, except for the presence of Gln (13: $δ_C$ 25.1 and 31.5), which was replaced with an Asn (12: $δ_C$ 35.1). The predicted sequence was confirmed by the fragment ions analysis and 2D spectra such as HMBC and ROESY experiment, and the absolute configurations of the whole amino acid residue of 13 were elucidated by Marfey's and GITC methods. Thus, the structure of 13 was determined as Ac-$_D$-Iva$^1$-$_L$-Gln$^2$-$_L$-Leu$^3$-Aib$^4$-$_L$-Pro$^5$-$_L$-Ala$^6$-$_L$-Ile$^7$-Aib$^8$-$_L$-Pro$^9$-$_D$-Iva$^{10}$-$_L$-Leu$^{11}$-Aib$^{12}$-$_L$-Pro$^{13}$-$_L$-Leuol$^{14}$, and given the trivial name harzianin NP H (13). Moreover, the right-handed helical conformation of 7-13 were detected by negative Cotton effects at 205 and 230 nm in its CD spectrum.

Example 14

Compound 14 was isolated as a colorless solid and exhibited the molecular formula of $C_{59}H_{104}N_{12}O_{13}$ as deduced from the sodiated ion at m/z 1211.7720 [M+Na]$^+$ (calcd 1211.7738) in the HRESIMS spectrum. The $^{13}$C NMR spectrum of 14 displayed 59 carbon signals including 11 amide carbonyl resonances at $δ_C$ 170.0-180.0, which indicated the length of this sequence looked shorter than the above-mentioned series of peptaibols (1-13). On the basis of the 2D NMR spectrum of 14, it was turned out to have one carbonyl group of an acetyl group at N-terminus, two amide carbons of a Gln, and a Leuol at C-terminus with no carbonyl, which suggested that the structure of 14 had 11 amino acid residues. The spectroscopic data of 14 was similar to those of harzianin HB I (27),[xvii] showing an exchange of Aib$^1$-Asn$^2$ in 27 by Iva$^1$-Gln$^2$ in 14. The 28 (amu) difference of molecular weight between 14 and 27, corresponding to two $CH_2$ units, supported that each carbon unit was attached to Aib and Asn in 27. By the aid of the HMBC and ROESY correlations, the planar structure of 14 was assigned as Ac-Iva$^1$-Gln$^2$-Leu$^3$-Ile$^4$-Aib$^5$-Pro$^6$-Iva$^7$-Leu$^8$-Aib$^9$-Pro$^{10}$-Leuol$^{11}$. Also, Marfey's and GITC analysis of 14 identified the absolute configuration of most amino acids in this sequence were L form, with the exception of $_D$-Iva. Furthermore, a negative Cotton effect at 207 and 230 nm indicated the right-handed helical conformation of 14.[xiv] Therefore, the structure of peptaibol 14 was established as Ac-$_D$-Iva$^1$-$_L$-Gln$^2$-$_L$-Leu$^3$-$_L$-Ile$^4$-Aib$^5$-$_L$-Pro$^6$-$_D$-Iva$^7$-$_L$-Leu$^8$-Aib$^9$-$_L$-Pro$^{10}$-$_L$-Leuol$^{11}$, named harzianin NP I (14).

Examples 15-27

The five known trichorzin HA series peptaibols isolated from this fungus were identified as trichorzin HA I (15),[xii] trichorzin HA II (16),[xii] trichorzin HA V (17),[xii] trichorzin HA VI (18),[xii] and trichorzin HA VII (19),[xii] and the seven known harzianin HC series peptaibols as well as one known harzianin HB type peptaibol were identified as harzianin HC I (20),[xvi] harzianin HC III (21),[xvi] harzianin HC XI (22),[xvi] harzianin HC XII (23),[xvi] harzianin HC XIV (24),[xvi] harzianin HC X (25),[xvi] harzianin HC XV (26),[xvi] and harzianin HB I (27),[xvii] by the comparison of their reported spectroscopic data in literature, respectively.

Examples 28-37

Examples 28-37 provide a structure Elucidation of Peptaibols Isolated from *H. pachybasioides*.

Example 28

Compound 28 was obtained as a colorless solid and its molecular formula was determined as $C_{37}H_{69}N_7O_8$ on the basis of the HRESIMS spectrum (m/z 740.5278 [M+H]$^+$; calcd 740.5280). The $^1$H NMR data of 28 displayed seven NH protons between $\delta_H$ 8.0 and 10.0 ppm, several α-protons between $\delta_H$ 3.7 and 5.0 ppm, and a few signals of $CH_2$ and $CH_3$, which indicated 28 carried seven amino acid residues. These amino acids in 28 were turned out to be two Aibs, two Glys, one Val, one Ile, and one Leuol by the analysis of the $^{13}$C, HMBC and COSY NMR spectrum. After assigning signals for these amino acid residues in the NMR spectrum, there were still eight unassigned peaks in the $^{13}$C NMR spectrum of 28. This eight carbons group was determined as n-octanoyl moiety attached to N-terminus by the COSY and HMBC correlations. The HMBC and ROESY correlations suggested that the amino acid sequence of 28 was n-Oct-Aib$^1$-Gly$^2$-Val$^3$-Aib$^4$-Gly$^5$-Ile$^6$-Leuol$^7$, which was supported by the MS/MS fragments ion analysis. While the 11-AA octanoyl lipopeptaibols are commonly obtained from the fungal extracts, the 7-AA octanoyl lipopeptaibols like 28 were very rarely isolated.[xviii] The absolute configurations of each amino acid residue were determined by Marfey's and GITC method the same way as abovementioned peptaibols (1-14). Thus, the absolute structure of 28 was established as n-Oct-Aib$^1$-Gly$^2$-$_L$-Val$^3$-Aib$^4$-Gly$^5$-$_L$-Ile$^6$-$_L$-Leuol$^7$, named hypocrin NP A (28).

Example 29

Compound 29 was isolated as a colorless solid, and the molecular formula was determined to be $C_{37}H_{69}N_7O_8$ by the HRESIMS spectrum (m/z 740.5292 [M+H]$^+$; calcd 740.5280), which was the same chemical formula as compound 28. Furthermore, the $^1$H and $^{13}$C NMR data were almost corresponded with those of 28 except for the presence of signals for a leucine instead of an isoleucine. By using Marfey's method, the absolute structure of 29 was confirmed as n-Oct-Aib$^1$-Gly$^2$-$_L$-Leu$^3$-Aib$^4$-Gly$^5$-$_L$-Val$^6$-$_L$-Leuol$^7$, given the trivial name hypocrin NP B (29).

Example 30

Compound 30 was obtained as a colorless solid, and its HRESIMS spectrum displayed a protonated ion peak at m/z 754.5453 [M+H]$^+$ (calcd 754.5437), indicating of the molecular formula of $C_{38}H_{71}N_7O_8$. Comparing the NMR data of 30 with those of 28 and 29, compound 30 had one more methylene group ($CH_2$) than 28 and 29, which was consistent with the difference of molecular weight (14 amu). The HMBC and ROESY spectrum suggested that the additional methylene group was added to third amino acid residue, which indicated that Val$^3$ in 28 was replaced with Leu$^3$ in 30. The absolute configurations of the amino acids of 30 were determined by Marfey's and GITC methods as n-Oct-Aib$^1$-Gly$^2$-$_L$-Leu$^3$-Aib$^4$-Gly$^5$-$_L$-Ile$^6$-$_L$-Leuol$^7$, named hypocrin NP C (30).

Example 31

Compound 31 was isolated as a colorless solid, and its HRESIMS spectrum showed a pseudomolecular ion peak at m/z 1024.6771 [M+H]$^+$ (calcd 1024.6765), corresponding to the molecular formula of $C_{49}H_{89}N_{11}O_{12}$. Analysis of 1D and 2D NMR indicated that 31 carried 11 amino acid residues including Aib, Gly, Val, and Leuol that compounds 28-30 also had, and 31 shared the same pattern with 28-30; first four residues: n-Oct-Aib-Gly-(Val or Leu)-, and last four residues: -Aib-Gly-(Val or Leu or Ile)-Leuol.[xviii] Both of variable residues in the repeated sequence of 31 were identified as Val, also, the sequence of the rest of the amino acid residues were turned out to be Aib-Gly-Gly-Val and be located between the repeated pattern by the HMBC and ROESY correlations. By using the Marfey's method to confirm the absolute configuration of amino acid, as a result, the structure of 31 was confirmed as n-Oct-Aib$^1$-Gly$^2$-$_L$-Val$^3$-Aib$^4$-Gly$^5$-Gly$^6$-$_L$-Val$^7$-Aib$^8$-Gly$^9$-$_L$-Val$^{10}$-$_L$-Leuol$^{11}$, and given trivial name, hypocrin ND A (31).

Example 32

Compound 32 was isolated as a colorless solid, and the molecular formula of $C_{50}H_{91}N_{11}O_{12}$ was established from the HRESIMS data (m/z 1038.6919 [M+H]$^+$, calcd 1038.6921). On the basis of the interpretation of 1D and 2D NMR spectrum, compound 32 shared the characteristic pattern like n-Oct-Aib$^1$-Gly$^2$-(Val or Leu)$^3$-Aib$^4$-Gly$^5$-Gly$^6$-(Val or Leu)$^7$-Aib$^8$-Gly$^9$-(Val or Leu or Ile)$^{10}$-Leuol$^{11}$ with 31, and the amino acids in the changeable regions were determined as Leu$^3$, Val$^7$, and Val$^{10}$, respectively. According to the results of Marfey's method, the absolute structure of 32 was turned out as n-Oct-Aib$^1$-Gly$^2$-$_L$-Leu$^3$-Aib$^4$-Gly$^5$-Gly$^6$-$_L$-Val$^7$-Aib$^8$-Gly$^9$-$_L$-Val$^{10}$-$_L$-Leuol$^{11}$, and given trivial name, hypocrin ND B (32).

Examples 33-35

Compounds 33, 34 and 35 were isolated as a colorless solid, and their molecular formula were turned out to be the same as $C_{51}H_{93}N_{11}O_{12}$ from their HRESIMS spectrum (33: m/z 1052.7061 [M+H]$^+$, 34: m/z 1052.7062 [M+H]$^+$, 35: m/z 1052.7076 [M+H]$^+$, calcd 1052.7078). The analysis of the 1D and 2D NMR spectrum indicated that compounds 33, 34 and 35 exhibited the certain pattern the same as 31 and 32, but each of them carried different amino acids at the variable site (33: Leu$^3$, Val$^7$, and Leu$^{10}$, 34: Leu$^3$, Val$^7$, and Ile$^{10}$, and 35: Val$^3$, Leu$^7$, and Ile$^{10}$). Marfey's and GITC method were performed so as to determine the absolute configurations of these aliphatic amino acids. Thus, the sequences of 33, 34 and 35 were identified as n-Oct-Aib$^1$-Gly$^2$-$_L$-Leu$^3$-Aib$^4$-Gly$^5$-Gly$^6$-$_L$-Val$^7$-Aib$^8$-Gly$^9$-$_L$-Leu$^{10}$-$_L$-Leuol$^{11}$ (33), n-Oct-Aib$^1$-Gly$^2$-$_L$-Leu$^3$-Aib$^4$-Gly$^5$-Gly$^6$-$_L$-Val$^7$-Aib$^8$-Gly$^9$-$_L$-Ile$^{10}$-$_L$-Leuol$^{11}$ (34), and n-Oct-Aib$^1$-Gly$^2$-$_L$-Val$^3$-Aib$^4$-Gly$^5$-Gly$^6$-$_L$-Leu$^7$-Aib$^8$-Gly$^9$-$_L$-Ile$^{10}$-$_L$-Leuol$^{11}$ (35), and named hypocrins ND C (33), D (34), and E (35), respectively.

Example 36

Compound 36 was obtained as a colorless solid, and the HRESIMS spectrum of 36 showed a protonated ion at m/z 1088.7073 [M+Na]$^+$ (calcd 1088.7054), corresponding to the molecular formula of $C_{52}H_{95}N_{11}O_{12}$. Its $^1$H and $^{13}$C NMR had no signal for valines and isoleucines, and they only showed resonances for leucines, which indicated that all the changeable regions in the sequence of 36 were substituted by Leu. The absolute structure of 36 was confirmed by Marfey's method as n-Oct-Aib$^1$-Gly$^2$-$_L$-Leu$^3$-Aib$^4$-Gly$^5$-Gly$^6$-$_L$-Leu$^7$-Aib$^8$-Gly$^9$-$_L$-Leu$^{10}$-$_L$-Leuol$^{11}$, which was named hypocrin ND F (36). In addition, the CD spectrum of 11-AA lipopeptaibols (31-36) showed negative Cotton effects at 206 and 223 nm, which demonstrated the right-handed helical conformation.

Example 37

Compound 37 was isolated as a colorless solid, and its molecular formula of $C_{63}H_{113}N_{15}O_{16}$ was determined from the HRESIMS data (m/z 1358.8427 [M+Na]$^+$; calcd 1358.8382). The $^{13}$C and HSQC NMR spectrum of 37 displayed the presence of 63 carbons signals including 15 amide carbonyls at 5c 170-180 ppm, and the HMBC and COSY correlations suggested that this peptaibol consisted of 15 amino acid residues with n-octanoyl moiety at the N-terminus. On the basis of the interpretations of NMR experiments, this peptaibol had four more amino acid residues (Aib-Gly-Gly-Val) than compounds 31-36, like 31-36 carried four more residues than compounds 28-30. By using Marfey's and GITC methods, the absolute structure of 37 was elucidated as n-Oct-Aib$^1$-Gly$^2$-$_L$-Val$^3$-Aib$^4$-Gly$^5$-Gly$^6$-$_L$-Val$^7$-Aib$^8$-Gly$^9$-Gly$^{10}$-$_L$-Val$^{11}$-Aib$^{12}$-Gly$^{13}$-$_L$-Ile$^{14}$-$_L$-Leuol$^{15}$, and named hypocrin NG A (37).

Examples 38-40

Compounds 38, 39 and 40 were isolated as a colorless solid, and had the same molecular formula of $C_{64}H_{115}N_{15}O_{16}$, as determined by the HRESIMS data (38: m/z 1372.8540 [M+Na]$^+$, 39: m/z 1350.8716 [M+H]$^+$, 40: m/z 1372.8555 [M+Na]$^+$ calcd 1350.8719 [M+H]$^+$ and 1372.8538 [M+Na]$^+$). The 1D and 2D NMR experiment suggested that compounds 38, 39 and 40 also shared the repeated pattern predicted by the spectroscopic data of the previous peptaibols, which is n-Oct-Aib$^1$-Gly$^2$-(Val or Leu)$^3$-Aib$^4$-Gly$^5$-Gly$^6$-(Val or Leu)$^7$-Aib$^8$-Gly$^9$-Gly$^{10}$-(Val or Leu)$^{11}$-Aib$^{12}$-Gly$^{13}$-Ile$^{14}$-$_L$-Leuol$^{15}$. The capricious parts (3$^{rd}$, 7$^{th}$, and 11$^{th}$) in their sequences were identified as Leu$^3$, Val$^7$, and Val$^{11}$ (38), Val$^3$, Leu$^7$, and Val$^{11}$ (39), and Val$^3$, Val$^7$, and Leu$^{11}$ (40), respectively. With the aid of Marfey's and GITC methods, the absolute sequences of 38, 39, and 40 were assigned as n-Oct-Aib$^1$-Gly$^2$-$_L$-Leu$^3$-Aib$^4$-Gly$^5$-Gly$^6$-$_L$-Val$^7$-Aib$^8$-Gly$^9$-Gly$^{10}$-$_L$-Val$^{11}$-Aib$^{12}$-Gly$^{13}$-$_L$-Ile$^{14}$-$_L$-Leuol$^{15}$ (38), n-Oct-Aib$^1$-Gly$^2$-$_L$-Val$^3$-Aib$^4$-Gly$^5$-Gly$^6$-$_L$-Leu$^7$-Aib$^8$-Gly$^9$-Gly$^{10}$-$_L$-Val$^{11}$-Aib$^{12}$-Gly$^{13}$-$_L$-Ile$^{14}$-$_L$-Leuol$^{15}$ (39), and n-Oct- Aib$^1$-Gly$^2$-$_L$-Val$^3$-Aib$^4$-Gly$^5$-Gly$^6$-$_L$-Val$^7$-Aib$^8$-Gly$^9$-Gly$^{10}$-$_L$-Leu$^{11}$-Aib$^{12}$-Gly$^{13}$-$_L$-Ile$^{14}$-$_L$-Leuol$^{15}$ (40), and given trivial names hypocrins NG B (38), C (39), and D (40).

Examples 41-43

Compounds 41, 42, and 43 were isolated as a colorless solid, and their HRESIMS data exhibited sodiated ion peaks at m/z 1386.8720 [M+Na]$^+$, 1386.8722 [M+Na]$^+$, 1386.8685 [M+Na]$^+$ (calcd 1386.8695), respectively, indicating a molecular formula of $C_{65}H_{117}N_{15}O_{16}$. Comparing the NMR data of 41-43 with those of 38-40, 41-43 carried one more Leu residue instead of Val in 38-40, which means there were two leucines and one valine at the variable sites. So, on the basis of the NMR and above-mentioned chemical reaction studies, the absolute structures were established as n-Oct-Aib$^1$-Gly$^2$-$_L$-Val$^3$-Aib$^4$-Gly$^5$-Gly$^6$-$_L$-Leu$^7$-Aib$^8$-Gly$^9$-Gly$^{10}$-$_L$-Leu$^{11}$-Aib$^{12}$-Gly$^{13}$-L-Ile$^{14}$-$_L$-Leuol$^{15}$ (41), n-Oct-Aib$^1$-Gly$^2$-$_L$-Leu$^3$-Aib$^4$-Gly$^5$-Gly$^6$-$_L$-Val$^7$-Aib$^8$-Gly$^9$-Gly$^{10}$-$_L$-Leu$^{11}$-Aib$^{12}$-Gly$^{13}$-$_L$-Ile$^{14}$-$_L$-Leuol$^{15}$ (42), and n-Oct-Aib$^1$-Gly$^2$-$_L$-Leu$^3$-Aib$^4$-Gly$^5$-Gly$^6$-$_L$-Leu$^7$-Aib$^8$-Gly$^9$-Gly$^{10}$-$_L$-Val$^{11}$-Aib$^{12}$-Gly$^{13}$-$_L$-Ile$^{14}$-$_L$-Leuol$^{15}$ (43), and given trivial names hypocrins NG E (41), F (42), and G (43). Furthermore, the CD spectrum of 15-AA lipopeptaibols (37-43) verified the right-handed helical conformation according to the negative Cotton effects at 206 and 222 nm.

Examples 44-52

The nine known peptaibols isolated from this fungus were identified as trikoningin KB I (44),$^{xix}$ trichogin A IV (45),$^{xx}$ trichogin GB IX (46),$^{xxi}$ trichosporin B IIId (47),$^{xxii}$ trichosporin B IIIa (48),$^{xxiii}$ trichosporin B IVc (49),$^{xxiii}$ trichosporin B VIb (50),$^{xxiv}$ trichosporin B VIa (51),$^{xxiv}$ and trichosporin B VIIa (52),$^{xxiv}$ by the comparison of their reported spectroscopic data in literature, respectively.

Example 53

A purpose of this example is to summarize results of structure-activity relationship studies.

FIGS. 1-3 and 7 are examples according to various embodiments illustrating peptaibol structures and a table indicating inhibitory effects for variations on the respective structure. FIG. 4-6 are examples according to various embodiments illustrating lipopeptaibol structures and a table indicating inhibitory effects for variations on the respective structure. First of all, all isolated peptaibols (1-52) could be generally divided into two groups, acetyl-peptaibols (1-27 and 47-52) with the acetyl group at the N-terminal and lipopeptaibols (28-46) with the n-octanoyl moiety at the N-terminus. Acetyl-peptaibols were further divided into four small groups depending on the length of sequence, 18-AA peptaibols (1-5 and 15-19, Table 1 in FIG. 1), 14-AA peptaibols (6-13 and 20-26, Table 2 in FIG. 2), 11-AA peptaibols (14 and 27, Table 3 in FIG. 3), and 20-AA peptaibols (47-52, Table 7 in FIG. 7). Lipopeptaibols were also divided into three small groups depending on the number of amino acid residues, 7-AA lipopeptaibols (28-30, Table 4 in FIG. 4), 11-AA lipopeptaibols (31-36 and 44-45, Table 5 in FIG. 5), and 15-AA lipopeptaibols (37-43 and 46, Table 6 in FIG. 6).

On the based on the bioactivity data, overall, acetyl-peptaibols 1-27 and 47-52 (EC$_{50}$ value: 0.29-1.77 μM) showed slightly more potent than lipopeptaibols 28-46 (EC$_{50}$ value: 0.44-3.66 μM). 20-AA peptaibols (47-52), which are the longest peptaibols we had isolated, displayed more cytotoxicity in HepG2 cell line than other acetyl-peptaibols. So, these peptaibols generated a low selectivity index (Hep G2 cell EC$_{50}$: P. falciparum EC$_{50}$) in the range of 3-18. Furthermore, 14-AA and 11-AA peptaibols showed a generally greater selectivity than that of 18-AA peptaibols. Among them, peptaibols 10, 11, 13, 14, and 24 showed a remarkable selectivity, with the SI value being more than 60. Even though there are only two cases of 11-AA peptaibols, 14-AA and 11-AA peptaibols might be suitable for antimalarial agents according to their SI value in the bioassay data. For lipopeptaibols, on the whole, 15-AA lipopeptaibols revealed more potent inhibitory effect against P. falciparum in comparison to 7-AA and 11-AA peptaibols. Also, peptaibol 37 displayed the highest SI value among these 15-AA lipopeptaibols, with a SI value of 59.

Example 54

Figure 12:
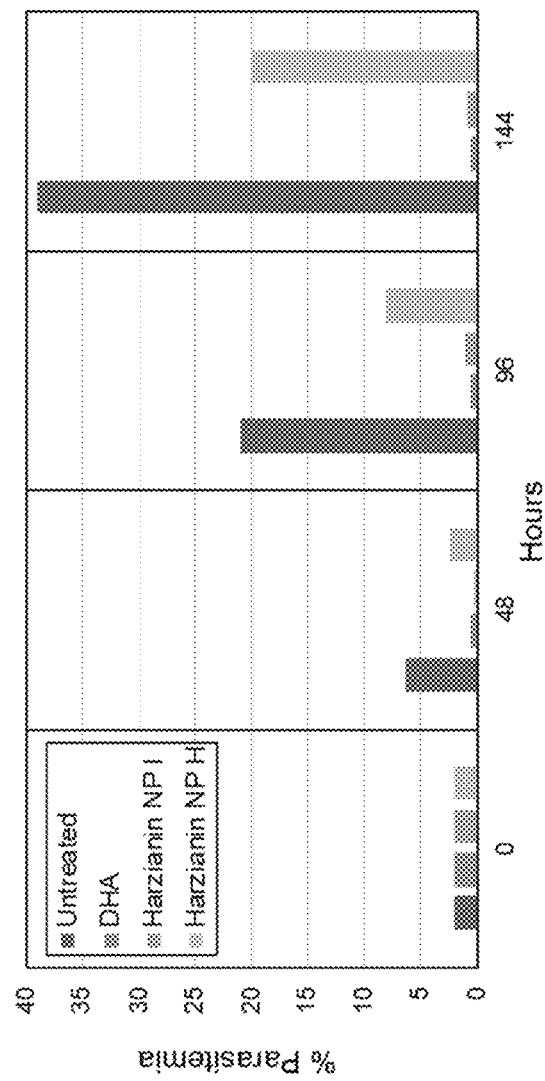
FIG. 12: is graph showing rate of killing by lead compounds being added to asynchronous culture at 5×EC$_{50}$ and incubated for 12 h prior to washing. Culture parasitemia was then monitored for 144 h.
Figure 13:
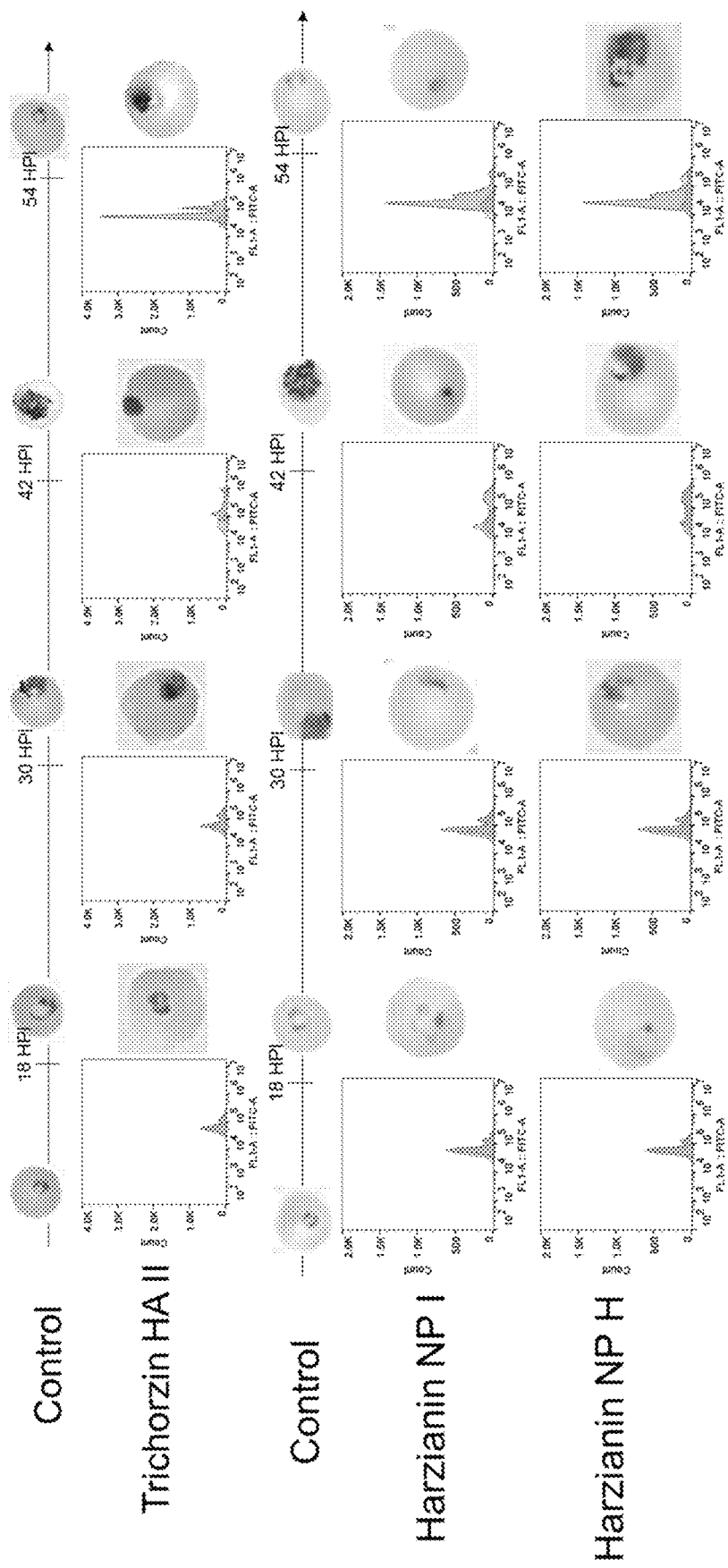
FIG. 13: is diagram showing differing phenotypes following 6HPI addition. Compounds were added to synchronous culture and incubated for 54 HPI following addition at specified timepoints. 6 HPI showed the greatest inhibition for all 3 compounds. 5×EC$_{50}$ was used for Harzianin compounds and 3×EC$_{50}$ was used for Trichorzin HA II. Samples were collected every 12 h for Geimsa staining and cytometric analysis with YOYO-1.
Figure 14:
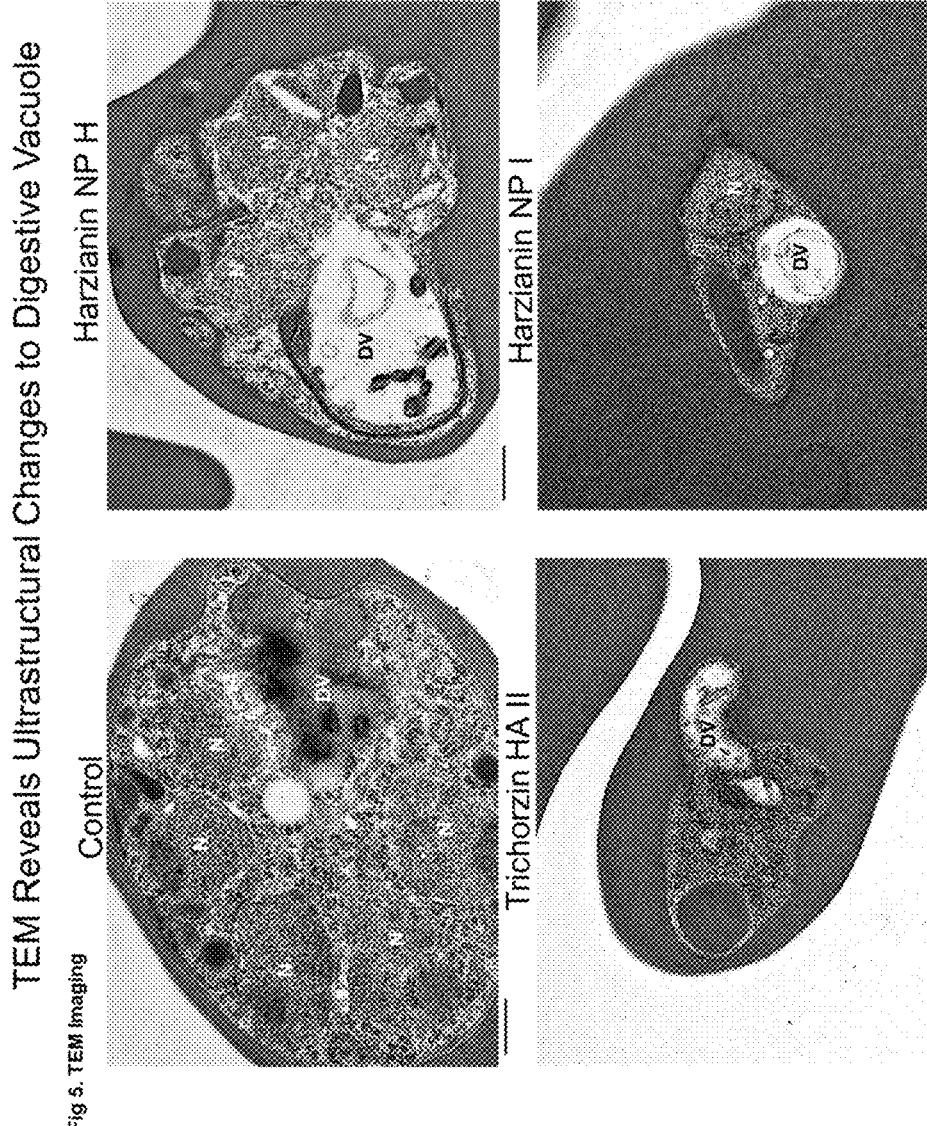
FIG. 14: shows TEM images revealing ultrastructural changes to digestive vacuoles. Scale bars represent 500 nm and images taken at 15,000×. N=nucleus, DV=digestive vacuole. Compound was added at 6 HPI and incubated until 42 HPI for fixation and sample collection.
Figure 15:
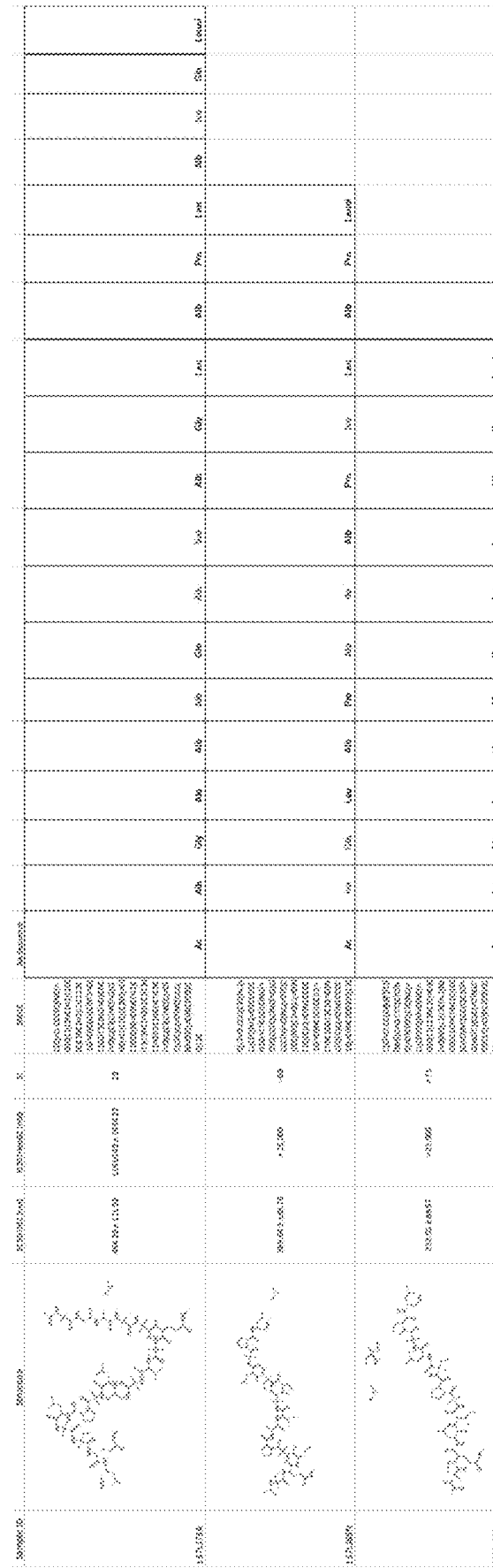
FIG. 15: is a table representing specific peptaibol agents having high activity according to EC50 assays and also provides an indication of the amino acid constituents.

Lead compounds Harzianin NP I and Harzianin NP H were added to asynchronous culture at 5×EC$_{50}$ and incubated for 12 h prior to washing. Culture parasitemia was then monitored for 144 h. FIG. 12 is graph showing rate of killing by Harzianin NP I and Harzianin NP H. The compounds were added to synchronous culture and incubated for 54 HPI following addition at specified timepoints (see FIG. 13). 6 HPI showed the greatest inhibition for all 3 compounds. $5 \times EC_{50}$ was used for Harzianin compounds and $3 \times EC_{50}$ was used for Trichorzin HA II. Samples were collected every 12 h for Geimsa staining and cytometric analysis with YOYO-1. Digestive vacuoles were observed by TEM imaging (see FIG. 14).

CONCLUSIONS

Even though many peptides obtained from natural products have been reported in regard to the antimalarial activities, there are few literatures reporting those of peptaibols. Since the peptaibols (1-52) in this paper, which were isolated from the *T. harzianum* and *H. pachybasioides*, were turned to have good selectivity, peptaibols, as well as the other type of peptides, may be the key to develop a new potent class of antimalarial drugs. So, it is necessary to do further investigation about a structure-activity relationship study, synthesis, and semi-synthesis to make more additional potent peptaibols.

EXPERIMENTAL SECTION

General Experimental Procedures.

Optical rotations were measured on a Rudolph Research Autopol III automatic polarimether. NMR spectra were obtained on Varian NMR spectrometers (400 and 500 MHz for $^1$H and 100 and 125 MHz for $^{13}$C). HRESIMS data were measured an Agilent 6538 high-mass-resolution QTOF mass spectrometer. ECD spectra were obtained on a JASCO J-715 circular dichroism spectrometer. Column chromatography was performed on silica gel (VWR, 40-60 μm, 6 Å) and HP20ss gel (Sorbtech). The preparative HPLC system was equipped with SCL-10A VP pumps and system controller and a Gemini 5 μm C18 column (210 Å, 250×21.2 mm) with flow rate of 10 mL/min. The semi-preparative HPLC were conducted on Waters system (1525 binary pumps and Waters 2998 photodiode array detectors) using Gemini 5 μm C18 column (110 Å, 250×10 mm), F5 column (110 Å, 250×10 mm), and biphenyl column (110 Å, 250×10 mm) with flow rate of 4 mL/min. All solvents were of ACS grade or better.

Fungal Material and Fermentation.

The *Trichoderma* sp. was isolated from a bike rack in Galveston, Texas, USA, and the *Hypocrea* sp. was obtained from back yard in Gilbertsville, Pennsylvania, USA. For the identification of these fungal species, mycelium was collected and subjected to homogenization in TE buffer (10 mM EDTA HCl, 0.1 mM EDTA, pH 8.0) with zirconium oxide beads in a Bullet Blender Storm (MidSci #BBY24M). These isolates were identified as *T. harzianum* and *H. pachybasioides* based on analysis of gene sequence data for its ribosomal internal transcribed spacer region and the 5.8S rRNA genes, respectively. (*T. harzianum*: GenBank accession no. MK558706, and *H. pachybasioides*: GenBank accession no. MK883713).

Each fungus was grown on Cheerios breakfast cereal supplemented with a 0.3% sucrose solution and 0.005% chloramphenicol in three large mycobags (Unicorn Bags, Plano, TX, USA) for 4 weeks.

Extraction and Isolation of *T. harzianum*.

The fungal cultures were extracted with EtOAc (2 L×3) at room temperature, and then the solution was evaporated under vacuo to obtain the EtOAc extract of 34 g (Fraction A).

Fraction A was subjected to silica gel vacuum column chromatography eluting with dichloromethane (fraction B), dichloromethane/MeOH (10/1, fraction C) and MeOH (fraction D) to give three fractions. Fraction D (10 g) was also fractionated into five fractions, fractions E (30% MeOH), F (50% MeOH), G (70% MeOH), H (90% MeOH) and I (100% MeOH), by HP20ss gel vacuum column chromatography. Fraction H (5 g) was further subjected to preparative HPLC (C18, 85 to 100% MeOH/H$_2$O in 15 min, flow rate: 10 mL/min) affording seven subfractions (H1~7). Subfraction H$_1$ (300 mg) was further separated by preparative HPLC (C18, 85 to 100% MeCN/H$_2$O in 15 min, flow rate: 10 mL/min) to give twelve subfractions (H1-1~H1-12). Compound 20 (2 mg, $t_R$=10 min) was isolated from subfraction H1-2 (10 mg) by semi-preparative HPLC (F5, MeCN:H$_2$O=42.5:57.5, flow rate: 4 mL/min). Subfraction H1-3 (20 mg) was purified by semi-preparative HPLC (F5, MeCN:H$_2$O=42.5:57.5, flow rate: 4 mL/min) to give compounds 21 (2.5 mg, $t_R$=11 min) and 6 (2.3 mg, $t_R$=12 min). Compound 22 (5 mg, $t_R$=12 min) was purified from subfraction H1-3 (20 mg) by semi-preparative HPLC (F5, MeCN:H$_2$O=42.5:57.5, flow rate: 4 mL/min). Subfraction H1-5 (35 mg) was purified by semi-preparative HPLC (F5, MeCN:H$_2$O=42.5:57.5, flow rate: 4 mL/min) to obtain compounds 7 (3 mg, $t_R$=14 min), 23 (6 mg, $t_R$=15 min) and 8 (6 mg, $t_R$=16 min). Compound 9 (10 mg, $t_R$=7 min) was isolated from subfraction H1-6 (35 mg) by semi-preparative HPLC (C18, MeCN:H$_2$O=47.5:52.5, flow rate: 4 mL/min). Subfraction H1-8 (30 mg) was further subjected to semi-preparative HPLC (F5, MeCN:H$_2$O=45:55, flow rate: 4 mL/min) to yield compounds 24 (2 mg, $t_R$=8 min), 25 (2 mg, $t_R$=10 min), and 27 (3 mg, $t_R$=12 min). Subfraction H1-9 (30 mg) was further purified by semi-preparative HPLC (F5, MeCN:H$_2$O=47.5:52.5, flow rate: 4 mL/min) to give compounds 10 (2 mg, $t_R$=8 min) and 11 (2 mg, $t_R$=11 min). Subfraction H$_1$-10 (20 mg) was further purified by semi-preparative HPLC (F5, MeCN:H$_2$O=47.5:52.5, flow rate: 4 mL/min) to yield compounds 26 (5 mg, $t_R$=10 min), 12 (5 mg, $t_R$=11 min) and 14 (1.5 mg, $t_R$=13 min). Compound 13 (3 mg, $t_R$=12 min) was isolated from subfraction H2 (25 mg) by semi-preparative HPLC (F5, MeCN:H$_2$O=47.5:52.5, flow rate: 4 mL/min). Subfraction H2 (100 mg) was further subjected to semi-preparative HPLC (F5, MeCN:H$_2$O=45:55, flow rate: 4 mL/min) to yield compounds 1 (2 mg, $t_R$=8 min), 15 (25 mg, $t_R$=9 min) and 2 (5 mg, $t_R$=10 min), and subfraction H$_3$ (450 mg) was further subjected to semi-preparative HPLC (F5, MeCN:H$_2$O=45:55, flow rate: 4 mL/min) to give compounds 16 (25 mg, $t_R$=11 min) and 3 (5 mg, $t_R$=12 min). Subfraction H5 (170 mg) was further purified by semi-preparative HPLC (F5, MeCN:H$_2$O=47.5:52.5, flow rate: 4 mL/min) to give compounds 17 (2 mg, $t_R$=9 min), 19 (3 mg, $t_R$=10 min), 18 (8 mg, $t_R$=11 min), and 4 (3 mg, $t_R$=12 min). Compound 5 (5 mg, $t_R$=11 min) was obtained from subfraction H$_6$, by semi-preparative HPLC (F5, MeCN:H$_2$O=50:50, flow rate: 4 mL/min).

Trichorzin NP A (1): colorless solid; $[\alpha]_D^{25}$+14 (c 0.1, MeOH); CD (MeOH) λmax (Δε) 208 (−30.5), 225 (−18.2); $^1$H NMR (500 MHz, Pyridine-d$_5$) and $^{13}$C NMR (100 MHz, Pyridine-d$_5$); HRESIMS m/z 852.5261 [M+H]$^{2+}$ (calcd for C$_{79}$H$_{139}$N$_{20}$O$_{21}$, 852.5245).

Trichorzin NP B (2): colorless solid; $[\alpha]_D^{25}$−6 (c 0.1, MeOH); CD (MeOH) λmax (Δε) 208 (−58.2), 225 (−33.8);

¹H NMR (500 MHz, Pyridine-$d_5$) and ¹³C NMR (100 MHz, Pyridine-$d_5$); HRESIMS m/z 853.0184 [M+H]$^{2+}$ (calcd for $C_{79}H_{138}N_{19}O_{22}$, 853.0166).

Trichorzin NP C (3): colorless solid; $[\alpha]_D^{25}$ +10 (c 0.1, MeOH); CD (MeOH) λmax (Δε) 208 (−62.1), 225 (−38.4); ¹H NMR (500 MHz, Pyridine-$d_5$) and ¹³C NMR (100 MHz, Pyridine-$d_5$); HRESIMS m/z 866.5419 [M+H]$^{2+}$ (calcd for $C_{81}H_{143}N_{20}O_{21}$, 866.5402).

Trichorzin NP D (4): colorless solid; $[\alpha]_D^{25}$ +12 (c 0.1, MeOH); CD (MeOH) λmax (Δε) 208 (−62.7), 225 (−37.8); ¹H NMR (500 MHz, Pyridine-$d_5$) and ¹³C NMR (100 MHz, Pyridine-$d_5$); HRESIMS m/z 873.5493 [M+H]$^{2+}$ (calcd for $C_{82}H_{145}N_{20}O_{21}$, 873.5480).

Trichorzin NP E (5): colorless solid; $[\alpha]_D^{25}$ +4 (c 0.1, MeOH); CD (MeOH) λmax (Δε) 208 (−46.6), 225 (−27.5); ¹H NMR (500 MHz, Pyridine-$d_5$) and ¹³C NMR (100 MHz, Pyridine-$d_5$); HRESIMS m/z 880.5585 [M+H]$^{2+}$ (calcd for $C_{83}H_{147}N_{20}O_{21}$, 880.5588).

Harzianin NP A (6): colorless solid; $[\alpha]_D^{25}$ +12 (c 0.1, MeOH); CD (MeOH) λmax (Δε) 205 (−38.0), 230 (−4.0); ¹H NMR (500 MHz, Pyridine-$d_5$) and ¹³C NMR (100 MHz, Pyridine-$d_5$); HRESIMS m/z 1438.8705 [M+Na]$^+$ (calcd for $C_{68}H_{117}N_{15}NaO_{17}$, 1438.8644).

Harzianin NP B (7): colorless solid; $[\alpha]_D^{25}$ −4 (c 0.1, MeOH); CD (MeOH) λmax (Δε) 205 (−48.6), 230 (−4.9); ¹H NMR (500 MHz, Pyridine-$d_5$) and ¹³C NMR (100 MHz, Pyridine-$d_5$); HRESIMS m/z 715.9541 [M+H]$^{2+}$ (calcd for $C_{69}H_{120}N_{15}O_{17}$, 715.9527).

Harzianin NP C (8): colorless solid; $[\alpha]_D^{25}$ +30 (c 0.1, MeOH); CD (MeOH) λmax (Δε) 205 (−42.4), 230 (−4.8); ¹H NMR (500 MHz, Pyridine-$d_5$) and ¹³C NMR (100 MHz, Pyridine-$d_5$); HRESIMS m/z 715.9541 [M+H]$^{2+}$ (calcd for $C_{69}H_{120}N_{15}O_{17}$, 715.9527).

Harzianin NP D (9): colorless solid; $[\alpha]_D^{25}$ +36 (c 0.1, MeOH); CD (MeOH) λmax (Δε) 205 (−39.9), 230 (−4.4); ¹H NMR (500 MHz, Pyridine-$d_5$) and ¹³C NMR (100 MHz, Pyridine-$d_5$); HRESIMS m/z 722.9621 [M+H]$^{2+}$ (calcd for $C_{70}H_{122}N_{15}O_{17}$, 722.9605).

Harzianin NP E (10): colorless solid; $[\alpha]_D^{25}$ −6 (c 0.1, MeOH); CD (MeOH) λmax (Δε) 205 (−45.8), 230 (−3.1); ¹H NMR (500 MHz, Pyridine-$d_5$) and ¹³C NMR (100 MHz, Pyridine-$d_5$); HRESIMS m/z 707.9569 [M+H]$^{2+}$ (calcd for $C_{69}H_{120}N_{15}O_{16}$, 707.9552).

Harzianin NP F (11): colorless solid; $[\alpha]_D^{25}$ +40 (c 0.1, MeOH); CD (MeOH) λmax (Δε) 205 (−27.5), 230 (−1.9); ¹H NMR (500 MHz, Pyridine-$d_5$) and ¹³C NMR (100 MHz, Pyridine-$d_5$); HRESIMS m/z 714.9647 [M+H]$^{2+}$ (calcd for $C_{70}H_{122}N_{15}O_{16}$, 714.9631).

Harzianin NP G (12): colorless solid; $[\alpha]_D^{25}$ +38 (c 0.1, MeOH); CD (MeOH) λmax (Δε) 205 (−27.5), 230 (−1.9); ¹H NMR (500 MHz, Pyridine-$d_5$) and ¹³C NMR (100 MHz, Pyridine-$d_5$); HRESIMS m/z 714.9644 [M+H]$^{2+}$ (calcd for $C_{70}H_{122}N_{15}O_{16}$, 714.9631).

Harzianin NP H (13): colorless solid; $[\alpha]_D^{25}$ +6 (c 0.1, MeOH); CD (MeOH) λmax (Δε) 205 (−33.6), 225 (−2.1); ¹H NMR (500 MHz, Pyridine-$d_5$) and ¹³C NMR (100 MHz, Pyridine-$d_5$); HRESIMS m/z 721.9717 [M+H]$^{2+}$ (calcd for $C_{71}F1124N_{15}O_{16}$, 721.9709).

Harzianin NP I (14): colorless solid; $[\alpha]_D^{25}$ +12 (c 0.1, MeOH); CD (MeOH) λmax (Δε) 207 (−10.2), 230 (−1.2); ¹H NMR (500 MHz, Pyridine-$d_5$) and ¹³C NMR (100 MHz, Pyridine-$d_5$); HRESIMS m/z 1211.7720 [M+Na]$^+$ (calcd for $C_{59}H_{104}N_{12}NaO_{13}$, 1211.7738).

Extraction and Isolation of H. pachybasioides.

The fungal cultures were extracted with EtOAc (2 L) three times at room temperature, and then the solution was evaporated under vacuo to obtain the EtOAc extract. Fraction A (21 g, crude extract) was subjected to silica gel vacuum column chromatography eluting with dichloromethane (fraction B), dichloromethane/MeOH (10/1, fraction C) and MeOH (fraction D) to afford three fractions. Fraction D (5 g) was further subjected to preparative HPLC (C18, 85% MeOH/H$_2$O, flow rate: 10 mL/min) affording nine fractions (E~M). Fraction E (25 mg) was further separated by semi-preparative HPLC (biphenyl, MeCN:H$_2$O=50:50, flow rate: 4 mL/min) to give compounds 29 (2 mg, $t_R$=9 min) and 28 (6 mg, $t_R$=10 min). Fraction F (20 mg) was further subjected to semi-preparative HPLC (biphenyl, MeCN:H$_2$O=50:50, flow rate: 4 mL/min) to yield compounds 31 (2 mg, $t_R$=8 min), 32 (5 mg, $t_R$=9 min), and 30 (25 mg, $t_R$=11 min). Fraction H (300 mg) was separated into four subfractions (H$_1$-4) by preparative HPLC (C18, 80-100% MeOH/H$_2$O in 20 min, flow rate: 10 mL/min), and fraction I was also fractionated into four subfractions (I1~4) by preparative HPLC (C18, 70-100% MeOH/H$_2$O in 15 min, flow rate: 10 mL/min). Subfraction H1 (130 mg) was purified by semi-preparative HPLC (biphenyl, MeCN:H$_2$O=50:50, flow rate: 4 mL/min) to give compounds 44 (15 mg, $t_R$=9 min) and 34 (37 mg, $t_R$=10 min). Subfraction H2 (50 mg) was purified by semi-preparative HPLC (biphenyl, MeCN:H$_2$O=47.5:52.5, flow rate: 4 mL/min) to obtain compounds 48 (6 mg, $t_R$=10 min), 47 (6 mg, $t_R$=11 min) and 33 (3 mg, $t_R$=16 min). Compound 49 (4 mg, $t_R$=11 min) was isolated from subfraction I1 (15 mg) by semi-preparative HPLC (F5, MeCN:H$_2$O=45:55, flow rate: 4 mL/min). Subfraction I3 (65 mg) was further subjected to semi-preparative HPLC (biphenyl, MeCN:H$_2$O=50:50, flow rate: 4 mL/min) to yield compounds 35 (2 mg, $t_R$=11 min), 45 (2 mg, $t_R$=12 min), and 36 (3 mg, $t_R$=13 min). Fraction J (90 mg) was further purified by semi-preparative HPLC (biphenyl, MeCN:H$_2$O=45:55, flow rate: 4 mL/min) to give compounds 50 (25 mg, $t_R$=9 min) and 51 (2 mg, $t_R$=10 min). Compound 52 (35 mg, $t_R$=10 min) was isolated from fraction L (60 mg) by semi-preparative HPLC (F5, MeCN:H$_2$O=47.5:52.5, flow rate: 4 mL/min). Fraction M (500 mg) was fractionated into five subfractions, subfractions M1 (30% MeOH), M2 (50% MeOH), M3 (70% MeOH), M4 (90% MeOH) and M5 (100% MeOH), by HP20ss gel vacuum column chromatography. Fraction M4 (180 mg) was separated into five subfractions (M4-1-5) by preparative HPLC (C18, 85-100% MeOH/H$_2$O in 15 min, flow rate: 10 mL/min). Subfraction M4-3 (20 mg) was further subjected to semi-preparative HPLC (F5, MeCN:H$_2$O=50:50, flow rate: 4 mL/min) to yield compounds 38 (1.5 mg, $t_R$=11 min), 39 (3 mg, $t_R$=12 min) and 43 (2 mg, $t_R$=13 min), and subfraction M4-4 (30 mg) was further subjected to semi-preparative HPLC (F5, MeCN:H$_2$O=52.5:47.5, flow rate: 4 mL/min) to give compounds 37 (3 mg, $t_R$=7 min), 42 (4 mg, $t_R$=9 min) and 46 (6 mg, $t_R$=11 min). Compounds 40 (6 mg, $t_R$=8 min) and 41 (7 mg, $t_R$=9 min) were obtained from subfraction M4-5 by semi-preparative HPLC (biphenyl, MeCN:H$_2$O=50:50, flow rate: 4 mL/min).

hypocrin NP A (28): colorless solid; $[\alpha]_D^{25}$ 14 (c 0.1, MeOH); CD (MeOH) λmax (Δε) 215 (9.6); ¹H NMR (500 MHz, Pyridine-$d_5$) and ¹³C NMR (100 MHz, Pyridine-$d_5$); HRESIMS m/z 740.5278 [M+H]$^+$ (calcd for $C_{37}H_{70}N_7O_8$, 740.5280).

hypocrin NP B (29): colorless solid; $[\alpha]_D^{25}$ +6 (c 0.1, MeOH); CD (MeOH) λmax (Δε) 215 (+2.54); ¹H NMR (500 MHz, Pyridine-$d_5$) and ¹³C NMR (100 MHz, Pyridine-$d_5$); HRESIMS m/z 740.5292 [M+H]$^+$ (calcd for $C_{37}H_{70}N_7O_8$, 740.5280).

hypocrin NP C (30): colorless solid; $[\alpha]_D^{25}$ −4 (c 0.1, MeOH); CD (MeOH) λmax (Δε) 215 (+3.5); ¹H NMR (500

MHz, Pyridine-$d_5$) and $^{13}$C NMR (100 MHz, Pyridine-$d_5$); HRESIMS m/z 754.5453 [M+H]$^+$ (calcd for $C_{38}H_{72}N_7O_8$, 754.5437).

hypocrin ND A (31): colorless solid; $[\alpha]_D^{25}$ −8 (c 0.1, MeOH); CD (MeOH) λmax (Δε) 206 (−14.4), 223 (−8.0); $^1$H NMR (500 MHz, Pyridine-$d_5$) and $^{13}$C NMR (100 MHz, Pyridine-$d_5$); HRESIMS m/z 1024.6771 [M+H]$^+$ (calcd for $C_{49}H_{90}N_{11}O_{12}$, 1024.6765).

hypocrin ND B (32): colorless solid; $[\alpha]_D^{25}$ −8 (c 0.1, MeOH); CD (MeOH) λmax (Δε) 205 (−20.2), 222 (−8.4); $^1$H NMR (500 MHz, Pyridine-$d_5$) and $^{13}$C NMR (100 MHz, Pyridine-$d_5$); HRESIMS m/z 1038.6919 [M+H]$^+$ (calcd for $C_{50}H_{92}N_{11}O_{12}$, 1038.6921).

hypocrin ND C (33): colorless solid; $[\alpha]_D^{25}$ −22 (c 0.1, MeOH); CD (MeOH) λmax (Δε) 205 (−25.2), 223 (−9.1); $^1$H NMR (500 MHz, Pyridine-$d_5$) and $^{13}$C NMR (100 MHz, Pyridine-$d_5$); HRESIMS m/z 1052.7061 [M+H]$^+$ (calcd for $C_{51}H_{94}N_{11}O_{12}$, 1052.7078).

hypocrin ND D (34): colorless solid; $[\alpha]_D^{25}$ −24 (c 0.1, MeOH); CD (MeOH) λmax (Δε) 205 (−295), 222 (−11.3); $^1$H NMR (500 MHz, Pyridine-$d_5$) and $^{13}$C NMR (100 MHz, Pyridine-$d_5$); HRESIMS m/z 1052.7062 [M+H]$^+$ (calcd for $C_{51}H_{94}N_{11}O_{12}$, 1052.7078).

hypocrin ND E (35): colorless solid; $[\alpha]_D^{25}$ −10 (c 0.1, MeOH); CD (MeOH) λmax (Δε) 206 (−32.4), 223 (−15.4); $^1$H NMR (500 MHz, Pyridine-$d_5$) and $^{13}$C NMR (100 MHz, Pyridine-$d_5$); HRESIMS m/z 1052.7076 [M+H]$^+$ (calcd for $C_{51}H_{94}N_{11}O_{12}$, 1052.7078).

hypocrin ND F (36): colorless solid; $[\alpha]_D^{25}$ +8 (c 0.1, MeOH); CD (MeOH) λmax (Δε) 204 (−14.4), 221 (−4.0); $^1$H NMR (500 MHz, Pyridine-$d_5$) and $^{13}$C NMR (100 MHz, Pyridine-$d_5$); HRESIMS m/z 1088.7073 [M+Na]$^+$ (calcd for $C_{52}H_{95}N_{11}NaO_{12}$, 1088.7054).

hypocrin NG A (37): colorless solid; $[\alpha]_D^{25}$ +6 (c 0.1, MeOH); CD (MeOH) λmax (Δε) 207 (−23.3), 221 (−16.1); $^1$H NMR (500 MHz, Pyridine-$d_5$) and $^{13}$C NMR (100 MHz, Pyridine-$d_5$); HRESIMS m/z 1358.8427 [M+Na]$^+$ (calcd for $C_{63}H_{113}N_{15}NaO_{16}$, 1358.8382).

hypocrin NG B (38): colorless solid; $[\alpha]_D^{25}$ +2 (c 0.1, MeOH); CD (MeOH) λmax (Δε) 207 (−17.5), 221 (−12.1); $^1$H NMR (500 MHz, Pyridine-$d_5$) and $^{13}$C NMR (100 MHz, Pyridine-$d_5$); HRESIMS m/z 1372.8540 [M+Na]$^+$ (calcd for $C_{64}H_{115}N_{15}NaO_{16}$, 1372.8538).

hypocrin NG C (39): colorless solid; $[\alpha]_D^{25}$ −12 (c 0.1, MeOH); CD (MeOH) λmax (Δε) 206 (−25.0), 222 (−15.8); $^1$H NMR (500 MHz, Pyridine-$d_5$) and $^{13}$C NMR (100 MHz, Pyridine-$d_5$); HRESIMS m/z 1350.8716 [M+H]$^+$ (calcd for $C_{64}H_{116}N_{15}O_{16}$, 1350.8719).

hypocrin NG D (40): colorless solid; $[\alpha]_D^{25}$ +6 (c 0.1, MeOH); CD (MeOH) λmax (Δε) 206 (−45.9), 219 (−28.8); $^1$H NMR (500 MHz, Pyridine-$d_5$) and $^{13}$C NMR (100 MHz, Pyridine-$d_5$); HRESIMS m/z 1372.8555 [M+Na]$^+$ (calcd for $C_{64}H_{115}N_{15}NaO_{16}$, 1372.8538).

hypocrin NG E (41): colorless solid; $[\alpha]_D^{25}$ −4 (c 0.1, MeOH); CD (MeOH) λmax (Δε) 206 (−38.5), 221 (−21.7); $^1$H NMR (500 MHz, Pyridine-$d_5$) and $^{13}$C NMR (100 MHz, Pyridine-$d_5$); HRESIMS m/z 1386.8720 [M+Na]$^+$ (calcd for $C_{65}H_{117}N_{15}NaO_{16}$, 1386.8695).

hypocrin NG F (42): colorless solid; $[\alpha]_D^{25}$ −12 (c 0.1, MeOH); CD (MeOH) λmax (Δε) 206 (−23.8), 222 (−12.9); $^1$H NMR (500 MHz, Pyridine-$d_5$) and $^{13}$C NMR (100 MHz, Pyridine-$d_5$); HRESIMS m/z 1386.8722 [M+Na]$^+$ (calcd for $C_{65}H_{117}N_{15}NaO_{16}$, 1386.8695).

hypocrin NG G (43): colorless solid; $[\alpha]_D^{25}$ −10 (c 0.1, MeOH); CD (MeOH) λmax (Δε) 206 (−11.7), 222 (−6.9); $^1$H NMR (500 MHz, Pyridine-$d_5$) and $^{13}$C NMR (100 MHz, Pyridine-$d_5$); HRESIMS m/z 1386.8685 [M+Na]$^+$ (calcd for $C_{65}H_{117}N_{15}NaO_{16}$, 1386.8695).

Preparation of Amino Acid Standard Samples and Marfey's Analysis for the Absolute Configuration of Amino Acid.

Peptaibols (0.3 mg) was hydrolyzed in 300 µL of 6 N HCl at 110° C. overnight. After cooling to room temperature, the neutralized hydrolysate was evaporated to dryness and redissolved in 100 µL of water and 1 M NaHCO$_3$ (30 µL). A solution of N-α-(2,4-dinitro-5-fluorophenyl)-$_L$-alaninamide ($_L$-FDAA, Marfey's reagent, Sigma, 100 µL, 1% in acetone) was added to each reaction vial. The reaction mixture was heated at 45° C. for 1 h, quenched by adding 1 N HCl (30 µL), and then dissolved in CH$_3$CN (1 mL). 5 µL of the FDAA derivatives were analyzed by LC/MS (Kinetex C18, 2.6 µm, 100 Å, 75×3.0 mm, flow rate: 0.4 mL/min) at RT. Aqueous CH$_3$CN containing 0.1% TFA was used as the mobile phase in a gradient mode (10-50% CH$_3$CN/H$_2$O for 0-30 min). $_D$- and $_L$-amino acid authentic standards were prepared in the same way. The following retention times (min) were observed for the L-FDAA derivatives of the standards, respectively: 11.1 ($_L$-Ser) and 11.7 ($_D$-Ser), 12.1 ($_L$-Asp) and 13.2 ($_D$-Asp), 13.5 ($_L$-Glu) and 14.6 ($_D$-Glu), 14.6 ($_L$-Ala) and 16.7 ($_D$-Ala), 15.2 ($_L$-Pro) and 16.1 ($_D$-Pro), 19.0 ($_L$-Val) and 21.8 ($_D$-Val), 19.2 ($_L$-Iva) and 20.3 ($_D$-Iva), 21.0 ($_L$-Leuol) and 24.2 ($_D$-Leuol), 21.6 ($_L$-Ile) and 24.2 ($_D$-Ile), 21.6 ($_L$-allo-Ile) and 24.2 ($_D$-allo-Ile), 22.0 ($_L$-Leu) and 24.5 ($_D$-Leu).

Determination of the Absolute Configuration of Isoleucine.

The hydrolysate of peptaibols was obtained from the above-described method and dissolved in water (100 µl). A 200 µL of 5% trimethylamine in acetone and 200 µL of 1% GITC solution in acetone were added to the hydrolysate. The reaction vial was placed at room temperature (25° C.) for 15 min and quenched by adding 200 µL of 5% acetic acid. A 5 µL of the GITC derivatives were analyzed by LC/MS (Kinetex C18, 2.6 µm, 100 Å, 75×3.0 mm, flow rate: 0.4 mL/min, 10-30% CH$_3$CN/H$_2$O with 0.1% formic acid for 0-50 min). The authentic L-isoleucine and L-allo-isoleucine standards were prepared in the same way. The following retention times were observed for the GITC derivatives of the standards: tri (min) 48.5 ($_L$-allo-Ile) and 49.0 ($_L$-Ile).

Parasite Culture Conditions.

Culture was maintained following a modified Trager and Jensen protocol.[xxv] Multi-drug resistant *P. falciparum* line Dd2 was grown in RPMI 1640 supplemented with 25 mM HEPES pH 7.4, 26 mM NaHCO$_3$, 2% dextrose, 15 mg/L hypoxanthine, 25 mg/L gentamycin and 0.5% Albumax II in human A+ erythrocytes. Culture was maintained at 4% hematocrit at 37° C. with 5% CO$_2$.

Phenotypic Screen for Antiplasmodial Activity.

Antiplasmodial EC$_{50}$ was determined using a fluorescence based SYBR Green I assay with asynchronous culture.[xxvi] Parasites were diluted to 1% parasitemia, 2% hematocrit and incubated with serial dilutions of compounds in microtiter plates for 72 h at standard growth conditions. Plates were subsequently frozen at −80° C. to facilitate lysis. After thawing, plates were incubated with 1×SYBR Green I in lysis buffer (20 mM Tris-HCl, 0.08% saponin, 5 mM EDTA, 0.8% Triton X-100) for 45-60 min at room temperature. Fluorescence was measured at an excitation wavelength 485 nm, emission 530 nm in a Synergy Neo2 multimode reader (BioTek, Winsooki, VT). RFUs were normalized based on chloroquine treated and no treatment controls. For all compounds listed, serial dilutions were prepared in RPMI with final assay conditions of 0.2% DMSO or below.

Cytotoxicity Assays.

Cross selectivity for human cells was determined using HepG2 human hepatocytes and an MTS (3-(4,5-Dimethylthiazol-2-yl)-5-(3-carboxymethoxyphenyl)-2-(4-sulfophenyl)-2H-tetrazolium) based cytotoxicity assay. After seeding 2,250 cells per well into 384-well microtiter plates, cells were incubated for 24 h. Next, serial dilutions of compounds were added to the seeded plates and incubated for additional 48 h at 37° C., and 5% $CO_2$. Zero percent growth control wells were incubated with 5% Triton X-100 for 5 min prior to MTS addition and incubated for 4 h at identical growth conditions. Absorbance was then read at 490 nm in a Synergy Neo2 multi-mode reader (BioTek, Winsooki, VT) and values were normalized based on detergent lysed and no treatment controls.

Example 55

FIG. 10 shows hyperacetylation during trophozoite stage by 137LJ57K1.

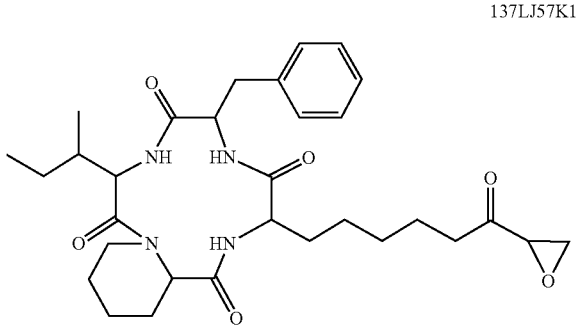 [SMILES: CCC(C)C1NC(=O)C(Cc2ccccc2)NC(=O)C(CCCCCC(=O)C2CO2)NC(=O)C2CCCCN2C1=O]

137LJ57K1

Figure 10A:
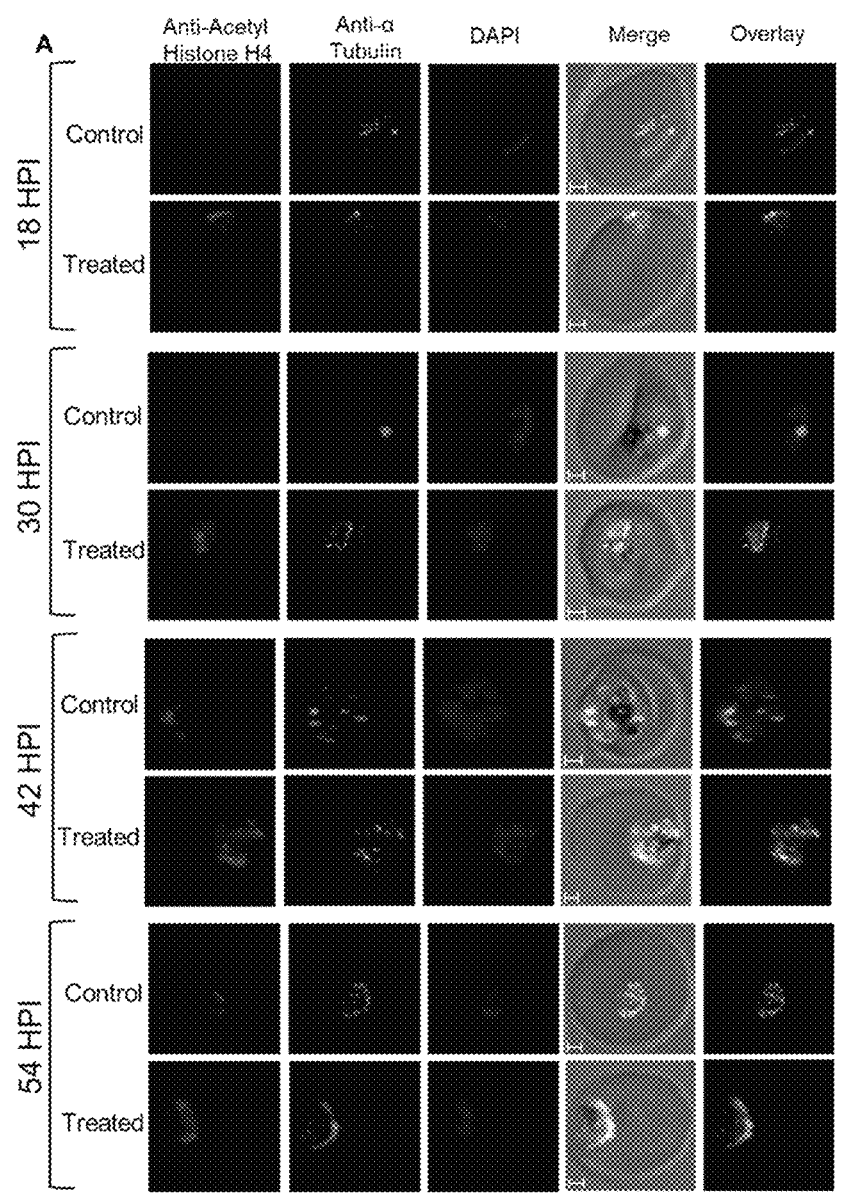
FIG. 10(A) shows photographs of trophozoites following treatment at 6 HPI with 137LJ57K1. Culture followed until 54 HPI. Scale bar represents 1 micron.
Figure 10B:
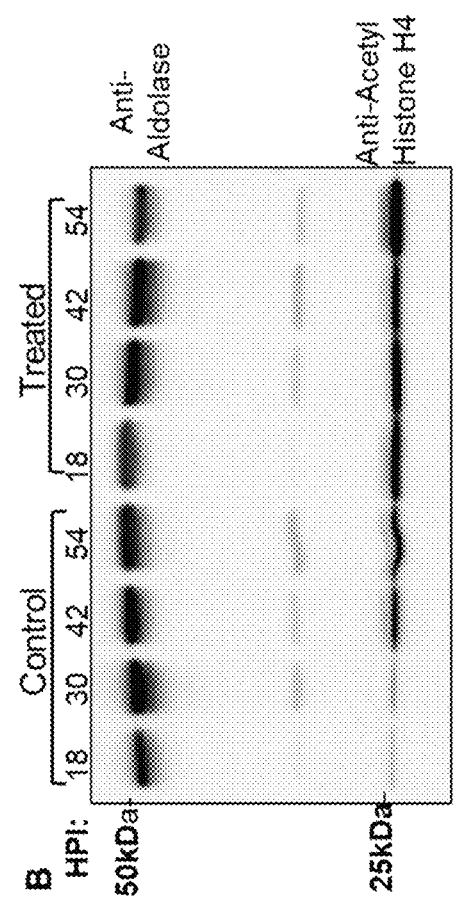
FIG. 10(B) shows a western blot showing acetylation following treatment at 6 HPI with 137LJ57K, initial impure extract of 137LJ57K1.
Figure 11:
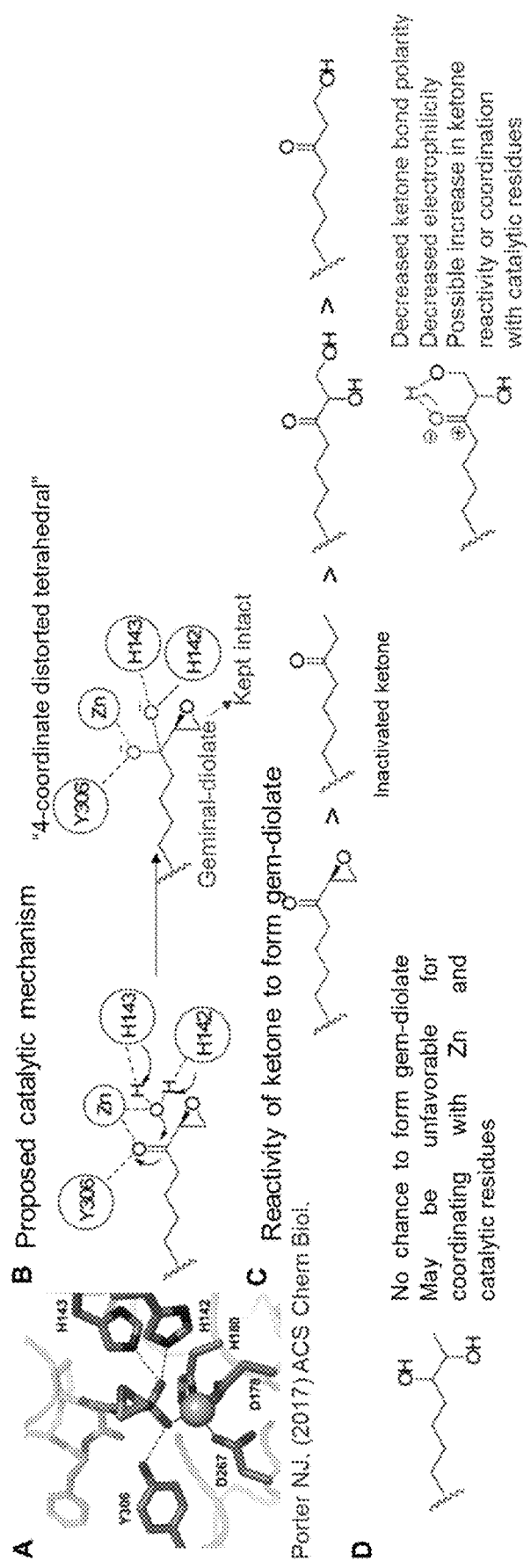
FIG. 11: shows diagrams illustrating SAR based on in-silico modeling and interaction of R2 group in catalytic pocket.

FIG. 10A shows IFA following treatment at 6 HPI with 137LJ57K1. Culture followed until 54 HPI. Scale bar represents 1 micron. FIG. 10(B) is a western blot showing acetylation following treatment at 6 HPI with 137LJ57K, initial impure extract of 137LJ57K1. 137LJ57K1 had a PfHDAC1 $EC_{50}$ (nM) of <0.2, a Dd2 $EC_{50}$ (nM) of 88, and a HepG2 $EC_{50}$ (nM) of 13,103.

FIGS. 17-20 provide multiple versions of cyclic tetrapeptides along with their $EC_{50}$s for various noted assays including Pf, Hep G2 and PfHDAC1 assays It should be borne in mind that all patents, patent applications, patent publications, technical publications, scientific publications, and other references referenced herein and in the accompanying appendices are hereby incorporated by reference in this application to the extent not inconsistent with the teachings herein.

While various embodiments of the present invention have been shown and described herein, it will be obvious that such embodiments are provided by way of example only. Numerous variations, changes and substitutions may be made without departing from the invention herein. Accordingly, it is intended that the invention be limited only by the spirit and scope of the appended claims.

REFERENCES

[1] WHO World Malaria Report 2018. https://www.who.int/malaria/publications/world-malaria-report-2018/en/Accessed on Nov. 19, 2018.

[1] (a) Hayton, K.; Su, X.-z. Genetic and biochemical aspects of drug resistance in malaria parasites. Curr. Drug Targets: Infect. Disord. 2004, 4, 1-10. (b) Sinha, S.; Medhi, B.; Sehgal, R. Challenges of drug-resistant malaria. Parasite 2014, 21, 61. (c) Blasco, B.; Leroy, D.; Fidock, D. □. □ntimalarial drug resistance: linking Plasmodium falciparum parasite biology to the clinic. Nat. Med. 2017, 23. 917-928.

[1] Lacerda, □. F.; Pelegrini, P. B.; de Oliveira, D. M.; Vasconcelos, É. □.; Grossi-de-Sá, M. F. Anti-parasitic peptides from arthropods and their application in drug therapy. Front. Microbial. 2016, 7, 91.

[1] (a) Boman, H. G.; Wade, D.; Boman, I. □.; Wåhlin, B.; Merrifield, R. B. □ntibacterial and antimalarial properties of peptides that are cecropin-melittin hybrids. FEBS Lett. 1989, 259, 103-106. (b) Gwadz, R. W; Kaslow, D.; Lee, J. Y.; Maloy, W. L.; Zasloff, M.; Miller, L. H. Effects of magainins and cecropins on the sporogonic development of malaria parasites in mosquitoes. Infect. Immun. 1989, 57, 2628-2633.

[1] (a) Carballar-Lejarazú, R.; Rodriguez, M. H.; de la Cruz Hernandez-Hernandez, F.; Ramos-Castaneda, J.; Possani, L. D.; Zurita-Ortega, M.; Reynaud-Garza, E.; Hern_ndez-Rivas, R.; Loukeris, T.; Lycett, G.; Lanz-Mendoza, H. Recombinant scorpine: a multifunctional antimicrobial peptide with activity against different pathogens. Cell. Mol. Life Sci. 2008, 65, 3081-3092. (b) Gao, B.; Xu, J.; del Carmen Rodriguez, M.; Lanz-Mendoza, H.; Hernández-Rivas, R.; Du, W.; Zhu, S. Characterization of two linear cationic antimalarial peptides in the scorpion Mesobuthus eupeus. Biochimie 2010, 92, 350-359.

[1] Vizioli, J.; Bulet, P.; Hoffmann, J. □.; Kafatos, F. C.; Müller, H. M.; Dimopoulos, G. Gambicin: A novel immune responsive antimicrobial peptide from the malaria vector Anopheles gambiae. Proc. Natl. Acad. Sci. USA 2001, 98, 12630-12635.

[1] (a) Linington, R. G.; Clark, B. R.; Trimble, E. E.; □lmanza, □.; Urena, L. D.; Kyle, D. E.; Gerwick, W. H. □ntimalarial peptides from marine cyanobacteria: isolation and structural elucidation of gallinamide A. J. Nat. Prod. 2008, 72, 14-17. (b) Zhao, L.; Kaiser, M.; Bode, H. B. Rhabdopeptide/xenortide-like peptides from Xenorhabdus innexi with terminal amines showing potent antiprotozoal activity. Org. Lett. 2018, 20, 5116-5120.

[1] Singh, S. B.; Zink, D. L.; Liesch, J. M.; Dombrowski, □. W; Darkin-Rattray, S. J.; Schmatz, D. M.; Goetz, M. □. Structure, histone deacetylase, and antiprotozoal activities of apicidins B and C, congeners of apicidin with proline and valine substitutions. Org. Lett. 2001, 3, 2815-2818.

[1] Hayashi, Y; Fukasawa, W; Hirose, T.; Iwatsuki, M.; Hokari, R.; Ishiyama, □.; Kanida, M.; Nonaka, K.; Take, □.; Otoguro, K.; Ōmura, S.; Shiomi, K.; Sunazuka, T. Kozupeptins, antimalarial agents produced by Paracamarosporium species: isolation, structural elucidation, total synthesis, and bioactivity. 2019. Org. Lett. (epub)

[1] Nagaraj, G.; Uma, M. V.; Shivayogi, M. S.; Balaram, H. □ntimalarial activities of peptide antibiotics isolated from fungi. Antimicrob. Agents Chemother. 2001, 45, 145-149.

[1] (a) Jaworski, □.; Kirschbaum, J.; Brückner, H. Structures of Trichovirins II, Peptaibol antibiotics from the mold Trichoderma viride NRRL 5243. J. Pept. Sci. 1999, 5, 341-351. (b) Przybylski, M.; Dietrich, I.; Manz, I.; Brückner, H. Elucidation of structure and microheterogeneity of the polypeptide antibiotics paracelsin and trichotoxin A-50 by fast atom bombardment mass spectrometry in combination with selective in situ hydrolysis. Biomedical mass spectrometry, 1984, 11, 569-582. (c) Iida, □.;

Sanekata, M.; Wada, S. I.; Fujita, T.; Tanaka, H.; Enoki, ☐.; Fuse, G.; Kanai, M.; ☐sami, K. Fungal metabolites. XVIII. new membrane-modifying peptides, trichorozins I-IV, from the fungus *Trichoderma harzianum*. *Chem. Pharm. Bull.* 1995, 43, 392-397. (d) Oh, S. U.; Yun, B. S.; Lee, S. J.; Kim, J. H.; Yoo, I. D. Atroviridins A-C and neoatroviridins A-D, novel peptaibol antibiotics produced by *Trichoderma atroviride*. F80317 *J. Antibiot* 2002, 55, 557-564. (e) Jaworski, ☐.; Brückner, H. Detection of new sequences of peptaibol antibiotics trichotoxins A-40 by on-line liquid chromatography-electrospray ionization mass spectrometry. *J. Chromatogr. A.* 1999, 862, 179-189. (f) Jiao, W. H.; Khalil, Z.; Dewapriya, P.; Salim, ☐. ☐.; Lin, H. W.; Capon, R. J. Trichodermides A-E: new peptaibols isolated from the Australian termite nest-derived fungus *Trichoderma virens* CMB-TN16. *J. Nat. Prod.* 2018, 81, 976-984.

[1] (a) Goulard, C.; Hlimi, S.; Rebuffat, S.; Bodo, B. Trichorzins H☐ and M☐, antibiotic peptides from *Trichoderma harzianum* I. Fermentation, isolation and biological properties. *J. Antibiot* 1995, 48, 1248-1253. (b) Hlimi, S.; Rebuffat, S.; Goulard, C.; Duchamp, S.; Bodo, B. Trichorzins HA and MA, antibiotic peptides from *Trichoderma harzianum* II. Sequence Determination. *J. Antibiot* 1995, 48, 1254-1261.

[1] (a) Fujii, K.; Ikai, Y.; Mayumi, T.; Oka, H.; Suzuki, M.; Harada K. A nonempirical method using LC/MS for determination of the absolute configuration of constituent amino acids in a peptide: Elucidation of limitations of Marfey's method and of its separation mechanism. *Anal. Chem.* 1997, 69, 3346-3352. (b) Fujii, K.; Ikai, Y.; Oka, H.; Suzuki, M.; Harada K. A nonempirical method using LC/MS for determination of the absolute configuration of constituent amino acids in a peptide: Combination of Marfey's method with mass spectrometry and its practical application. *Anal. Chem.* 1997, 69, 5146-5151.

[1] (a) Liu, D.; Lin, H.; Proksch, P.; Tang, X.; Shao, Z.; Lin, W. Microbacterins ☐ and B, new peptaibols from the deep sea Actinomycete *Microbacterium sediminis* sp. nov. YLB-01(T). *Org. Lett.* 2015, 17, 1220-1223. (b) De Zotti, M.; Damato, F.; Formaggio, F.; Crisma, M.; Schievano, E.; Mammi, S.; Kaptein, B.; Broxterman, Q. B.; Felock, P. J.; Hazuda, D. J.; Singh, S. B.; Kirschbaum, J.; Bruckner, H.; Toniolo, C. Total synthesis, characterization, and conformational analysis of the naturally occurring hexadecapeptide integramide A and a diastereomer. *Chemistry*. 2010, 16, 316-327. (c) Grauer, ☐. ☐.; Cabrele, C.; Zabel, M.; König, B. Stable right- and left-handed peptide helices containing C$^\alpha$-tetrasubstituted α-amino acids. *J. Org. Chem.* 2009, 74, 3718-3726.

[1] Hess, S.; Gustafson, K. R.; Milanowski, D. J.; ☐lvira, E.; Lipton, M. ☐.; Pannell, L. K. Chirality determination of unusual amino acids using precolumn derivatization and HPLC-ESI-MS. *J. Chromatogr. A.* 2004, 1035, 211-219.

[1] Rebuffat, S.; Goulard, C.; Bodo, B. Harzianin H B I, an 11-residue peptaibol from *Trichoderma harzianum*: isolation, sequence, solution synthesis and membrane activity. *J. Chem. Soc. Perkin Trans.* 1 1995, 14, 1849-1855.

[1] Augeven-Bour, I.; Rebuffat, S.; ☐uvin, C.; Goulard, C.; Prigent, Y.; Bodo, B. ☐ntibiotic peptides from *Trichoderma harzianum*: harzianins HC, proline-rich 14-residue peptaibols. *J. Chem. Soc. Perkin Trans.* 1 1997, 10, 1587-1594.

[1] (a) Singh, V. P.; Yedukondalu, N.; Sharma, V.; Kushwaha, M.; Sharma, R.; Chaubey, ☐.; Kumar, ☐.; Singh, D.; Vishwakarma, R. ☐. Lipovelutibols ☐-D: Cytotoxic lipopeptaibols from the Himalayan cold habitat fungus *Trichoderma velutinum*. *J. Nat. Prod.* 2018, 81, 219-226. (b) Tsantrizos, Y. S.; Pischos, S.; Sauriol, F.; Widden, P. Peptaibol metabolites of *Tolypocladium geodes*. *Can. J. Chem.* 1996, 74, 165-172. (c) Röhrich, C. R.; Iversen, ☐.; Jaklitsch, W. M.; Voglmayr, H.; Vilcinskas, ☐.; Nielsen, K. F.; Thrane, U.; von Döhren, H.; Brückner, H.; Degenkolb, T. Screening the biosphere: the fungicolous fungus *Trichoderma phellinicola*, a prolific source of hypophellins, new 17-, 18-, 19-, and 20-residue peptaibiotics. *Chem. Biodivers.* 2013. 10, 787-812. (d) Degenkolb, T.; Gräfenhan, T.; Berg, A.; Nirenberg, H. I.; Gams, W; Brückner, H. Peptaibiomics: screening for polypeptide antibiotics (peptaibiotics) from plant-protective *Trichoderma* species. *Chem. Biodivers.* 2006, 3, 593-610.

[1] Auvin-Guette, C.; Rebuffat, S.; Vuidepot, I.; Massias, M.; Bodo, B. Structural elucidation of trikoningins KA and KB, peptaibols from *Trichoderma koningii*. *J. Chem. Soc. Perkin Trans.* 1 1993, 2, 249-255.

[1] Auvin-Guette, C.; Rebuffat, S.; Prigent, Y.; Bodo, B. Trichogin A IV, an 11-residue lipopeptaibol from *Trichoderma longibrachiatum*. *J. Am. Chem. Soc.* 1992, 114, 2170-2174.

[1] China, N.; Blond, A.; Goulard, C.; Bodo, B.; Rebuffat, S. Structure and membrane properties of trichogin GB IX from *Trichoderma longibrachiatum*, the longest sequence among lipopeptaibols. *Peptides 2000, Proceedings of the 26th European Peptide Symposium*, Montpellier, France. 2000, 51-52.

[1] Fujita, T.; Iida, A.; Uesato, S.; Takaishi, Y.; Shingu, T.; Saito, M.; Morita, M. Structural elucidation of trichosporin-B-Ia, IIIa, IIId and V from *Trichoderma polysporum*. *J. Antibiot.* 1988, 41, 814-818.

[1] Huang, Q.; Tezuka, Y.; Kikuchi, T.; Nishi, A.; Tubaki, K.; Tanaka, K. Studies on metabolites of mycoparasitic fungi. II. Metabolites of *Trichoderma koningii*. *Chem. Pharm. Bull.* 1995, 43, 223-229.

[1] Iwatsuki, M.; Kinoshita, Y.; Niitsuma, M.; Hashida, J.; Mori, M.; Ishiyama, A.; Namatame, M.; Nishihara-Tsukashima, A.; Nonaka, K.; Masuma, R.; Otoguro, K.; Yamada, H.; Shiomi, K.; Omura, S. Antitrypanosomal peptaibiotics, trichosporins B-VIIa and B-VIIb, produced by *Trichoderma polysporum* FKI-4452. *J. Antibiot.* 2010, 63, 331-333.

[1] Trager, W; Jensen, J. B. Human malaria parasites in continuous culture. *Science,* 1976, 193, 673-675.

[1] Smilkstein, M.; Sriwilaijaroen, N.; Kelly, J. X.; Wilairat, P.; Riscoe, M. Simple and inexpensive fluorescence-based technique for high-throughput antimalarial drug screening. *Antimicrob. Agents Chemother.* 2004, 48, 1803-1806.

What is claimed is:

1. A method for treating malaria in a subject comprising administering to a subject in need thereof an effective amount of a composition comprising

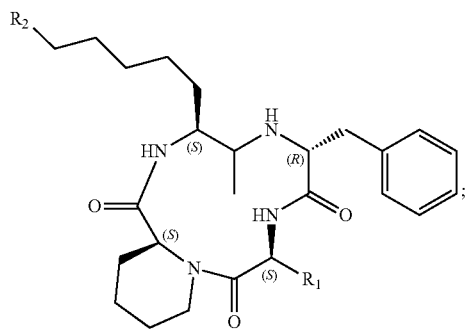

wherein $R_1$ is
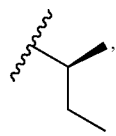 [SMILES: *[C@@H](C)CC]
and wherein $R_2$ is
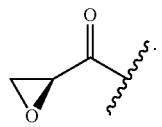 [SMILES: *C(=O)[C@@H]1CO1]
2. The method of claim 1, further comprising one or more conjunctive agents,
or pharmaceutically acceptable salt of the foregoing.
* * * * *